United States Patent
Lee et al.

(10) Patent No.: US 8,785,453 B2
(45) Date of Patent: Jul. 22, 2014

(54) ARYLPIPERAZINE-CONTAINING PURINE DERIVATIVES AND USES THEREOF

(75) Inventors: Jinhwa Lee, Yongin-si (KR); Eun-Jung Park, Yongin-si (KR); Suk Youn Kang, Yongin-si (KR); Younggyu Kong, Yongin-si (KR); Junwon Lee, Yongin-si (KR); Hyun Jung Kim, Yongin-si (KR); Myung Eun Jung, Yongin-si (KR); Ki-Nam Lee, Yongin-si (KR); Jeongmin Kim, Yongin-si (KR); Ae Nim Pae, Seoul (KR); Woo-Kyu Park, Daejeon (KR)

(73) Assignee: Green Cross Corporation, Yongin-Si (KR)

( * ) Notice: Subject to any disclaimer, the term of this patent is extended or adjusted under 35 U.S.C. 154(b) by 0 days.

(21) Appl. No.: 13/509,140

(22) PCT Filed: Nov. 5, 2010

(86) PCT No.: PCT/KR2010/007804
§ 371 (c)(1),
(2), (4) Date: May 10, 2012

(87) PCT Pub. No.: WO2011/059207
PCT Pub. Date: May 19, 2011

(65) Prior Publication Data
US 2012/0232090 A1    Sep. 13, 2012

Related U.S. Application Data

(60) Provisional application No. 61/261,179, filed on Nov. 13, 2009.

(51) Int. Cl.
*A61K 31/52* (2006.01)
*C07D 473/34* (2006.01)

(52) U.S. Cl.
USPC ........................................ 514/263.2; 544/277

(58) Field of Classification Search
USPC ............................................................ 544/277
See application file for complete search history.

(56) References Cited

U.S. PATENT DOCUMENTS

| | | | | |
|---|---|---|---|---|
| 3,919,226 | A | * | 11/1975 | Thiel et al. ..................... 544/277 |
| 5,977,099 | A | * | 11/1999 | Nickolson ................ 514/214.02 |
| 2006/0241120 | A1 | | 10/2006 | Griffith |
| 2007/0219182 | A1 | | 9/2007 | Lubisch et al. |
| 2009/0036448 | A1 | | 2/2009 | Sekiguchi et al. |

OTHER PUBLICATIONS

Griffith et al. "Discovery of 1-[9-(4-Chlorophenyl)-9H-purin-6-yl]-4-ethlyaminopiperidine-4-carboxylic Acid Amide Hydrochloride (CP-945,598), a Novel Potent, and Selective Cannabinoid Type 1 Receptor Antagonist", J. Med. Chem., 2009, vol. 52, pp. 234-237.
Kelley et al. "6-(Alkylamino)-9-alkylpurines. A New Class of Potential Antipsychotic Agents", J. Med. Chem., 1997., vol. 40, pp. 3207-3216.
Miller-Moslin et al. "1-Amino-4-benzylphthalazines as Orally Bioavailable Smoothened Antagonists with Antitumor Activity", J. Med. Chem., 2009., vol. 52, pp. 3954-3968.
Zhou et al. "Synthesis, Potency, and in Vivo Evaluation of 2-Piperazin-1-ylquinoline Analogues as Dual Serotonin Reuptake Inhibitors and Serotonin 5-$HT_{1A}$ Receptor Antagonists", J. Med. Chem., 2009., vol. 52, pp. 4955-4959.
Wan et al. "Efficacious 11 β-Hydroxysteroid Dehydrogenase Type I Inhibitors in the Diet-Induced Obesity Mouse Model", J. Med. Chem., 2009, vol. 52, pp. 5449-5461.
Hoeglund et al. "Structure-Activity Relationship of Quinoline Derivatives as Potent and Selective $α_{2C}$-Adrenoceptor Antagonists", J. Med. Chem., 2006, vol. 49, pp. 6351-6363.
International Search Report, PCT/KR2010/007804, dated Jul. 27, 2011.

* cited by examiner

*Primary Examiner* — Golam M M Shameem
*Assistant Examiner* — Laura Daniel
(74) *Attorney, Agent, or Firm* — Sughrue Mion, PLLC

(57) ABSTRACT

A novel arylpiperazine-containing purine derivatives and a pharmaceutical composition comprising the same as an active ingredient, which are useful for preventing or treating depressive disorders, are provided.

6 Claims, 2 Drawing Sheets

ARYLPIPERAZINE-CONTAINING PURINE DERIVATIVES AND USES THEREOF

CROSS REFERENCE TO RELATED APPLICATIONS

This application is a National Stage of International Application No. PCT/KR2010/007804 filed Nov. 5, 2010, claiming priority based on U.S. Patent Application No. 61/261,179 filed Nov. 13, 2009, the contents of all of which are incorporated herein by reference in their entirety.

FIELD OF THE INVENTION

The present invention relates to a novel arylpiperazine-containing purine derivatives for treating depressive disorders.

BACKGROUND OF THE INVENTION

Depressive disorders involve all major bodily functions, mood, and thoughts, affecting the ways in which an individual eats and sleeps, feel about themselves, and think. Without treatment, depression symptoms can last for weeks, months or years. Depression is the leading cause of disability in the United States. An increasing number of treatment options have become more available over the past two decades for individuals with major depression disorder. The clinical description of depression is complex, covering a broad range of symptoms that lack a unifying biological hypothesis. Depression has both genetic and environmental components, with linkage studies suggesting it is a polygenic disorder. Modern treatment for depression, which focuses exclusively on agents that modulate monoamine neurotransmission, began with a monoamine oxidase inhibitor (MAOI). MAOIs increase serotonin and norepinephrine concentrations in the brain by inhibiting the MAO enzyme. They are highly effective in treating depression but are used only scarcely owing to potentially dangerous drug interaction effects.

A second breakthrough in depression treatment came from chlorpromazine derivatives. Imipramine, one such derivative, was exceptionally effective in patients who had severe depression. Imipramine is a tricyclic antidepressant (TCA) that acts by inhibiting cellular reuptake mechanisms for norepinephrine and serotonin to increase activity within these G protein-coupled receptor (GPCR) families. Imipramine retains activity at GPCRs, but this activity contributes to unattractive side effects. Subsequently, structural analogs of diphenhydramine were discovered as novel antidepressants. The phenoxyphenylpropylamine was used to identify fluoxetine, the first selective serotonine reuptake inhibitor (SSRI). The remarkable success of fluoxetine as an antidepressant extended to the identification of other SSRIs including paroxetine, citalopram, fluvoxamine, and sertraline. SSRIs became a family of antidepressants considered to be the current standard of drug treatment. It is thought that one cause of depression is an inadequate amount of serotonin. SSRIs are said to work by preventing the reuptake of serotonin by the presynaptic neuron, thus maintaining higher levels of 5-HT in the synapse. These antidepressants typically have fewer adverse events and side effects than the tricyclics or the MAOIs, although such effects as drowsiness, dry mouth, nervousness, anxiety, insomnia, decreased appetite, and decreased ability to function sexually may occur.

Although there are a number of treatments currently available, there are still clear opportunities for improvement of existing therapies. Much research has been focused to address unmet medical needs of currently available drug therapies: slow onset of action, inability to achieve full remission, difficulty of targeting significant populations of nonresponding patients, and minimalization of residual side effects including sexual dysfunction. Recent developments include serotonin and norepinephrine reuptake inhibitors (SNRIs), and norepinephrine and dopamine reuptake inhibitors (NDRIs), implying multiple neurotransmitter pathways in the spectrum of disorders that incorporate major depression [Pacher, P. et al., Curr. Med. Chem., 11, 925-943 (2004)]. It is the hope that drugs acting by newer mechanisms will meet some, if not all, of these unmet needs.

Along the line, SARI (serotonin antagonist/reuptake inhibitor) drugs that block both the serotonin 5-HT$_2$ receptors and the serotonin transporters have been developed. Typical examples are Bristol-Myers Squibb's nefazodone [DeBattista, C. et al., Biol. Psychiatry, 44, 341 (1998)], Yamanouchi's YM-992 [Hatanaka, K. et al., Neuropharmacology, 35(11), 1621 (1997)] and Lilly's LY367265 [Pullar, I. A. et al., Eur. J. Pharmacol., 407(1-2), 39 (2000)]:

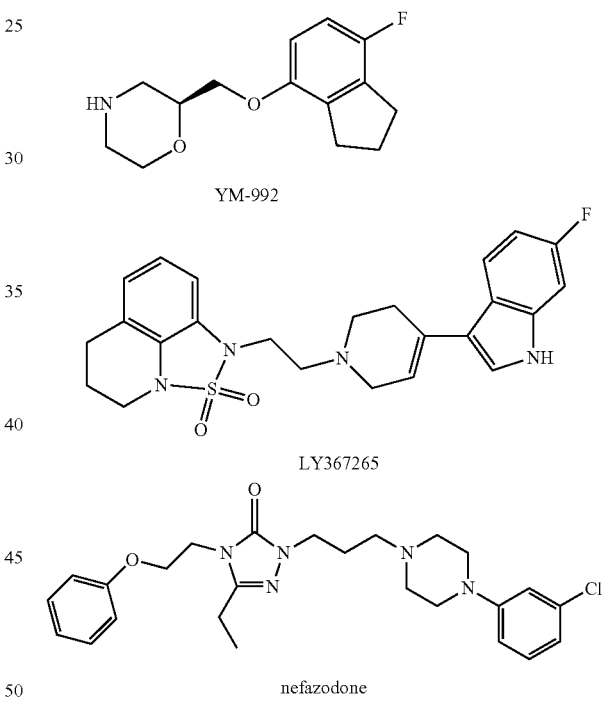

These compounds demonstrated improved results in the treatment of central nervous system disorders, compared with either the serotonin 5-HT$_2$ receptors or the selective serotonin reuptake inhibitors only, in clinical effects, side effects, reduction in drug action time, etc. (see [Avila, A. et al., J. Clin. Psychopharmacol., 23(5), 509 (2003)]). Nefazodone is most closely related to trazodone in terms of chemical structure (see [Temple, D. L, Jr. et al., U.S. Pat. No. 4,338,317]). Unlike most SSRIs, nefazodone is reported to have no negative effects on libido or sexual functioning. Nefazodone's claimed advantages over other antidepressants include reduced possibility of disturbed sleep or sexual dysfunction, and ability to treat some patients who did not respond to other antidepressant drugs (see [Greene, D. S. et al., Clin. Pharmacokinet., 33(4), 260 (1997)]). However, nefazodone is a potent inhibitor of the CYP3A4 isoenzyme both in vitro and in vivo (see [Kent, J. M., *Lancet*, 355, 911-918 (2000)]).

In the end, its sale was discontinued in 2003 in some countries, due to the small possibility of hepatic injury, which could lead to the need for a liver transplant, or even death. At 2004, Bristol-Myers Squibb withdrew nefazodone in the United States.

In this regard, there is an urgent medical need on the discovery of new drugs that act as a mode of nefazodone, but have better developability characteristics. This new class of antidepressants would significantly broaden the physician's and patient's choice.

SUMMARY OF THE INVENTION

It is a primary object of the present invention to provide a novel arylpiperazine-containing purine compound of formula (I), or a pharmaceutically acceptable salt or a prodrug thereof, which is useful for preventing or treating depressive disorders.

It is another object of the present invention to provide a pharmaceutical composition for preventing or treating depressive disorders, comprising the inventive compound as an active ingredient.

It is a further object of the present invention to provide a method for preventing or treating depressive disorders, which comprises administering the inventive compound to a mammal in need thereof.

In accordance with one aspect of the present invention, there is provided a compound of formula (I), or a pharmaceutically acceptable salt or a prodrug thereof:

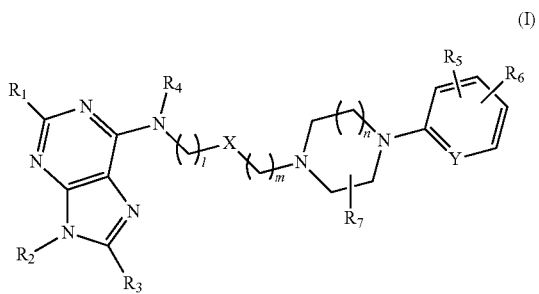

(I)

wherein, $R_1$ represents hydrogen or —$CH_3$;

$R_2$ represents hydrogen, carbocycle, substituted carbocycle, aryl, substituted aryl, $C_{1-8}$ alkyl, $C_{1-8}$ alkyl substituted with hydroxyl, alkenyl or alkynyl, acyloxy, $C_{1-6}$ alkoxy, substituted $C_{1-6}$ alkoxy, $C_{3-5}$ alkenyloxy, substituted $C_{3-5}$ alkenyloxy, $C_{3-5}$ alkynyloxy, substituted $C_{3-5}$ alkynyloxy, aryloxy, substituted aryloxy, heteroaryl, substituted heteroaryl, heteroaryloxy, heteroaryloxy substituted with alkoxy or halogen, heterocycloalkyl, substituted heterocycloalkyl, $C_{2-6}$ alkenyl, $C_{2-6}$ alkenyl substituted with alkoxy or halogen, $C_{2-6}$ alkynyl, $C_{2-6}$ alkynyl substituted with alkoxy or halogen, —$(CH_2)_p$—$C_{3-6}$ carbocycle, —$(CH_2)_p$—$C_{3-6}$ carbocycle substituted with alkoxy or halogen, or —$(CH_2)_q$—R', and R' being phenyl, furanyl, benzofuranyl, thienyl, benzothienyl, pyridinyl, pyridiminyl, pyrazinyl, pyridizinyl, tetrahydrofuranyl, tetrahydropyranyl, dioxanyl, 1,4-benzodioxanyl, benzo[1,3]dioxolyl, substituted phenyl, furanyl, benzofuranyl, thienyl, benzothienyl, pyridinyl, pyridiminyl, pyrazinyl, pyridizinyl, tetrahydrofuranyl, tetrahydropyranyl, dioxanyl, 1,4-benzodioxanyl or benzo[1,3]dioxolyl which are independently substituted with one or more halogen, $C_{1-3}$ alkyl, $C_{1-3}$ alkyl having one to three fluorine substituents, $C_{1-3}$ alkoxy or $C_{1-3}$ alkoxy having one to three fluorine substituents, and p and q being independently 1 or 2;

$R_3$ represents hydrogen, $C_{1-4}$ alkyl, substituted $C_{1-4}$ alkyl, $C_{3-7}$ carbocycle, substituted $C_{3-7}$ carbocycle, aryl, substituted aryl, heteroaryl, substituted heteroaryl, heterocycloalkyl, or substituted heterocycloalkyl;

$R_4$ represents hydrogen or $C_{1-3}$ alkyl;

$R_5$ and $R_6$ are each independently hydrogen, halogen, $C_{1-3}$ alkyl, $C_{1-3}$ alkoxy, cyano, monofluoromethyl, difluoromethyl, or trifluoromethyl, or $R_5$ and $R_6$, together with the aryl ring to which they are bonded, form a 5- to 7-membered saturated or unsaturated heterocyclic ring, aryl ring, or aryl ring substituted with one or more $C_{1-3}$ alkyl, $C_{1-3}$ alkoxy, halogen, trifluoromethyl, or cyano;

$R_7$ represents hydrogen or $C_{1-3}$ alkyl;

when l=1, m=0 or l=0, m=1, X is —$CH_2$—;

when l=1 or 2, m=1 or 2 and both of l and m are not 2, X is —$CH_2$— or —CHOH—;

Y is —N= or

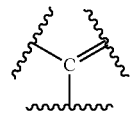

with the proviso that when Y is —N=, $R_5$ or $R_6$ cannot be connected to Y; and n is 1 or 2.

In accordance with another aspect of the present invention, there is provided a pharmaceutical composition for preventing or treating depressive disorders, which comprises the compound as an active ingredient, and a pharmaceutically acceptable carrier.

In accordance with a further aspect of the present invention, there is provided a method for preventing or treating depressive disorders, which comprises administering the compound to a mammal in need thereof.

BRIEF DESCRIPTION OF DRAWINGS

The above and other objects and features of the present invention will become apparent from the following description of the invention taken in conjunction with the following accompanying drawings, which respectively show.

DETAILED DESCRIPTION OF THE INVENTION

Figure 1:
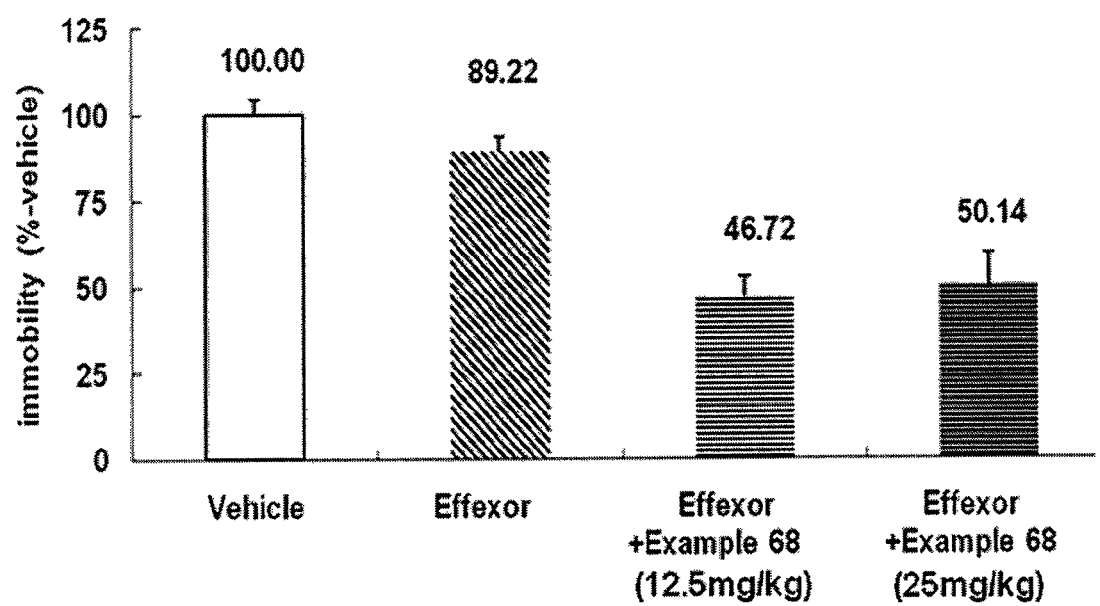
FIG. 1: a graph showing the measurement result for synergy effect depending on combination of the inventive compound (Example 68, 12.5 mg/kg or 25 mg/kg) and Effexor (25 mg/kg)

Hereinafter, a detailed description of the present invention is given.

As used herein, the term "alkyl" refers to a straight or branched chain saturated hydrocarbon radical. Examples of "alkyl" as used herein include, but are not limited to, methyl, ethyl, n-propyl, isopropyl, n-butyl, isobutyl, t-butyl, n-pentyl, isopentyl and hexyl.

As used herein, the term "substituted alkyl" refers to a straight or branched chain saturated hydrocarbon radical, which is optionally substituted with one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heteroaryloxy, heterocyclic, aminosulfonyl, sulfonylamino, carboxyamide, ureido, nitro, cyano and halogen.

As used herein, the term "alkenyl" refers to a straight or branched chain hydrocarbon radical having at least one carbon-carbon double bond. Examples of "alkenyl" as used herein include, but are not limited to, ethenyl and propenyl.

As used herein, the term "substituted alkenyl" refers to a straight or branched chain hydrocarbon radical having at least one carbon-carbon double bond, which has optional substituents selected from the group consisting of $C_{1-3}$ alkyl optionally having one to three fluorine substituents, amino, aryl, cyano and halogen.

As used herein, the term "alkynyl" refers to a straight or branched chain hydrocarbon radical having at least one carbon-carbon triple bond. Examples of "alkynyl" as used herein include, but are not limited to, acetylenyl and 1-propynyl.

As used herein, the term "substituted alkynyl" refers to a straight or branched chain hydrocarbon radical having at least one carbon-carbon triple bond, optionally having one or more substituents selected from the group consisting of $C_{1-3}$ alkyl optionally having one to three fluorine substituents, amino, aryl and halogen.

As used herein, the term "halogen" refers to fluorine (F), chlorine (Cl), bromine (Br), or iodine (I).

As used herein, the term "carbocycle" refers to a non-aromatic cyclic hydrocarbon radical composed of three to seven carbon atoms. Five- to seven-membered rings may contain a double bond in the ring structure. Exemplary "carbocycle" groups include, but are not limited to, cyclopropyl, cyclobutyl, cyclopentyl, cyclopentenyl, cyclohexyl, and cycloheptyl.

As used herein, the term "substituted carbocycle" refers to a non-aromatic cyclic hydrocarbon radical composed by three to seven carbon atoms, which is optionally substituted with one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heterocyclic, aminosulfonyl, sulfonylamino, carboxyamide, nitro, ureido, cyano and halogen.

As used herein, the term "aryl" refers to an optionally substituted benzene ring or refers to a ring system which may result by fusing one or more optional substituents. Exemplary optional substituents include substituted $C_{1-3}$ alkyl, substituted $C_{2-3}$ alkenyl, substituted $C_{2-3}$ alkynyl, heteroaryl, heterocyclic, aryl, alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, or ureido. Such a ring or ring system may be optionally fused to aryl rings (including benzene rings) optionally having one or more substituents, carbocycle rings or heterocyclic rings. Examples of "aryl" groups include, but are not limited to, phenyl, naphthyl, tetrahydronaphthyl, biphenyl, indanyl, anthracyl or phenanthryl, as well as substituted derivatives thereof.

As used herein, the term "heteroaryl" refers to an optionally substituted monocyclic five to six-membered aromatic ring containing one or more heteroatomic substitutions selected from S, SO, $SO_2$, O, N, or N-oxide, or refers to such an aromatic ring fused to one or more rings such as heteroaryl rings, aryl rings, heterocyclic rings, or carbocycle rings (e.g., a bicyclic or tricyclic ring system), each having optional substituents.

Examples of optional substituents are selected from the group consisting of substituted $C_{1-3}$ alkyl, substituted $C_{2-3}$ alkenyl, substituted $C_{2-3}$ alkynyl, heteroaryl, heterocyclic, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen and ureido. Examples of "heteroaryl" groups used herein include, but are not limited to, benzoimidazolyl, benzothiazolyl, benzoisothiazolyl, benzothiophenyl, benzopyrazinyl, benzotriazolyl, benzo[1,4]dioxanyl, benzofuranyl, 9H-a-carbolinyl, cinnolinyl, furanyl, furo[2,3-b]pyridinyl, imidazolyl, imidazolidinyl, imidazopyridinyl, isoxazolyl, isothiazolyl, isoquinolinyl, indolyl, indazolyl, indolizinyl, naphthyridinyl, oxazolyl, oxothiadiazolyl, oxadiazolyl, phthalazinyl, pyridyl, pyrrolyl, purinyl, pteridinyl, phenazinyl, pyrazolyl, pyridyl, pyrazolopyrimidinyl, pyrrolizinyl, pyridazyl, pyrazinyl, pyrimidyl, 4-oxo-1,2-dihydro-4H-pyrrolo[3,2,1-ij]-quinolin-4-yl, quinoxalinyl, quinazolinyl, quinolinyl, quinolizinyl, thiophenyl, triazolyl, triazinyl, tetrazolopyrimidinyl, triazolopyrimidinyl, tetrazolyl, thiazolyl, thiazolidinyl, and substituted versions thereof.

As used herein, the term "heterocyclic", "heterocycle" or "heterocycloalkyl" refers to a three to seven-membered ring containing one or more heteroatomic moieties selected from S, SO, $SO_2$, O, N, or N-oxide, optionally substituted with one or more substituents selected from the group which includes substituted $C_{1-3}$ alkyl, substituted $C_{2-3}$ alkenyl, substituted $C_{2-3}$ alkynyl, heteroaryl, heterocyclic, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, and ureido. Such a ring can be saturated or have one or more degrees of unsaturation. Such a ring may be optionally fused to one or more "heterocyclic" ring(s), aryl ring(s), heteroaryl ring(s) or carbocycle ring(s), each having optional substituents.

Examples of "heterocyclic", "heterocycle" or "heterocycloalkyl" moieties include, but are not limited to, 1,4-dioxanyl, 1,3-dioxanyl, pyrrolidinyl, pyrrolidin-2-onyl, piperidinyl, imidazolidine-2,4-dionepiperidinyl, piperazinyl, piperazine-2,5-dionyl, morpholinyl, dihydropyranyl, dihydrocinnolinyl, 2,3-dihydrobenzo[1,4]dioxinyl, 3,4-dihydro-2H-benzo[b][1,4]-dioxepinyl, tetrahydropyranyl, 2,3-dihydrofuranyl, 2,3-dihydrobenzofuranyl, dihydroisoxazolyl, tetrahydrobenzodiazepinyl, tetrahydroquinolinyl, tetrahydrofuranyl, tetrahydronaphthyridinyl, tetrahydropurinyl, tetrahydrothiopyranyl, tetrahydrothiophenyl, tetrahydroquinoxalinyl, tetrahydropyridinyl, tetrahydrocarbolinyl, 4H-benzo[1,3]-dioxinyl, benzo[1,3]dioxonyl, 2,2-difluorobenzo-[1,3]-dioxonyl, 2,3-dihydro-phthalazine-1,4-dionyl, and isoindole-1,3-dionyl.

As used herein, the term "alkoxy" refers to the group $—OR_a$, where $R_a$ is alkyl as defined above. The alkoxy group is optionally substituted with one or more substituents selected from the group consisting of $C_{1-3}$ alkyl or halogen. Exemplary alkoxy groups useful in the present invention include, but are not limited to, methoxy, difluoromethoxy, trifluoromethoxy, ethoxy, n-propoxy, isopropoxy, n-butoxy and t-butoxy.

As used herein, the term "alkenyloxy" refers to —$OR_b$, where $R_b$ is alkenyl as defined above. The alkenyloxy group is optionally substituted with one or more substituents selected from the group consisting of $C_{1-3}$ alkyl or halogen.

As used herein, the term "alkynyloxy" refers to —$OR_c$, where $R_c$ is alkynyl as defined above. The alkynyloxy group is optionally substituted with one or more substituents selected from the group consisting of $C_{1-3}$ alkyl or halogen.

As used herein, the term "aralkoxy" refers to the group —$OR_a n_d$, wherein $R_a$ is alkyl and $R_d$ is aryl as defined above. The aralkoxy group is optionally substituted with one or more substituents selected from the group consisting of $C_{1-3}$ alkyl or halogen.

As used herein, the term "aryloxy" refers to the group —$OR_d$, wherein $R_d$ is aryl as defined above. The aryloxy group is optionally substituted with one or more substituents selected from the group consisting of $C_{1-3}$ alkyl or halogen.

As used herein, the term "heteroaryloxy" refers to -$OR_e$, where $R_e$ is heteroaryl as defined above. The heteroaryloxy group is optionally substituted with one or more substituents selected from the group consisting of $C_{1-3}$ alkyl or halogen.

As used herein, the term "mercapto" refers to the group —SH.

As used herein, the term "sulfanyl" refers to the group —$SR_f$, wherein $R_f$ is substituted alkyl, substituted carbocycle, aryl, heteroaryl or heterocyclic, as defined above.

As used herein, the term "sulfinyl" refers to the group —S—(O)$R_f$, wherein $R_f$ is substituted alkyl, substituted carbocycle, aryl, heteroaryl or heterocyclic, as defined above.

As used herein, the term "sulfonyl" refers to the group —S(O)$_2R_f$, wherein $R_f$ is substituted alkyl, substituted carbocycle, aryl, heteroaryl or heterocyclic, as defined above.

As used herein, the term "oxo" refers to the group =O.

As used herein, the term "hydroxy" refers to the group —OH.

As used herein, the term "amino" refers to the group —$NH_2$. The amino group is optionally substituted with substituted alkyl, substituted carbocycle, aryl, heteroaryl or heterocyclic, as defined above.

As used herein, the term "cyano" refers to the group —CN.

As used herein, the term "aminosulfonyl" refers to the group —S(O)$_2NH_2$. The aminosulfonyl group is optionally substituted with substituted alkyl, substituted carbocycle, aryl, heteroaryl or heterocyclic, as defined above.

As used herein, the term "sulfonylamino" refers to the group —NHS(O)$_2R_f$ wherein $R_f$ is substituted alkyl, substituted carbocycle, aryl, heteroaryl or heterocyclic, as defined above.

As used herein, the term "carboxyamide" refers to the group —NHC(O)$R_f$ wherein $R_f$ is substituted alkyl, substituted carbocycle, aryl, heteroaryl or heterocyclic, as defined above.

As used herein, the term "carboxy" refers to the group —C(O)OH. The carboxy group is optionally substituted with substituted alkyl, substituted carbocycle, aryl, heteroaryl or heterocyclic, as defined above.

As used herein, the term "aminocarbonyl" refers to the group —C(O)$NH_2$. The aminocarbonyl group is optionally substituted with substituted alkyl, substituted carbocycle, aryl, heteroaryl or heterocyclic, as defined above.

As used herein, the term "ureido" refers to the group —NHC(O)$NHR_g$ wherein $R_g$ is hydrogen, alkyl, carbocycle or aryl as defined above.

As used herein, the term "guanidino" refers to the group —NHC(=NH)$NH_2$.

As used herein, the term "acyl" refers to the group —C(O)$R_h$, wherein $R_h$ is alkyl, carbocycle, or heterocyclic as defined above.

As used herein, the term "aroyl" refers to the group —C(O)$R_d$, wherein $R_d$ is aryl as defined above.

As used herein, the term "heteroaroyl" refers to the group —C(O)$R_e$, wherein $R_e$ is heteroaryl as defined above.

As used herein, the term "acyloxy" refers to the group —OC(O)$R_h$, wherein $R_h$ is alkyl, carbocycle, or heterocyclic as defined above.

As used herein, the term "aroyloxy" refers to the group —OC(O)$R_d$, wherein $R_d$ is aryl as defined above.

As used herein, the term "heteroaroyloxy" refers to the group —OC(O)$R_e$, wherein $R_e$ is heteroaryl as defined above.

As used herein, the term "pharmaceutically acceptable salt(s)", refers to those salts of compounds of the invention that are safe and effective for topical use in mammals and that possess the desired biological activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts (see [Berge, et al., *J. Pharm. Sci.*, 66, 1-19 (1977)]).

Preferable compounds of the present invention are those of formula (I) wherein, $R_1$ represents hydrogen or —$CH_3$;

$R_2$ represents hydrogen, $C_{3-7}$ carbocycle, allyl, propargyl, heterocycloalkyl, aryl, aryl substituted with halogen or $C_{1-3}$ alkyl, heteroaryl, or heteroaryl substituted with halogen or $C_{1-3}$ alkyl;

$R_3$ represents hydrogen, $C_{3-7}$ carbocycle, allyl, propargyl, heterocycloalkyl, aryl, aryl substituted with halogen or $C_{1-3}$ alkyl, heteroaryl, or heteroaryl substituted with halogen or $C_{1-3}$ alkyl;

$R_4$ represents hydrogen or $C_{1-3}$ alkyl;

$R_5$ and $R_6$ are each independently halogen, $C_{1-3}$ alkyl or $C_{1-2}$ alkoxy;

$R_7$ represents $C_{1-3}$ alkyl;

when l=1, m=0 or l=0, m=1, X is —$CH_2$—;

when l=1 or 2, m=1 or 2 and both of l and m are not 2, X is —$CH_2$— or —CHOH—;

Y is

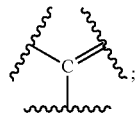 [SMILES: *C(*)=*]

and n is 1 or 2.

More preferred compounds useful in the present invention are selected from the group consisting of:

N-(3-(4-(2,3-dichlorophenyl)piperazin-1-yl)propyl)-8,9-diphenyl-9H-purine-6-amine;
N-(3-(4-(2,3-dichlorophenyl)piperazin-1-yl)propyl)-9-phenyl-8-propyl-9H-purine-6-amine;
N-(3-(4-(2,3-dichlorophenyl)piperazin-1-yl)propyl)-8-methyl-9-phenyl-9H-purine-6-amine;
N-(3-(4-(2,3-dimethylphenyl)piperazin-1-yl)propyl)-8-methyl-9-phenyl-9H-purine-6-amine;
N-(3-(4-(2,3-dichlorophenyl)piperazin-1-yl)propyl)-8-ethyl-9-phenyl-9H-purine-6-amine;
N-(3-(4-(2,3-dimethylphenyl)piperazin-1-yl)propyl)-8-ethyl-9-phenyl-9H-purine-6-amine;
N-(2-(4-(2,3-dichlorophenyl)piperazin-1-yl)ethyl)-8-methyl-9-phenyl-9H-purine-6-amine;
N-(2-(4-(2,3-dichlorophenyl)piperazin-1-yl)ethyl)-8-ethyl-9-phenyl-9H-purine-6-amine;
N-(2-(4-(2,3-dimethylphenyl)piperazin-1-yl)ethyl)-8-ethyl-9-phenyl-9H-purine-6-amine;
N-(2-(4-(2,3-dichlorophenyl)piperazin-1-yl)ethyl)-9-phenyl-8-propyl-9H-purine-6-amine;
N-(2-(4-(2,3-dimethylphenyl)piperazin-1-yl)ethyl)-9-phenyl-8-propyl-9H-purine-6-amine;
N-(3-(4-(2,3-dimethylphenyl)piperazin-1-yl)propyl)-9-phenyl-9H-purine-6-amine;
N-(2-(4-(2,3-dimethylphenyl)piperazin-1-yl)ethyl)-9-phenyl-9H-purine-6-amine;
N-(3-(4-(2,3-dichlorophenyl)piperazin-1-yl)propyl)-9-phenyl-9H-purine-6-amine;
1-(4-(2,3-dichlorophenyl)piperazin-1-yl)-3-(9-phenyl-9H-purin-6-ylamino)propan-2-ol;
N-(2-(4-(2,3-dichlorophenyl)piperazin-1-yl)ethyl)-8,9-diphenyl-9H-purine-6-amine;
N-(2-(4-(2,3-dimethylphenyl)piperazin-1-yl)ethyl)-8,9-diphenyl-9H-purine-6-amine;
N-(3-(4-(2,3-dimethylphenyl)piperazin-1-yl)propyl)-8,9-diphenyl-9H-purine-6-amine;
1-(4-(2,3-dichlorophenyl)piperazin-1-yl)-3-(8,9-diphenyl-9H-purin-6-ylamino)propan-2-ol;
1-(4-(2,3-dichlorophenyl)piperazin-1-yl)-3-(8-methyl-9-phenyl-9H-purin-6-ylamino)propan-2-ol;
1-(4-(2,3-dichlorophenyl)piperazin-1-yl)-3-(8-ethyl-9-phenyl-9H-purin-6-ylamino)propan-2-ol;
1-(4-(2,3-dichlorophenyl)piperazin-1-yl)-3-(9-phenyl-8-propyl-9H-purin-6-ylamino)propan-2-ol;
N-(3-(4-(2,3-dimethylphenyl)piperazin-1-yl)propyl)-9-methyl-8-phenyl-9H-purine-6-amine;
1-(4-(2,3-dimethylphenyl)piperazin-1-yl)-3-(9-methyl-8-phenyl-9H-purin-6-ylamino)propan-2-ol;
1-(4-(2,3-dimethylphenyl)piperazin-1-yl)-3-(9-phenyl-9H-purin-6-ylamino)propan-2-ol;
1-(4-(2,3-dimethylphenyl)piperazin-1-yl)-3-(8-ethyl-9-phenyl-9H-purin-6-ylamino)propan-2-ol;
1-(4-(2,3-dimethylphenyl)piperazin-1-yl)-3-(8,9-diphenyl-9H-purin-6-ylamino)propan-2-ol;
N-(3-(4-(2,3-dimethylphenyl)piperazin-1-yl)propyl)-8,9-dimethyl-9H-purine-6-amine;
N-(3-(4-(2,3-dimethylphenyl)piperazin-1-yl)propyl)-9-methyl-9H-purine-6-amine;
1-(4-(2,3-dimethylphenyl)piperazin-1-yl)-3-(9-methyl-9H-purin-6-ylamino)propan-2-ol;
9-tert-butyl-N-(3-(4-(2,3-dimethylphenyl)piperazin-1-yl)propyl)-9H-purine-6-amine;
1-(9-tert-butyl-9H-purin-6-ylamino)-3-(4-(2,3-dimethylphenyl)piperazin-1-yl)propan-2-ol;
1-(9-(benzo[d][1,3]dioxol-5-yl)-9H-purin-6-ylamino)-3-(4-(2,3-dimethylphenyl)piperazin-1-yl)propan-2-ol;
9-(benzo[d][1,3]dioxol-5-yl)-N-(3-(4-(2,3-dimethylphenyl)piperazin-1-yl)propyl)-9H-purine-6-amine;
1-(9-(benzo[d][1,3]dioxol-5-yl)-8-methyl-9H-purin-6-ylamino)-3-(4-(2,3-dimethylphenyl)piperazin-1-yl)propan-2-ol;
9-(benzo[d][1,3]dioxol-5-yl)-N-(3-(4-(2,3-dimethylphenyl)piperazin-1-yl)propyl)-8-methyl-9H-purine-6-amine;
8-tert-butyl-N-(3-(4-(2,3-dimethylphenyl)piperazin-1-yl)propyl)-9-methyl-9H-purine-6-amine;
1-(8-tert-butyl-9-methyl-9H-purin-6-ylamino)-3-(4-(2,3-dimethylphenyl)piperazin-1-yl)propan-2-ol;
9-(benzo[d][1,3]dioxol-5-yl)-N-(3-(4-(2,3-dimethylphenyl)piperazin-1-yl)propyl)-8-ethyl-9H-purine-6-amine;
1-(9-(benzo[d][1,3]dioxol-5-yl)-8-ethyl-9H-purin-6-ylamino)-3-(4-(2,3-dimethylphenyl)piperazin-1-yl)propan-2-ol;
9-(2,3-dihydrobenzo[b][1,4]dioxin-6-yl)-N-(3-(4-(2,3-dimethylphenyl)piperazin-1-yl)propyl)-9H-purine-6-amine;
1-(9-(2,3-dihydrobenzo[b][1,4]dioxin-6-yl)-9H-purin-6-ylamino)-3-(4-(2,3-dimethylphenyl)piperazin-1-yl)propan-2-ol;
9-(2,3-dihydrobenzo[b][1,4]dioxin-6-yl)-N-(3-(4-(2,3-dimethylphenyl)piperazin-1-yl)propyl)-8-methyl-9H-purine-6-amine;
1-(9-(2,3-dihydrobenzo[b][1,4]dioxin-6-yl)-8-methyl-9H-purin-6-ylamino)-3-(4-(2,3-dimethylphenyl)piperazin-1-yl)propan-2-ol;
9-(2,3-dihydrobenzo[b][1,4]dioxin-6-yl)-N-(3-(4-(2,3-dimethylphenyl)piperazin-1-yl)propyl)-8-ethyl-9H-purine-6-amine;
1-(9-(2,3-dihydrobenzo[b][1,4]dioxin-6-yl)-8-ethyl-9H-purin-6-ylamino)-3-(4-(2,3-dimethylphenyl)piperazin-1-yl)propan-2-ol;
N-(3-(4-(2,3-dimethylphenyl)piperazin-1-yl)propyl)-9-(4-fluorophenyl)-9H-purine-6-amine;
1-(4-(2,3-dimethylphenyl)piperazin-1-yl)-3-(9-(4-fluorophenyl)-9H-purin-6-ylamino)propan-2-ol;
N-(3-(4-(2,3-dimethylphenyl)piperazin-1-yl)propyl)-9-(4-fluorophenyl)-8-methyl-9H-purine-6-amine;
1-(4-(2,3-dimethylphenyl)piperazin-1-yl)-3-(9-(4-fluorophenyl)-8-methyl-9H-purin-6-ylamino)propan-2-ol;
N-(3-(4-(2,3-dimethylphenyl)piperazin-1-yl)propyl)-8-ethyl-9-(4-fluorophenyl)-9H-purine-6-amine;
1-(4-(2,3-dimethylphenyl)piperazin-1-yl)-3-(8-ethyl-9-(4-fluorophenyl)-9H-purin-6-ylamino)propan-2-ol;
8-tert-butyl-N-(3-(4-(2,3-dimethylphenyl)piperazin-1-yl)propyl)-9-phenyl-9H-purine-6-amine;
1-(8-tert-butyl-9-phenyl-9H-purin-6-ylamino)-3-(4-(2,3-dimethylphenyl)piperazin-1-yl)propan-2-ol;
N-(2-(4-(2,3-dimethylphenyl)piperazin-1-yl)ethyl)-9-(4-fluorophenyl)-8-methyl-9H-purine-6-amine;
N-(2-(4-(2,3-dimethylphenyl)piperazin-1-yl)ethyl)-8-ethyl-9-(4-fluorophenyl)-9H-purine-6-amine;
9-(benzo[d][1,3]dioxol-5-yl)-N-(2-(4-(2,3-dimethylphenyl)piperazin-1-yl)ethyl)-8-methyl-9H-purine-6-amine;
9-(benzo[d][1,3]dioxol-5-yl)-N-(2-(4-(2,3-dimethylphenyl)piperazin-1-yl)ethyl)-8-ethyl-9H-purine-6-amine;
9-(2,3-dihydrobenzo[b][1,4]dioxin-6-yl)-N-(2-(4-(2,3-dimethylphenyl)piperazin-1-yl)ethyl)-8-methyl-9H-purine-6-amine;
9-(2,3-dihydrobenzo[b][1,4]dioxin-6-yl)-N-(2-(4-(2,3-dimethylphenyl)piperazin-1-yl)ethyl)-8-ethyl-9H-purine-6-amine;
N-(2-(4-(2,3-dimethylphenyl)piperazin-1-yl)ethyl)-9-(4-methoxyphenyl)-8-methyl-9H-purine-6-amine;

N-(3-(4-(2,3-dimethylphenyl)piperazin-1-yl)propyl)-9-(4-methoxyphenyl)-8-methyl-9H-purine-6-amine;
1-(4-(2,3-dimethylphenyl)piperazin-1-yl)-3-(9-(4-methoxyphenyl)-8-methyl-9H-purin-6-ylamino)propan-2-ol;
N-(2-(4-(2,3-dimethylphenyl)piperazin-1-yl)ethyl)-8-ethyl-9-(4-methoxyphenyl)-9H-purine-6-amine;
N-(3-(4-(2,3-dimethylphenyl)piperazin-1-yl)propyl)-8-ethyl-9-(4-methoxyphenyl)-9H-purine-6-amine;
1-(4-(2,3-dimethylphenyl)piperazin-1-yl)-3-(8-ethyl-9-(4-methoxyphenyl)-9H-purin-6-ylamino)propan-2-ol;
N-(3-(4-(3-chloro-2-methylphenyl)piperazin-1-yl)propyl)-8,9-diphenyl-9H-purine-6-amine;
N-(4-(4-(2,3-dimethylphenyl)piperazin-1-yl)butyl)-8,9-diphenyl-9H-purine-6-amine;
9-(4-chlorophenyl)-N-(2-(4-(2,3-dimethylphenyl)piperazin-1-yl)ethyl)-8-methyl-9H-purine-6-amine;
9-(4-chlorophenyl)-N-(3-(4-(2,3-dimethylphenyl)piperazin-1-yl)propyl)-8-methyl-9H-purine-6-amine;
1-(9-(4-chlorophenyl)-8-methyl-9H-purin-6-ylamino)-3-(4-(2,3-dimethylphenyl)piperazin-1-yl)propan-2-ol;
9-(4-chlorophenyl)-N-(2-(4-(2,3-dimethylphenyl)piperazin-1-yl)ethyl)-8-ethyl-9H-purine-6-amine;
9-(4-chlorophenyl)-N-(3-(4-(2,3-dimethylphenyl)piperazin-1-yl)propyl)-8-ethyl-9H-purine-6-amine;
1-(9-(4-chlorophenyl)-8-ethyl-9H-purin-6-ylamino)-3-(4-(2,3-dimethylphenyl)piperazin-1-yl)propan-2-ol;
N-(2-(4-(2,3-dimethylphenyl)piperazin-1-yl)ethyl)-8-methyl-9-(4-(trifluoromethyl)phenyl)-9H-purine-6-amine;
N-(3-(4-(2,3-dimethylphenyl)piperazin-1-yl)propyl)-8-methyl-9-(4-(trifluoromethyl)phenyl)-9H-purine-6-amine;
N-(2-(4-(2,3-dimethylphenyl)piperazin-1-yl)ethyl)-8-ethyl-9-(4-(trifluoromethyl)phenyl)-9H-purine-6-amine;
N-(3-(4-(2,3-dimethylphenyl)piperazin-1-yl)propyl)-8-ethyl-9-(4-(trifluoromethyl)phenyl)-9H-purine-6-amine;
N-(3-(4-(2,3-dimethylphenyl)piperazin-1-yl)propyl)-9-(4-fluorophenyl)-8-phenyl-9H-purine-6-amine;
9-(4-chlorophenyl)-N-(3-(4-(2,3-dimethylphenyl)piperazin-1-yl)propyl)-8-phenyl-9H-purine-6-amine;
N-(3-(4-(2,3-dimethylphenyl)piperazin-1-yl)propyl)-9-(4-methoxyphenyl)-8-phenyl-9H-purine-6-amine;
N-(3-(4-(2,3-dimethylphenyl)piperazin-1-yl)propyl)-8-phenyl-9-(4-(trifluoromethyl)phenyl)-9H-purine-6-amine;
9-(benzo[d][1,3]dioxol-5-yl)-N-(3-(4-(2,3-dimethylphenyl)piperazin-1-yl)propyl)-8-phenyl-9H-purine-6-amine;
9-(2,3-dihydrobenzo[b][1,4]dioxin-6-yl)-N-(3-(4-(2,3-dimethylphenyl)piperazin-1-yl)propyl)-8-phenyl-9H-purine-6-amine;
N-(2-(4-(2,3-dimethylphenyl)piperazin-1-yl)ethyl)-8-methyl-9-(4-(methylthio)phenyl)-9H-purine-6-amine hydrochloride;
N-(3-(4-(2,3-dimethylphenyl)piperazin-1-yl)propyl)-8-methyl-9-(4-(methylthio)phenyl)-9H-purine-6-amine hydrochloride;
N-(2-(4-(2,3-dimethylphenyl)piperazin-1-yl)ethyl)-8-ethyl-9-(4-(methylthio)phenyl)-9H-purine-6-amine hydrochloride;
N-(3-(4-(2,3-dimethylphenyl)piperazin-1-yl)propyl)-8-ethyl-9-(4-(methylthio)phenyl)-9H-purine-6-amine hydrochloride;
N-(2-(4-(2,3-dimethylphenyl)piperazin-1-yl)ethyl)-9-(4-(methylthio)phenyl)-8-phenyl-9H-purine-6-amine hydrochloride;
N-(3-(4-(2,3-dimethylphenyl)piperazin-1-yl)propyl)-9-(4-(methylthio)phenyl)-8-phenyl-9H-purine-6-amine hydrochloride;
N-(2-(4-(2,3-dimethylphenyl)piperazin-1-yl)ethyl)-9-phenyl-8-(thiophen-2-yl)-9H-purine-6-amine hydrochloride;
N-(3-(4-(2,3-dimethylphenyl)piperazin-1-yl)propyl)-9-phenyl-8-(thiophen-2-yl)-9H-purine-6-amine hydrochloride;
8-cyclopentyl-N-(2-(4-(2,3-dimethylphenyl)piperazin-1-yl)ethyl)-9-phenyl-9H-purine-6-amine hydrochloride;
N-(2-(4-(2,3-dimethylphenyl)piperazin-1-yl)ethyl)-8-phenyl-9-propyl-9H-purine-6-amine hydrochloride;
N-(4-(4-(2,3-dimethylphenyl)piperazin-1-yl)butyl)-9-(4-methoxyphenyl)-8-phenyl-9H-purine-6-amine hydrochloride;
N-(4-(4-(2,3-dimethylphenyl)piperazin-1-yl)butyl)-9-(4-(methylthio)phenyl)-8-phenyl-9H-purine-6-amine hydrochloride;
N-(4-(4-(2,3-dimethylphenyl)piperazin-1-yl)butyl)-9-(4-fluorophenyl)-8-phenyl-9H-purine-6-amine hydrochloride;
9-(2,3-dihydrobenzo[b][1,4]dioxin-6-yl)-N-(4-(4-(2,3-dimethylphenyl)piperazin-1-yl)butyl)-8-phenyl-9H-purine-6-amine hydrochloride;
N-(4-(4-(2,3-dimethylphenyl)piperazin-1-yl)butyl)-8-phenyl-9-(4-(trifluoromethyl)phenyl)-9H-purine-6-amine hydrochloride;
N-(3-(4-(2,3-dimethylphenyl)piperazin-1-yl)propyl)-N-methyl-8,9-diphenyl-9H-purine-6-amine hydrochloride;
N-(3-(4-(3-chloro-2-methylphenyl)piperazin-1-yl)propyl)-N-methyl-8,9-diphenyl-9H-purine-6-amine hydrochloride;
N-(3-(4-(2,3-dichlorophenyl)piperazin-1-yl)propyl)-N-methyl-8,9-diphenyl-9H-purine-6-amine hydrochloride;
(S)-1-(4-(2,3-dimethylphenyl)piperazin-1-yl)-3-(8,9-diphenyl-9H-purin-6-ylamino)propan-2-ol hydrochloride;
(S)-1-(4-(3-chloro-2-methylphenyl)piperazin-1-yl)-3-(8,9-diphenyl-9H-purin-6-ylamino)propan-2-ol hydrochloride;
(S)-1-(4-(2,3-dichlorophenyl)piperazin-1-yl)-3-(8,9-diphenyl-9H-purin-6-ylamino)propan-2-ol hydrochloride;
(R)-1-(4-(2,3-dimethylphenyl)piperazin-1-yl)-3-(8,9-diphenyl-9H-purin-6-ylamino)propan-2-ol hydrochloride;
(R)-1-(4-(3-chloro-2-methylphenyl)piperazin-1-yl)-3-(8,9-diphenyl-9H-purin-6-ylamino)propan-2-ol hydrochloride;
(R)-1-(4-(2,3-dichlorophenyl)piperazin-1-yl)-3-(8,9-diphenyl-9H-purin-6-ylamino)propan-2-ol hydrochloride;
N-(4-(4-(2,3-dimethylphenyl)piperazin-1-yl)butyl)-9-phenyl-8-(thiophen-2-yl)-9H-purine-6-amine hydrochloride;
1-(4-(2,3-dimethylphenyl)piperazin-1-yl)-3-((8,9-diphenyl-9H-purin-6-yl)(methyl)amino)propan-2-ol hydrochloride;
1-(4-(3-chloro-2-methylphenyl)piperazin-1-yl)-3-((8,9-diphenyl-9H-purin-6-yl)(methyl)amino)propan-2-ol hydrochloride;
1-(4-(2,3-dichlorophenyl)piperazin-1-yl)-3-((8,9-diphenyl-9H-purin-6-yl)(methyl)amino)propan-2-ol hydrochloride;
N-(4-(4-(2,3-dimethylphenyl)piperazin-1-yl)butyl)-N-methyl-8,9-diphenyl-9H-purine-6-amine hydrochloride;
4-(4-(2,3-dimethylphenyl)piperazin-1-yl)-1-[8,9-d]phenyl-9H-purin-6-yl)(methyl)amino)butan-2-ol hydrochloride;
N-(4-(4-(2,3-dimethylphenyl)piperazin-1-yl)butyl)-N,2-dimethyl-8,9-diphenyl-9H-purine-6-amine hydrochloride;
N-(4-(4-(2,3-dimethylphenyl)-1,4-diazepan-1-yl)butyl)-8,9-diphenyl-9H-purine-6-amine hydrochloride;
N-(4-(4-(2,3-dimethylphenyl)-1,4-diazepan-1-yl)butyl)-2-methyl-8,9-diphenyl-9H-purine-6-amine hydrochloride;
N-(4-(4-(2,3-dimethylphenyl)-2-methylpiperazin-1-yl)butyl)-8,9-diphenyl-9H-purine-6-amine hydrochloride;
N-(4-(4-(2,3-dimethylphenyl)-2-methylpiperazin-1-yl)butyl)-2-methyl-8,9-diphenyl-9H-purine-6-amine hydrochloride;

4-(4-(2,3-dimethylphenyl)piperazin-1-yl)-1-(methyl(2-methyl-8,9-diphenyl-9H-purin-6-yl)amino)butan-2-ol hydrochloride;
4-(4-(2,3-dimethylphenyl)-1,4-diazepan-1-yl)-1-[8,9-d]phenyl-9H-purin-6-yl)(methyl)amino)butan-2-ol hydrochloride;
4-((R)-4-(2,3-dimethylphenyl)-2-methylpiperazin-1-yl)-1-[8,9-d]phenyl-9H-purin-6-yl)(methyl)amino)butan-2-ol hydrochloride;
4-((S)-4-(2,3-dimethylphenyl)-2-methylpiperazin-1-yl)-1-[8,9-d]phenyl-9H-purin-6-yl)(methyl)amino)butan-2-ol hydrochloride;
4-(4-(2,3-dimethylphenyl)-2-methylpiperazin-1-yl)-1-[8,9-d]phenyl-9H-purin-6-yl)(methyl)amino)butan-2-ol hydrochloride;
4-(4-(2,3-dimethylphenyl)piperazin-1-yl)-1-(8,9-diphenyl-9H-purin-6-ylamino)butan-2-ol hydrochloride;
1-(4-(2,3-dimethylphenyl)piperazin-1-yl)-4-(8,9-diphenyl-9H-purin-6-ylamino)butan-2-ol hydrochloride;
N-(4-(4-(2,3-dimethylphenyl)-2-methylpiperazin-1-yl)butyl)-N-methyl-8,9-diphenyl-9H-purine-6-amine hydrochloride;
N-(4-(4-(2,3-dimethylphenyl)-2-methylpiperazin-1-yl)butyl)-N,2-dimethyl-8,9-diphenyl-9H-purine-6-amine hydrochloride;
N-(4-(4-(2,3-dimethylphenyl)-1,4-diazepan-1-yl)butyl)-N-methyl-8,9-diphenyl-9H-purine-6-amine hydrochloride;
N-(4-(4-(2,3-dimethylphenyl)-1,4-diazepan-1-yl)butyl)-N,2-dimethyl-8,9-diphenyl-9H-purine-6-amine hydrochloride;
N-(4-(4-(2,3-dimethylphenyl)-2-methylpiperazin-1-yl)butyl)-N-ethyl-8,9-diphenyl-9H-purine-6-amine hydrochloride;
N-(4-(4-(2,3-dimethylphenyl)-2-methylpiperazin-1-yl)butyl)-N-ethyl-2-methyl-8,9-diphenyl-9H-purine-6-amine hydrochloride;
N-(4-(4-(2,3-dimethylphenyl)-1,4-diazepan-1-yl)butyl)-N-ethyl-8,9-diphenyl-9H-purine-6-amine hydrochloride;
N-(4-(4-(2,3-dimethylphenyl)-1,4-diazepan-1-yl)butyl)-N-ethyl-2-methyl-8,9-diphenyl-9H-purine-6-amine hydrochloride;
(S)—N-(4-(4-(2,3-dimethylphenyl)-2-methylpiperazin-1-yl)butyl)-8,9-diphenyl-9H-purine-6-amine hydrochloride;
(S)—N-(4-(4-(2,3-dimethylphenyl)-2-methylpiperazin-1-yl)butyl)-2-methyl-8,9-diphenyl-9H-purine-6-amine hydrochloride;
(R)—N-(4-(4-(2,3-dimethylphenyl)-2-methylpiperazin-1-yl)butyl)-8,9-diphenyl-9H-purine-6-amine hydrochloride;
(R)—N-(4-(4-(2,3-dimethylphenyl)-2-methylpiperazin-1-yl)butyl)-2-methyl-8,9-diphenyl-9H-purine-6-amine hydrochloride;
(S)—N-(4-(4-(2,3-dimethylphenyl)-2-methylpiperazin-1-yl)butyl)-N-methyl-8,9-diphenyl-9H-purine-6-amine hydrochloride;
(S)—N-(4-(4-(2,3-dimethylphenyl)-2-methylpiperazin-1-yl)butyl)-N,2-dimethyl-8,9-diphenyl-9H-purine-6-amine hydrochloride;
(R)—N-(4-(4-(2,3-dimethylphenyl)-2-methylpiperazin-1-yl)butyl)-N-methyl-8,9-diphenyl-9H-purine-6-amine hydrochloride;
(R)—N-(4-(4-(2,3-dimethylphenyl)-2-methylpiperazin-1-yl)butyl)-N,2-dimethyl-8,9-diphenyl-9H-purine-6-amine hydrochloride; and
N-(4-(4-(2,3-dimethylphenyl)piperazin-1-yl)butyl)-2-methyl-8,9-diphenyl-9H-purine-6-amine hydrochloride.

General Synthetic Sequence

The following synthetic schemes are merely illustrative of the methods by which the compounds of the invention may be prepared and are not intended to limit the scope of the invention as defined in the appended claims.

In accordance with another aspect of the present invention, there is provided a method for preparing the compound of formula (I) comprising the step of subjecting a compound of formula (II) to a reaction with a compound of formula (III):

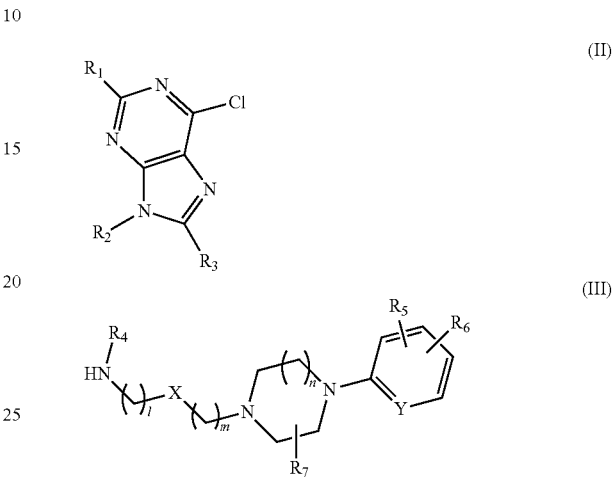

wherein, $R^1$ to $R^7$, X, Y, l, m and n have the same meanings as defined above.

In accordance with a further aspect of the present invention, there is provided a method for preparing the compound of formula (I) comprising the steps of:

subjecting a compound of formula (II) to a reaction with aminoalcohol to obtain a amination product:

conducting a oxidation of the amination product using Dess-Martin periodinane to obtain a ketone compound; and carrying out a reductive amination of the ketone compound with a compound of formula (IV) using a reducing agent:

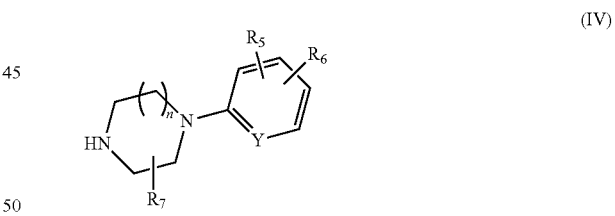

wherein, $R^5$ to $R^7$, Y and n have the same meanings as defined above.

As illustrated in Reaction Scheme 1, the purine derivatives (8) are prepared by a reaction of the conventional method (see [Pfizer Inc., U.S. Pat. No. 7,129,239 B2, 2006; and Griffith, D. A. et al., *J. Med. Chem.*, 52(2), 234-237 (2009)]), for example, reacting 4,6-dichloro-5-aminopyrimidine (1) with an aniline derivative (2) in refluxing aqueous hydrochloric acid to produce diaminopyrimidine (3) (67%). Subsequent acylation of the resulting diaminopyrimidine (3) with the appropriate benzoyl chlorides in dimethylamide (DMA) provides an intermediate benzamides (4) (88%), which are then cyclized to obtain purinones (5) (95%) by heating under an acidic condition. Heating purinones (5) in the presence of phosphorus oxychloride produce the corresponding chloropurines (6) (89%). Amine (7) readily reacts with chloropurines (6) in refluxing ethanol to generate the desired purine analogues (8) (56%).

<Reaction Scheme 1>

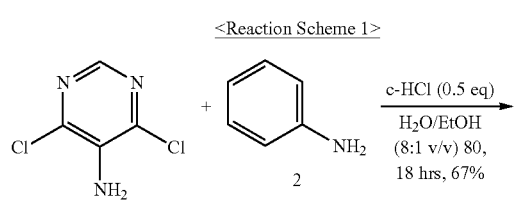

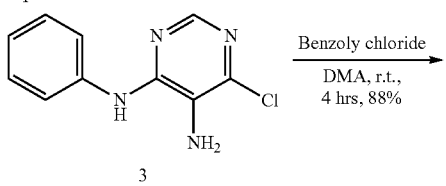

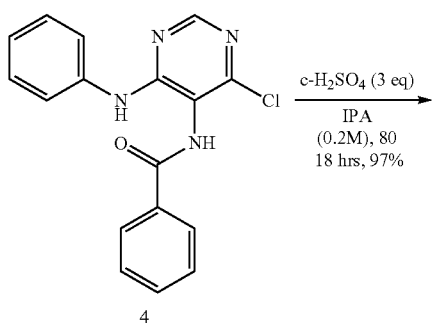

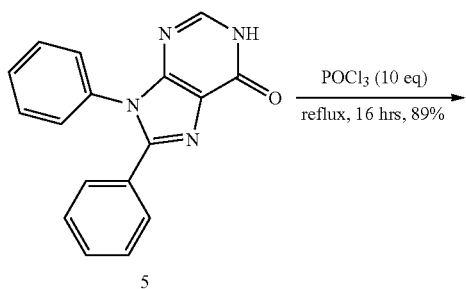

Alternatively, the purine derivatives (14) are prepared as shown in Reaction Scheme 2. The chloropurine (6) is subjected to react with 3-amino-1-propanol (9) in dioxane at room temperature (r.t.) to produce the amination product (10). Oxidation of therminal hydroxyl group to an aldehyde (11) using Dess-Martin periodinane should result in spontaneous equilibrium with cyclized compound (12) (see ([Bae, S. et al., *J. Org. Chem.*, 73, 1311-1319 (2008)]). Reductive amination of the particular compounds (11 and 12) with sodium triacetoxyborohydride produces the target purine derivative (14).

<Reaction Scheme 2>

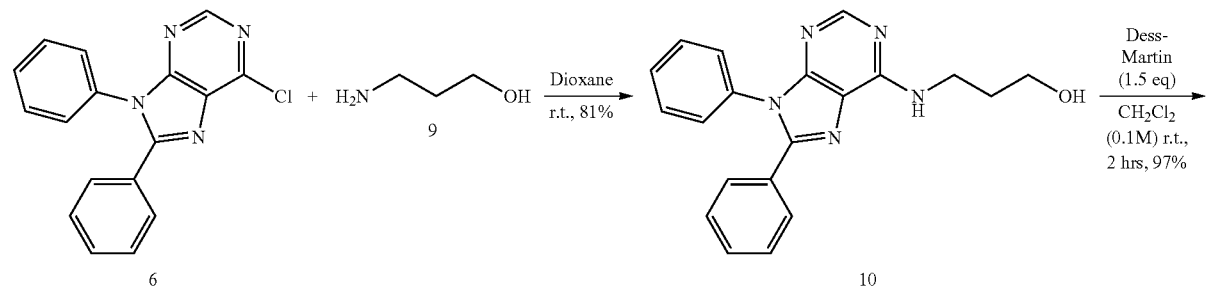

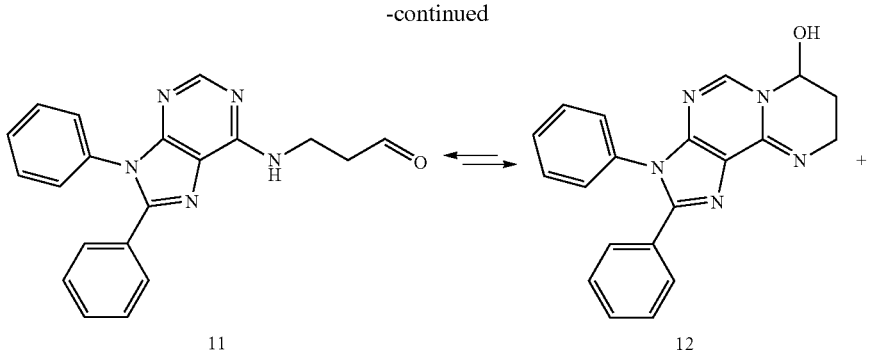

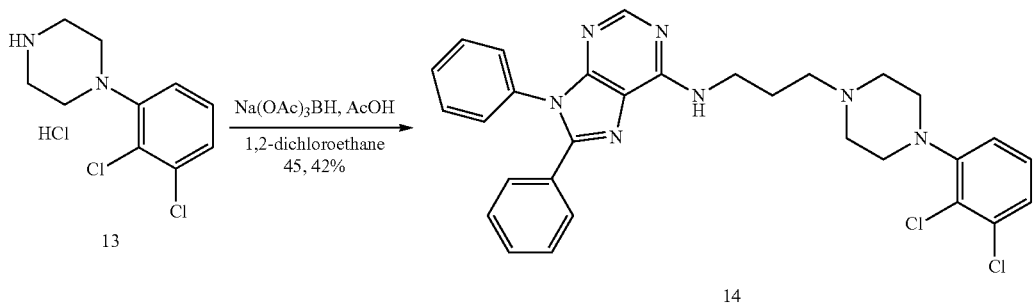

Another approach toward purine intermediate is described in Reaction Scheme 3. Reaction of 4-chloroaniline (15) with 4,6-dichloro-5-aminopyrimidine (1) in refluxing hydrochloric acid provides diaminopyrimidine (16). Condensation of diaminopyrimidine (16) with triethyl orthopropionate and ethanesulfonic acid provides the corresponding 6-chloropurine (17) (see [Kelly, J. L. et al., *J. Med. Chem.*, 40(20), 3207-3216 (1997)]).

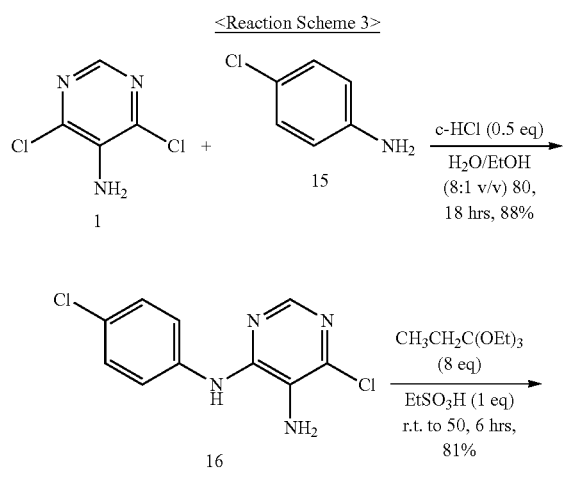

As shown in Reaction Scheme 4, the synthesis of 3-(4-(2,3-dichlorophenyl)piperazin-1-yl)propan-1-amine (20), and the like, wherein the alkyl chain between the piperazine and the terminal amine corresponds to 2 to 4 carbons, commenced with N-(2-bromoethyl)phthalimide, N-(3-bromopropyl)phthalimide (18), and N-(4-bromobutyl)phthalimide by adopting a reported procedure (see [Robarge, M. J., et al., *J. Med. Chem.*, 44, 3175-3186 (2001)]). For example, N-(3-bromopropyl)phthalimide (18) is reacted with 1-(2,3-dichlorophenyl)piperazine (13) in the presence of potassium carbonate in a suitable solvent such as N,N-dimethylformamide (DMF) at r.t. affords the corresponding alkylated product (19) in 80% yield. Hydrazinolysis of the alkylated product (19), followed by treatment of HCl solution generates 3-(4-(2,3-dichlorophenyl)piperazin-1-yl)propan-1-amine as a HCl salt form (20) in 76% yield.

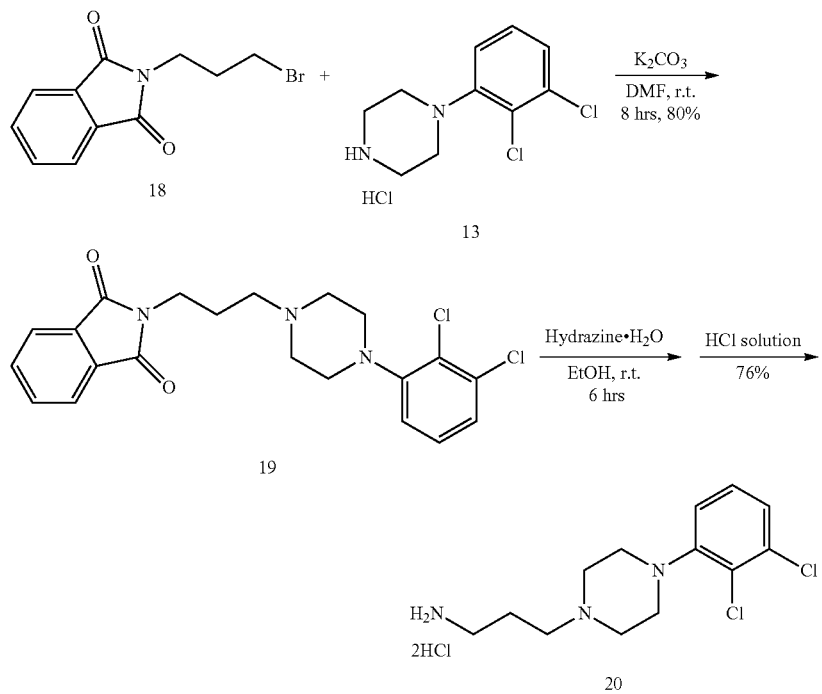

N-Arylpiperazines such as the compound (23) are prepared via condensation of the requisite anilines such as 3-chloro-2-methylaniline (22) with bis(2-chloroethyl)amine (21) or its hydrochloride following a reported procedure (see [Martin, G. E., et al., *J. Med. Chem.*, 32, 1052-1056 (1989)]) as shown in Reaction Scheme 5.

In order to increase hydrophilicity for compounds such as 3-(4-(2,3-dichlorophenyl)piperazin-1-yl)propan-1-amine (20), a compound such as 1-amino-3-(4-(2,3-dichlorophenyl)piperazin-1-yl)propan-2-ol (26) is prepared as shown in Reaction Scheme 6. Thus, commercially available N-(2,3-epoxypropyl)phthalimide (24) is treated with 1-(2,3-dichlorophenyl)piperazine (13) in the presence of base such as triethylamine in a suitable solvent such as tetrahydrofuran (THF) at 80° C. to produce the alcohol (25) in about 91% yield. Subsequently, hydrazinolysis of the alcohol (25) generates 1-amino-3-(4-(2,3-dichlorophenyl)piperazin-1-yl)propan-2-ol (26) as a white solid in 95% yield.

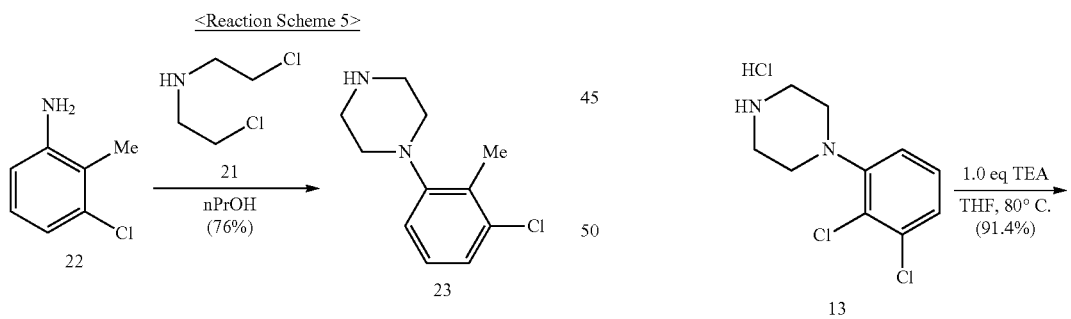

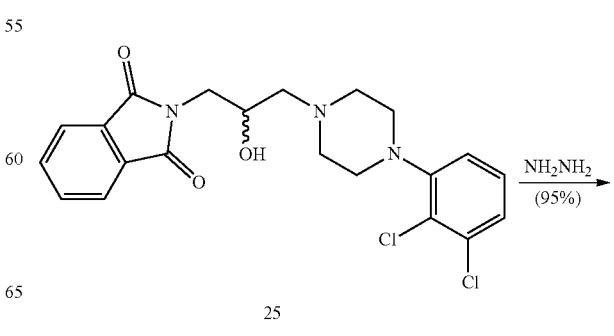

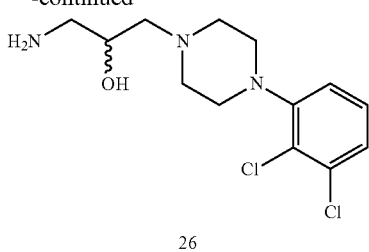

26

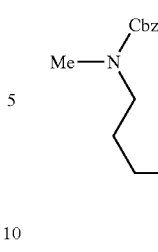

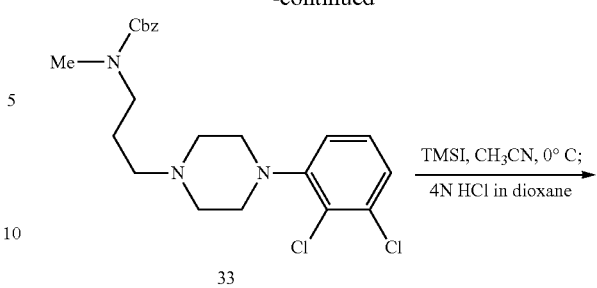

33

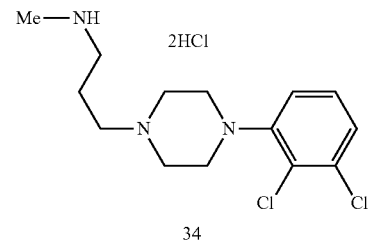

34

The requisite amine intermediate (34) is prepared as described in Reaction Scheme 7. Thus, 4-aminobutan-1-ol (27) is protected with CBzCl in the presence of a suitable base such as triethylamine. The corresponding compound (28) is silylated with tert-butyldimethylsilyl chloride (TBSCl) in the presence of imidazole to produce the compound (29). Methylation of the compound (29) is accomplished under the conditions of sodium hydride and iodomethane in a suitable solvent such as DMF. The alcohol is restored by treatment of tetra-n-butylammonium fluoride (TBAF) in a solvent involving THF at r.t. The alcohol (31) thus obtained is transformed into the corresponding bromide (32), which is treated with piperazine (13) to generate the compound (33). Removal of benzyloxycarbonyl (CBz) group of the compound (33) with a suitable reagent such as N-trimethylsilylimidazole (TMSI) in acetonitrile produced the key amine intermediate (34).

4-Amino-1-(4-(2,3-dimethylphenyl)piperazin-1-yl)butan-2-ol (41), another key intermediate, is also obtained by following the reaction sequence shown in Reaction Scheme 8. Thus, 2-(but-3-enyl)isoindoline-1,3-dione (37), which is obtained from treatment of phthalimide (35) with 4-bromobut-1-ene (36) in the presence of a suitable base such as potassium carbonate, is reacted with meta-chloroperoxybenzoic acid (mCPBA) to provide the corresponding epoxide (38). The ring opening of the epoxide (38) with piperazine (39) produces the phthalimide (40). The key intermediate (41) is then obtained by treating the phthalimide (40) with hydrazine in a suitable solvent such as EtOH at r.t.

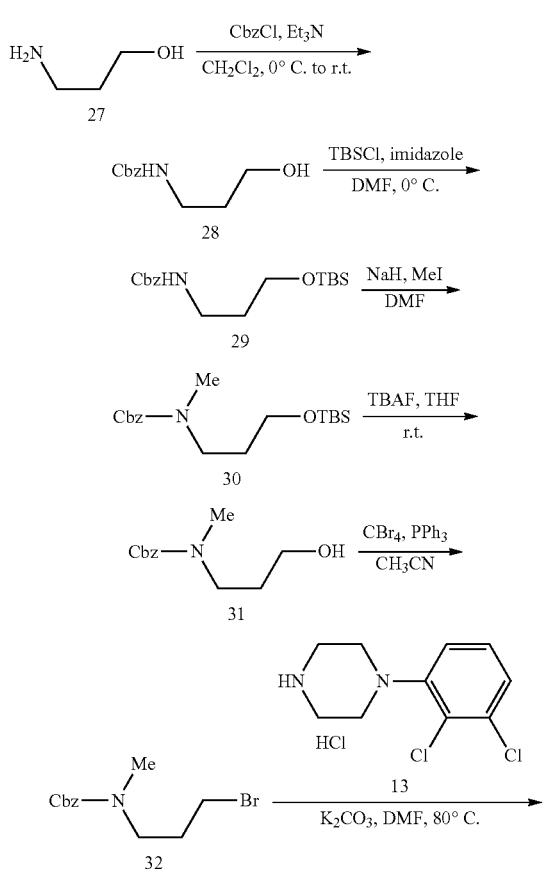

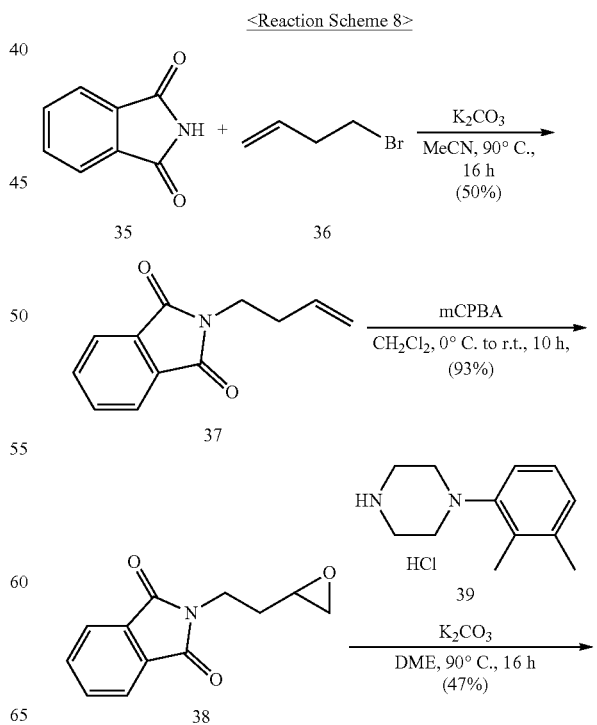

-continued

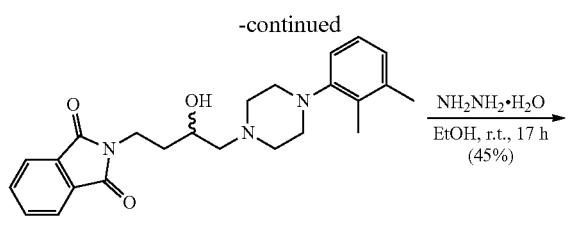
40

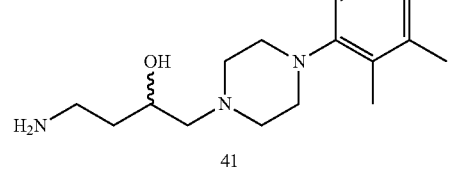
41

Another key amine intermediate (44) is obtained as shown in Reaction Scheme 9. Thus, 4-bromobut-1-ene (36) is oxidized by mCPBA in a suitable solvent such as methylene chloride to produce the epoxide (42). The epoxide (42) is treated with piperazine (39) in the presence of a suitable base such as potassium carbonate in a suitable solvent such as acetone to generate the epoxide (43). The ring opening reaction of the epoxide (43) with methylamine in a suitable solvent such as ethanol (EtOH) results in the key intermediate (44).

<Reaction Scheme 9>

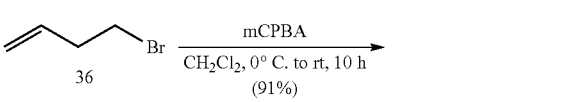

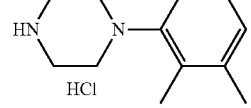
39

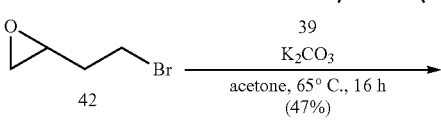

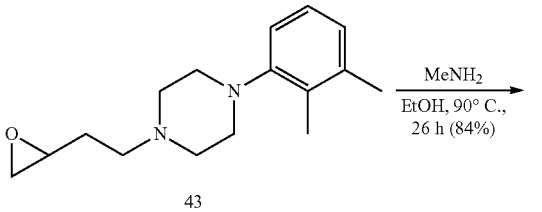
44

The piperazine derivatives are prepared as shown in Reaction Scheme 10. For example, methylpiperazine (45) is coupled with 1-bromo-2,3-dimethylbenzene (46) in the presence of palladium(II) acetate, 2,2'-bis(diphenylphosphino)-1,1'-binaphthyl (BINAP), and sodium tert-butoxide in refluxing toluene to generate the corresponding arylpiperazine (47) (see [Applied Research Systems, WO2006/67114 (2006)]. The other arylpiperazine derivatives (48 and 49) and diazepane (50) are prepared in an analogous fashion.

<Reaction Scheme 10>

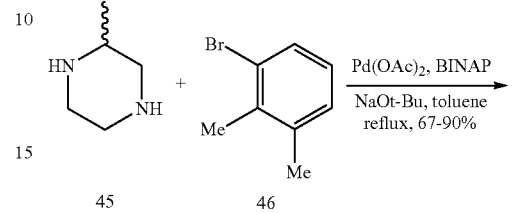
45      46

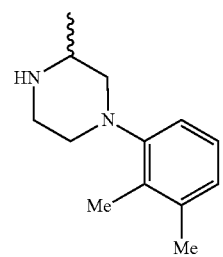
47

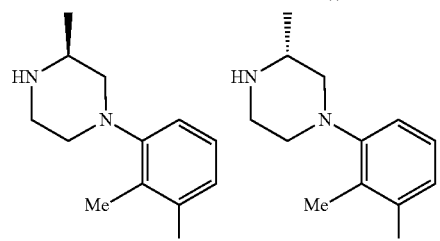
48      49

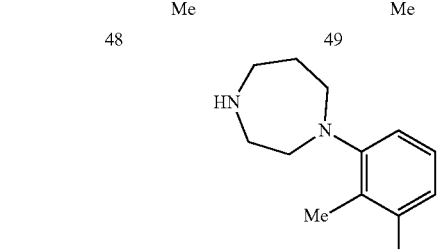
50

The inventive arylpiperazine-containing purine compound of formula (I) is effective for preventing or treating depressive disorders. When the inventive arylpiperazine-containing purine compound of formula (I) is used with a selective serotonine reuptake inhibitor, a serotonin and norepinephrine reuptake inhibitor or a mixture thereof, the inventive arylpiperazine-containing purine compound of formula (I) enhance the anti-depressant activities of the selective serotonine reuptake inhibitor, or the serotonin and norepinephrine reuptake inhibitor.

Accordingly, the present invention provides a use of the inventive arylpiperazine-containing purine compound of formula (I) for the manufacture of a medicament for preventing or treating depressive disorders.

Further, the present invention provides a use of the inventive arylpiperazine-containing purine compound of formula (I) for the manufacture of a medicament for enhancing the anti-depressant activities of a selective serotonine reuptake inhibitor, or a serotonin and norepinephrine reuptake inhibitor.

Further, the present invention provides a pharmaceutical composition for preventing or treating depressive disorders, which comprises the compound of formula (I) or a pharmaceutically acceptable salt or prodrug thereof as an active ingredient and a pharmaceutically acceptable carrier. The inventive pharmaceutical composition may further comprise the selective serotonine reuptake inhibitor, the serotonin and norepinephrine reuptake inhibitor or a mixture thereof.

Further, the present invention provides a method for preventing or treating depressive disorders in a mammal, which comprises administering the compound of formula (I) to the mammal in need thereof.

As used herein, the term "depressive disorders" refers to mental illnesses characterized by a profound and persistent feeling of sadness or despair and/or a loss of interest in things that once were pleasurable. Disturbance in sleep, appetite, and mental processes are a common accompaniment.

The pharmaceutical composition may be administered orally, intramuscularly or subcutaneously. The formulation for oral administration may take various forms such as a syrup, tablet, capsule, cream and lozenge. A syrup formulation will generally contain a suspension or solution of the compound or its salt in a liquid carrier, e.g., ethanol, peanut oil, olive oil, glycerin or water, optionally with a flavoring or coloring agent. When the composition is in the form of a tablet, any one of pharmaceutical carriers routinely used for preparing solid formulations may be used. Examples of such carriers include magnesium stearate, terra alba, talc, gelatin, acacia, stearic acid, starch, lactose and sucrose. When the composition is in the form of a capsule, any of the routine encapsulation procedures may be employed, e.g., using the aforementioned carriers in a hard gelatin capsule shell. When the composition is formulated in the form of a soft gelatin shell capsule, any of the pharmaceutical carrier routinely used for preparing dispersions or suspensions may be prepared using an aqueous gum, cellulose, silicate or oil. The formulation for intramuscular or subcutaneous administration may take a liquid form such as a solution, suspension and emulsion which includes aqueous solvents such as water, physiological saline and Ringer's solution; or lipophilic solvents such as fatty oil, sesame oil, corn oil and synthetic fatty acid ester.

Preferably the composition is formulated in a specific dosage form for a particular patient.

Each dosage unit for oral administration contains suitably from 0.1 mg to 500 mg/kg, and preferably from 1 mg to 100 mg/kg of the compound of Formula (I) or its pharmaceutically acceptable salt.

The suitable daily dosage for oral administration is about 0.01 mg/kg to 40 mg/kg of the compound of Formula (I) or pharmaceutically acceptable salt and prodrug thereof, may be administered 1 to 6 times a day, depending on the patient's condition.

SYNTHETIC EXAMPLES

As used herein the symbols and conventions used describing the processes, schemes and examples of the present invention are consistent with those used in the contemporary scientific literature, for example, the *Journal of the American Chemical Society or the Journal of Biological Chemistry*. Unless otherwise noted, all starting materials were obtained from commercial suppliers and used without further purification.

Hz (Hertz)
$T_r$ (retention time)
MeOH (methanol)
TFA (trifluoroacetic acid)
EtOH (ethanol)
DMSO (dimethylsulfoxide)
DCM (dichloromethane)
DMF (N,N-dimethylformamide)
CDI (1,1-carbonyldiimidazole)
HOSu (N-hydroxysuccinimide)
Boc (tert-butyloxycarbonyl)
mCPBA (meta-chloroperoxybenzoic acid)
FMOC (9-fluorenylmethoxycarbonyl)
DCC (dicyclohexylcarbodiimide)
Cbz (benzyloxycarbonyl)
NMM (N-methyl morpholine)
HOAt (1-hydroxy-7-azabenzotriazole)
TBAF (tetra-n-butylammonium fluoride)
THP (tetrahydro-2H-pyran-2-yl)
DMAP (4-dimethylaminopyridine)
HPLC (high pressure liquid chromatography)
BOP (bis(2-oxo-3-oxazolidinyl)-phosphinic chloride);
EDCI (1-ethyl-3-[3-dimethylamino-propyl]carbodiimide hydrochloride)
HBTU (O-Benzotriazole-1-yl-N,N,N',N'-tetramethyluronium hexafluorophosphate)
AIBN (2,2'-azobis(2-methylpropionitrile))
MeI (iodomethane)
LDA (lithium diisopropylamide)
DIPEA (diisopropylethylamine)
NaSMe (sodium thiomethoxide)
NaHMDS (bis(trimethylsilyl)amide)
DAST (diethylaminosulfur trifluoride)
HMDS (hexamethyldisilazane)
BINAP (2,2'-bis(diphenylphosphino)-1,1'-binaphthyl)
TLC(thin layer chromatography)
RP (reverse phase)
i-PrOH (isopropanol)
TEA (triethylamine)
THF (tetrahydrofuran)
EtOAc (ethyl acetate)
HOAc (acetic acid)
Ac (acetyl)
Bn (benzyl)
HOBT (1-hydroxybenzotriazole)

While the invention has been described with respect to the specific embodiments, it should be recognized that various modifications and changes may be made by those skilled in the art to the invention which also falls within the scope of the invention as defined as the appended claims.

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted, and all solvents are of the highest available purity unless otherwise indicated.

Microwave reaction was conducted with a Biotage Initiator™ microwave synthesizer.

$^1$H NMR spectra were recorded on either a Jeol ECX-400, or a Jeol JNM-LA300 spectrometer. Chemical shifts were expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

Mass spectra were obtained with Micromass, Quattro LC Triple Quadruple Tandem Mass Spectrometer, ESI or Agilent, 1100LC/MSD, ESI.

For preparative HPLC, ca 100 mg of a product was injected in 1 mL of DMSO onto a SunFire™ Prep C18 OBD 5 μm 19×100 mm Column with a 10 min gradient from 10% CH$_3$CN to 90% CH$_3$CN in H$_2$O (purification systems from Gilson, Inc). Flash chromatography was carried using Merck silica gel 60 (230 to 400 mesh). Biotage SP1™ FLASH Purification System and Biotage Isolera™ FLASH Purifica- Preparation Example 1

Preparation of
2-(4-(2,3-dichlorophenyl)piperazin-1-yl)ethanamine
dihydrochloride

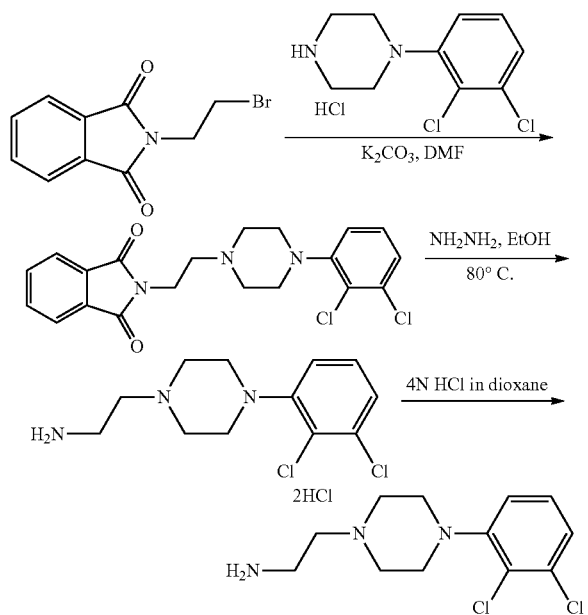

Step 1: 2-(2-(4-(2,3-dichlorophenyl)piperazin-1-yl)ethyl)isoindoline-1,3-dione 1-(2,3-Dichlorophenyl)piperazine hydrochloride (3.16 g, 11.8 mmol) and potassium carbonate (4.08 g, 29.5 mmol) were added to the solution of 2-(2-bromoethyl)isoindoline-1,3-dione (3 g, 11.8 mmol) in DMF (20 ml). The resulting reaction mixture was stirred for overnight at room temperature. After reaction complete, water (40 ml) was added thereto and then normal work-up was taken. The residue thus obtained was purified with normal phase preparative column to afford the title compound (3.87 g, 81% yield) as white solid.
MH+ 404.

Step 2:
2-(4-(2,3-dichlorophenyl)piperazin-1-yl)ethanamine dihydrochloride

To a stirred solution of 2-(2-(4-(2,3-dichlorophenyl)piperazin-1-yl)ethyl)isoindoline-1,3-dione (3.87 g, 9.57 mmol) in ethanol (50 ml) was added hydrazine (3 ml) at room temperature. The resulting reaction mixture was warmed to 80° C. and stirred for 1 day at that temperature. The resulting solution was cooled down to room temperature, and the volatiles were evaporated under reduced pressure. The residue was work-up with EtOAC and saturated sodium bicarbonate solution. After evaporation of organic layer under reduced pressure, it was poured into 1N HCl solution. The aqueous solution thus obtained was washed with ethyl ether, and then basified with aqueous ammonia. Methylene chloride was used for work-up organic layer, dried with magnesium sulfate. After solvent was removed under reduced pressure, 4N HCl in dioxane (5 ml) was added to the resulting compound, 2-(4-(2,3-dichlorophenyl)piperazin-1-yl)ethanamine at 0° C. and stirred 10 min to produce HCl salt form. Light yellow solid title compound (3.1 g, 89%) was obtained by evaporation and drying in vacuo volatile compounds.
MH+ 274(−2HCl)

Preparation Example 2

Preparation of
1-(3-chloro-2-methylphenyl)piperazine (compound (23))

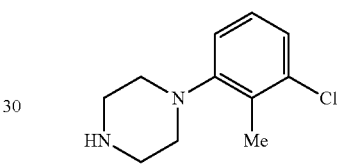

To a stirred solution of 3-chloro-2-methylaniline (21.6 g, 0.15 mol) in n-butanol (200 ml) was added bis(2-chloroethyl)amine hydrochloride (30 g, 0.17 mol) at room temperature and allowed to refluxed temperature for 2 days. After cooled to room temperature Na$_2$CO$_3$ (9 g, 0.08 mol) was added and then reaction mixture was refluxed 30 min. The resulting mixture was filtered with n-butanol (100 ml) and collected solid was dried under reduced pressure to be obtained title compound (24.8 g, 81%) as white solid.
MH+ 211.

Preparation Example 3

Preparation of 1-Amino-3-(4-(2,3-dichlorophenyl)piperazin-1-yl)propan-2-ol (compound (26))

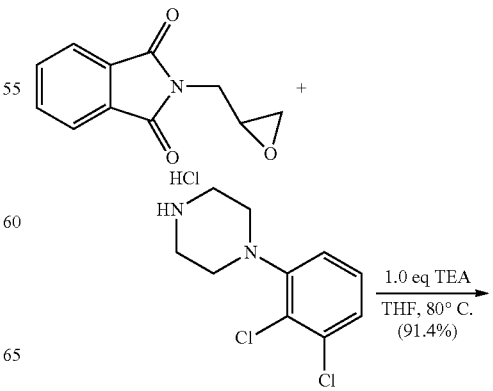

-continued

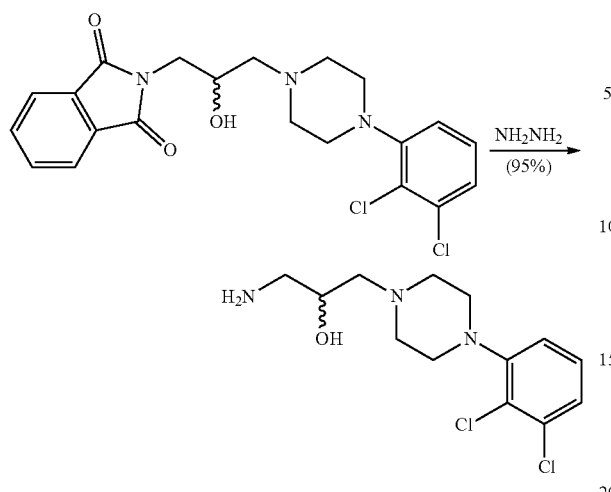

To a stirred solution of N-(2,3-epoxypropyl)phthalimide (10 g, 0.049 mol) in THF (100 mL) was added 1-(2,3-dichlorophenyl)piperazine HCl (8.7 g, 0.033 mol) and triethylamine (4.6 mL, 0.033 mol) at r.t., and then the resultant solution was heated at 80° C. overnight. The reaction was quenched with H$_2$O and extracted with DCM. The organic layer thus separated was washed with brine, dried over MgSO$_4$, filtered, and evaporated. The solid residue was solidified with DCM (20 mL)/diethyl ether (200 mL), filtered and dried in vacuo, which was used for the following synthesis without further purification. To the prepared white solid piperazine (13 g, 0.030 mol) in EtOH was added hydrazine monohydrate (20 mL) and the reaction solution was refluxed at 80° C. for 2 h. The reaction solution was cooled to r.t. and evaporated. The oily crude compound was extracted with EtOAc/H$_2$O and organic layer was combined and evaporated. The pale yellow solid was tritylated with ether to afford pure targeted amine (8.7 g, 95%) as white solid.

MH+ 304.

Preparation Example 4

Preparation of 3-(4-(2,3-dichlorophenyl)piperazin-1-yl)-N-methylpropan-1-amine dihydrochloride (compound (34))

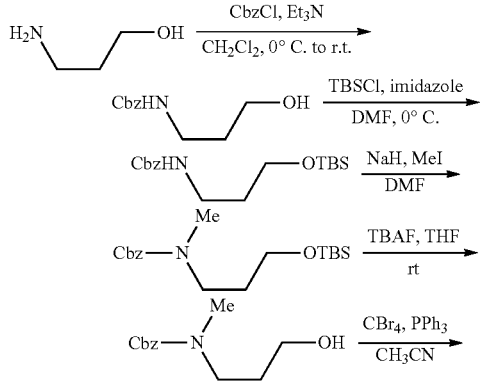

-continued

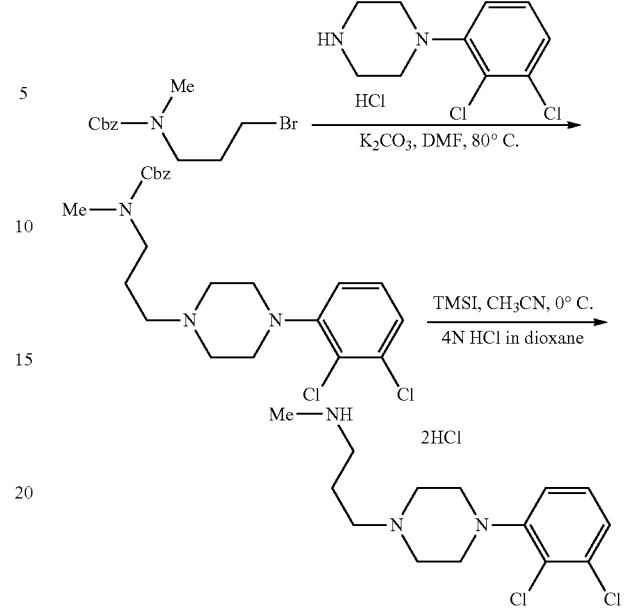

Step 1: Benzyl 3-hydroxypropylcarbamate (compound (28))

3-Aminopropan-1-ol (10 g, 133 mmol) was dissolved in methylene chloride (100 ml) at 0° C. Triethylamine (9 ml, 65 mmol) and CbzCl (10 ml, 66.8 mmol) were added slowly to the resulting solution at 0° C. and warmed to room temperature. The reaction mixture thus obtained was stirred for 1 hour at room temperature, and then diethyl ether (100 ml) and water (50 ml) were poured into the resulting solution. With diethyl ether normal work-up was taken, dried with magnesium sulfate. After evaporation the volatile material, the residue was purified with normal phase preparative column to produce the title compound (15 g, 95%) as colorless oil.

$^1$H NMR (400 MHz, CDCl$_3$) δ 7.35-7.27 (m, 5H), 5.27 (br.s, 1H), 5.09 (s, 2H), 3.71 (t, J=5.6 Hz, 2H), 3.32 (q, J=6 Hz, 2H), 1.74-1.69 (m, 2H).

MH+ 210

Step 2: Benzyl 3-(tert-butyldimethylsilyloxy)propylcarbamate (compound (29))

Benzyl 3-hydroxypropylcarbamate obtained in step 1 (15 g, 72 mmol) was treated with imidazole (10 g, 146.9 mmol) and TBSCl (12 g, 79.6 mmol) in DMF (10 ml) at 0° C. After warming up the resulting reaction mixture to room temperature, it was stirred for 30 minutes. The resulting solution was quenched with water (50 ml), and then extracted with diethyl ether twice (50 ml×2). After evaporation of volatile material under reduced pressure, the residue was purified with silica gel column chromatography (EtOAc:Hx=1:10) to afford the title compound (23 g, 98%) as colorless oil.

MH+ 324

Step 3: Benzyl 3-(tert-butyldimethylsilyloxy)propyl (methyl)carbamate (compound (30))

To the solution of benzyl 3-(tert-butyldimethylsilyloxy) propylcarbamate obtained in step 2 (5 g, 15.5 mmol) in tetrahydrofuran (20 ml), sodium hydride (1.24 g, 31 mmol, 60% in mineral oil) and iodomethane (3.86 ml, 62 mmol) were added slowly. The reaction temperature was warmed up to room temperature, and stirred for overnight. The reaction was completed quenched by water and organic material was extracted with ether. After evaporation of volatile material under reduced pressure, the residue was purified with silica gel column chromatography (EtOAC:Hx=1:10) to give the title compound (4.9 g, 94%) as light yellow oil.
MH+ 338

Step 4: Benzyl 3-bromopropyl(methyl)carbamate (compound (32))

TBAF (12.8 ml, 1.0 M solution in THF, 12.8 mmol) was added to the solution of benzyl 3-(tert-butyldimethylsilyloxy) propyl(methyl)carbamate obtained in step 3 (3.6 g, 10.7 mmol) in THF (30 ml). After reaction complete, water and EtOAC work-up and then drying were followed to give benzyl 3-hydroxypropyl(methyl)carbamate (formula 31). After further purification, alcohol was treated with triphenylphosphine (3.35 g, 12.8 mmol) and carbon tetrabromide (12.8 mmol) in acetonitrile (20 ml). The reaction progress was monitored by TLC or LS/MS. After reaction complete, the organic layer was extracted and evaporated. The residue was purified with silica gel column chromatography (EtOAC: Hx=1:5) to give the title compound (2.5 g, 82%, 2 steps) as light yellow oil.

Step 5: 3-(4-(2,3-dichlorophenyl)piperazin-1-yl)-N-methylpropan-1-amine dihydrochloride (compound (34))

Benzyl 3-bromopropyl(methyl)carbamate obtained in step 4 was converted to title compound in accordance with the method described at the preparation of 2-(4-(2,3-dichlorophenyl)piperazin-1-yl)ethanamine dihydrochloride of step 2 in Example 1.

Preparation Example 5

Preparation of 4-amino-1-(4-(2,3-dimethylphenyl) piperazin-1-yl)butan-2-ol (compound (41))

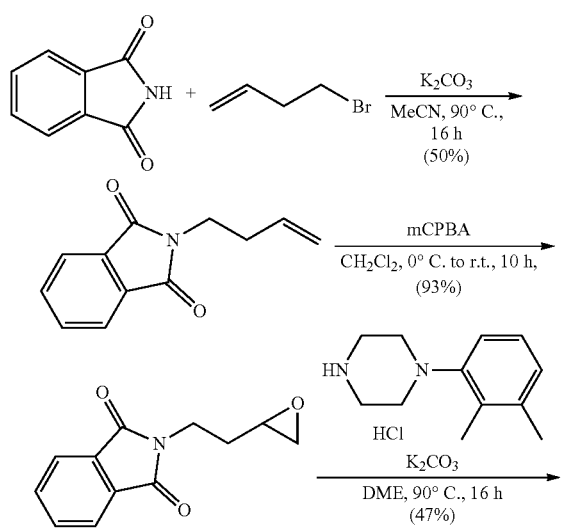

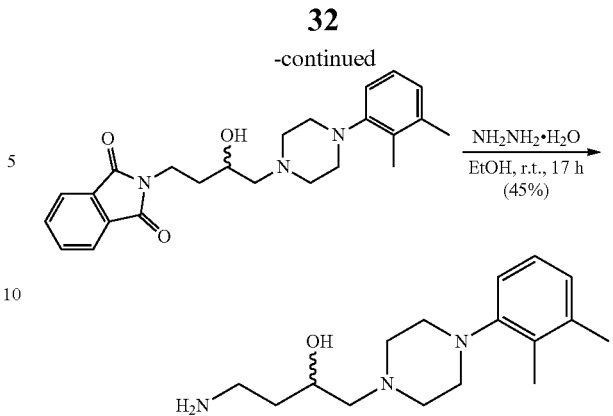

Step 1: 2-(but-3-en-1-yl)isoindoline-1,3-dione (compound (37))

To a mixture of phthalimide (3.92 g, 26.6 mmol) and potassium carbonate (9.20 g, 66.6 mmol) in acetonitrile (44 ml), was added 4-bromo-1-butene (2.26 ml, 22.2 mmol) at room temperature. The resulting reaction mixture was stirred at 90° C. for 13 hours. After the reaction complete, the reaction mixture thus obtained was filtered through a plug of Celite. The filtrate was concentrated under reduced pressure to obtain the title compound (2.23 g). The compound was used for the next step without further purification.
MH+ 202.

Step 2: 2-(2-(oxiran-2-yl)ethyl)isoindoline-1,3-dione (compound (38))

To a mixture of 2-(but-3-en-1-yl)isoindoline-1,3-dione obtained in step 1 (0.65 g, 3.22 mmol) in dichloromethane (10 ml), was added m-chloroperoxybenzoic acid (1.11 g, 6.44 mmol) at 0° C. The resulting reaction mixture was stirred at room temperature for 10 hours. After the reaction complete, the reaction mixture thus obtained was filtered through a plug of Celite. The filtrate was washed with 1 N sodium hydroxide solution and brine. The organic phase thus separated was dried over anhydrous magnesium sulfate, filtered, and concentrated under reduced pressure to obtain the title compound (0.65 g). The compound was used for the next step without further purification.
MH+ 218.

Step 3: 2-(4-(4-(2,3-dimethylphenyl)piperazin-1-yl)-3-hydroxybutyl)isoindoline-1,3-dione (compound (40))

To a mixture of 2-(2-(oxiran-2-yl)ethyl)isoindoline-1,3-dione obtained in step 2 (0.30 g, 1.38 mmol) and potassium carbonate (0.48 g, 3.45 mmol) in N,N-dimethylformamide (3.0 ml), was added 1-(2,3-dimethylphenyl)piperazine hydrochloride (0.31 g, 1.38 mmol) at room temperature. The resulting reaction mixture was stirred at 110° C. for 18 hours. After the reaction complete, the reaction mixture thus obtained was filtered through a plug of Celite. The filtrate was concentrated under reduced pressure to obtain the title compound (0.26 g). The compound was used for the next step without further purification.
MH+ 408.

Step 4: 4-amino-1-(4-(2,3-dimethylphenyl)piperazin-1-yl)butan-2-ol (compound (41))

To a mixture of 2-(4-(4-(2,3-dimethylphenyl)piperazin-1-yl)-3-hydroxybutyl)isoindoline-1,3-dione obtained in step 4

(0.26 g, 0.65 mmol) in ethanol (1.5 ml), was added hydrazine monohydrate (0.063 ml, 2.02 mmol) at room temperature. The resulting reaction mixture was stirred at room temperature for 17 hours. After the reaction complete, the reaction mixture thus obtained was sonicated and filtered. The filtrate was concentrated under reduced pressure. The residue was extracted with ethyl acetate and water. The organic phase thus separated was dried over anhydrous magnesium sulfate, filtered, and concentrated under reduced pressure to obtain the title compound (0.1 g). The compound was used for the next step without further purification.

MH+ 278.

Preparation Example 6

Preparation of N-arylpiperazine (Compound (44))

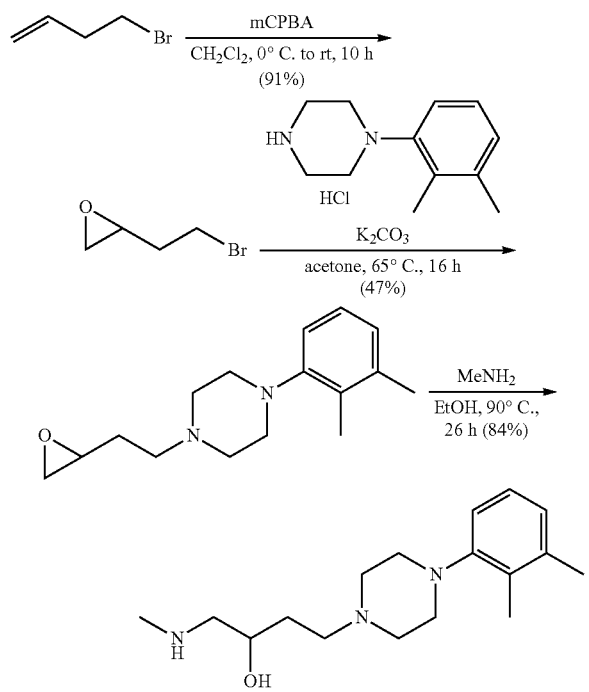

Step 1: 2-(2-bromoethyl)oxirane (compound (42))

To a mixture of 4-bromo-1-butene (3.76 ml, 37.0 mmol) in dichloromethane (80 ml), was added m-chloroperoxybenzoic acid (10.9 g, 63.0 mmol) at 0° C. The resulting reaction mixture was stirred at room temperature for 10 hours. After the reaction complete, the reaction mixture was filtered through a plug of Celite. The filtrate was washed with 1 N sodium hydroxide solution and brine. The organic phase thus separated was dried over anhydrous magnesium sulfate, filtered, and concentrated under reduced pressure to obtain the title compound (5.1 g). The compound was used for the next step without further purification.

$^1$H NMR (400 MHz, CDCl$_3$) δ 3.49 (t, J=7.2 Hz, 2H), 3.06 (m, 1H), 2.81 (m, 1H), 2.55 (m, 1H), 2.13 (m, 1H), 2.05 (m, 1H)

Step 2: 1-(2,3-dimethylphenyl)-4-(2-(oxiran-2-yl)ethyl)piperazine (compound (43))

To a mixture of 2-(2-bromoethyl)oxirane obtained in step 1 (0.70 g, 4.61 mmol) and potassium carbonate (1.91 g, 13.8 mmol) in acetone (10 ml), was added 1-(2,3-dimethylphenyl)piperazine hydrochloride (1.04 g, 4.61 mmol) at room temperature. The resulting reaction mixture was stirred at 65° C. for 16 hours. After the reaction complete, the reaction mixture thus obtained was filtered through a plug of Celite. The filtrate was concentrated under reduced pressure to obtain the title compound (0.31 g). The compound was used for the next step without further purification.

MH+ 261.

Step 3: 4-(4-(2,3-dimethylphenyl)piperazin-1-yl)-1-(methylamino)butan-2-ol (compound (44))

A mixture of 1-(2,3-dimethylphenyl)-4-(2-(oxiran-2-yl)ethyl)piperazine obtained in step 2 (0.10 g, 0.38 mmol) and methylamine (8.0 M) in ethanol (1.0 ml) was stirred at 90° C. for 20 hours. After the reaction complete, the resulting reaction mixture was concentrated under reduced pressure to obtain the title compound (0.10 g). The compound was used for the next step without further purification.

MH+ 292.

Preparation Example 7

Preparation of 1-(2,3-dimethylphenyl)-3-methylpiperazine (compound (47))

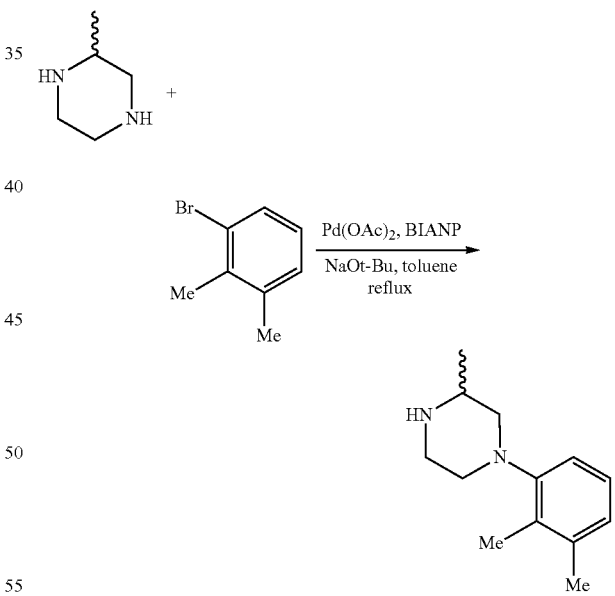

650 mg (6.48 mmol) of 2-methylpiperazine, 800 mg (4.32 mmol) of 3-bromo-o-xylene, 50 mg (0.22 mmol) of palladium acetate, 110 mg (0.17 mmol) of BINAP and 830 mg (8.65 mmol) of sodium tert-butoxide in dry toluene (8.6 mL) were heated at 110° C. for 14 hours. After cooling, the resulting reaction mixture was quenched with water and extracted with ethyl acetate. The ethyl acetate phase was concentrated. The residue was purified by chromatography to give the title compound as a yellow semi solid.

MH+ 204.

Preparation Example 8

Preparation of 6-chloro-9-(4-chlorophenyl)-8-ethyl-9H-purine (compound (17))

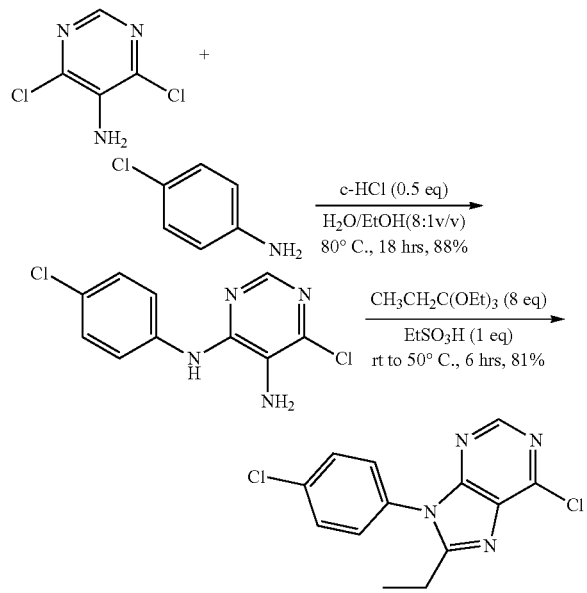

Step 1: 6-chloro-N4-(4-chlorophenyl)pyrimidine-4,5-diamine (compound (16))

5-amino-4,6-dichloropyrimidine (5.0 g, 30.49 mmol) and 4-chloroaniline (5.1 g, 40.0 mmol) were added to the solution of hydrochloric acid (1.3 mL, 15.24 mmol) in EtOH/$H_2O$ (8:1 v/v) (100 ml). The resulting reaction mixture was stirred for overnight at 80° C. The resulting mixture was filtered with $NaHCO_3$(aq)/$H_2O$. The collected solid was dried under reduced pressure to obtain the title compound (6.8 g, 88%) as white solid.

$^1$H NMR (400 MHz, DMSO-$d_6$) δ 8.66 (s, 1H), 7.85 (s, 1H), 7.70 (dd, J=6.8, 2.0 Hz, 2H), 7.33 (dd, J=6.8, 2.0 Hz, 2H), 5.43 (br.s, 2H).

MH+ 255.

Step 2: 6-chloro-9-(4-chlorophenyl)-8-ethyl-9H-purine (compound (17))

6-chloro-N4-(4-chlorophenyl)pyrimidine-4,5-diamine obtained in step 1 (1.5 g, 5.88 mmol) was dissolved in triethyl ortho propionate (11.8 ml, 58.8 mmol) at room temperature. Ethanesulfonic acid (0.48 mL, 5.88 mmol) was added slowly to the resulting solution at 0 r and warmed to room temperature. The reaction mixture thus obtained was stirred for 6 hours at 50° C. The resulting mixture was filtered with $NaHCO_3$(aq)/$H_2O$. The collected solid was dried under reduced pressure to obtain the title compound (1.39 g, 81%) as white solid.

$^1$H NMR (400 MHz, DMSO-$d_6$) δ 8.62 (s, 1H), 7.71-7.67 (m, 2H), 7.64-7.61 (m, 2H), 2.77 (q, J=7.6 Hz, 2H), 1.23 (t, J=7.2 Hz, 3H).

MH+ 293.

Preparation Example 9

Preparation of 6-chloro-8,9-diphenyl-9H-purine (compound (6))

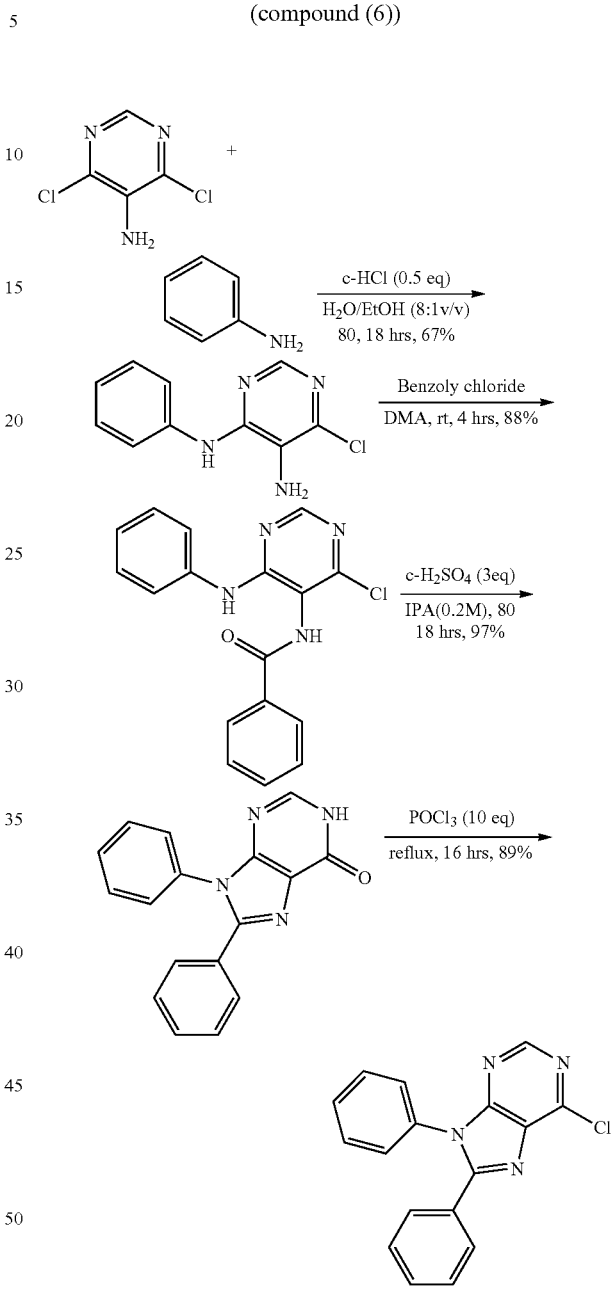

Step 1: 6-chloro-N4-phenylpyrimidine-4,5-diamine (compound (3))

5-amino-4,6-dichloropyrimidine (30 g, 183 mmol) and aniline (21.7 mL, 238 mmol) were added to the solution of hydrochloric acid (8 mL, 91.5 mmol) in EtOH/$H_2O$ (8:1 v/v) (600 ml). The resulting reaction mixture was stirred for overnight at 80° C. and filtered with $NaHCO_3$(aq)/$H_2O$. The collected solid was dried under reduced pressure to obtain the title compound (35.8 g, 89%) as white solid.

¹H NMR (400 MHz, DMSO-d₆) δ 8.54 (s, 1H), 7.82 (s, 1H), 7.65 (dd, J=8.8, 1.2 Hz, 2H), 7.28 (t, J=7.6 Hz, 2H), 6.99 (t, J=7.6 Hz, 1H), 5.40 (br.s, 2H). MH+ 221.

Step 2: N-(4-chloro-6-(phenylamino)pyrimidin-5-yl) benzamide (compound (4))

6-chloro-N4-phenylpyrimidine-4,5-diamine obtained in step 1 (35 g, 158.6 mmol) was dissolved in N,N-dimethylacetamide (265 ml) at 0° C. Benzoyl chloride (20.5 mL, 174.5 mmol) was added slowly to the resulting solution at 0° C. and warmed to room temperature. The reaction mixture thus obtained was stirred for 4 hours at room temperature and filtered with NaHCO₃(aq)/H₂O. The collected solid was dried under reduced pressure to obtain the title compound (50.1 g, 97%) as white solid.
¹H NMR (400 MHz, DMSO-d₆) δ 9.94 (s, 1H), 9.29 (s, 1H), 8.33 (s, 1H), 8.03 (d, J=6.8 Hz, 2H), 7.61-7.50 (m, 5H), 7.31 (t, J=7.6 Hz, 2H), 7.07 (t, J=7.2 Hz, 1H). MH+ 325.

Step 3: 8,9-diphenyl-1H-purin-6(9H)-one (compound (5))

To a stirred solution of N-(4-chloro-6-(phenylamino)pyrimidin-5-yl)benzamide obtained in step 2 (35 g, 108 mmol) in 2-propanol (360 mL) was added sulfuric acid (18.2 mL, 323.3 mmol) at 0° C. The reaction mixture was heated to reflux at 90° C. overnight. After cooled to room temperature NaHCO₃ (aq) was added to the resulting reaction mixture and stirred. The resulting mixture was filtered with water (600 mL). The collected solid was dried under reduced pressure to obtain the title compound (22.3 g, 72%) as white solid.
¹H NMR (400 MHz, DMSO-d₆) δ 12.26 (s, 1H), 7.89 (s, 1H), 7.58-7.46 (m, 10H). MH+ 289.

Step 4: 6-chloro-8,9-diphenyl-9H-purine (compound (6))

8,9-diphenyl-1H-purin-6(9H)-one obtained in step 3 (22.3 g, 77.4 mmol) was dissolved in POCl₃ (70 ml) at 0° C. and the reaction mixture was heated to reflux at 110° C. overnight. After cooled to room temperature, ice-water was added to the resulting reaction mixture and stirred for 30 min at room temperature. The resulting mixture was filtered with water. The collected solid was dried under reduced pressure to obtain the title compound (20 g, 84%) as beige solid.
MH+ 307

Example 1

N-(3-(4-(2,3-dichlorophenyl)piperazin-1-yl)propyl)-8,9-diphenyl-9H-purine-6-amine

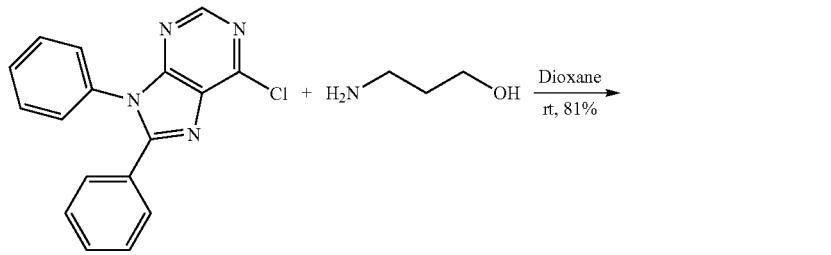

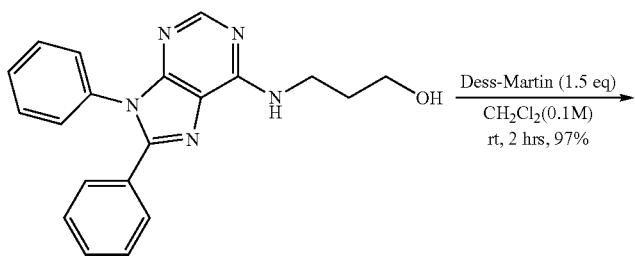

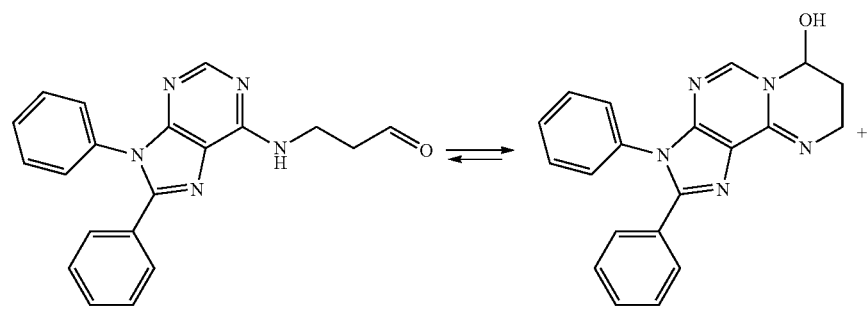

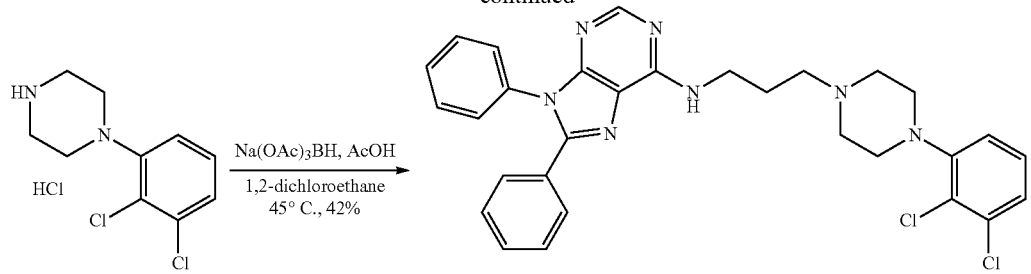

Step 1: 3-(8,9-diphenyl-9H-purin-6-ylamino)propan-1-ol (compound (10))

To the solution of 6-chloro-8,9-diphenyl-9H-purine obtained in step 4 of Example 8 (0.67 g, 2.18 mmol) in dioxane was added 3-aminopropan-1-ol (1.66 mL, 21.8 mmol) at room temperature and stirred for 4 hours at room temperature. The resulting reaction mixture was concentrated under reduced pressure. The residue was diluted with $CH_2Cl_2$, and washed with water. The organic layer thus separated was dried over anhydrous $MgSO_4$ and evaporated in vacuo to provide title compound (0.77 g, 98%) as yellow solid.
$^1$H NMR (400 MHz, DMSO-$d_6$) δ 8.14 (s, 1H), 7.90 (s, 1H), 7.48-7.43 (m, 5H), 7.36-7.30 (m, 5H), 4.50 (t, J=5.2 Hz, 2H), 3.50-3.47 (m, 2H), 1.75 (t, J=5.2 Hz, 2H).
MH+ 346.

Step 2: 3-(8,9-diphenyl-9H-purin-6-ylamino)propanal (compound (11))

To the solution of 3-(8,9-diphenyl-9H-purin-6-ylamino) propan-1-ol obtained in step 1 (0.77 g, 2.24 mmol) in dichloromethane was added Dess-Martin (1.4 g, 3.37 mmol) at room temperature and stirred for 2 hours at room temperature. The resulting reaction mixture was concentrated under reduced pressure. The residue was diluted with $CH_2Cl_2$, and washed with water. The organic layer thus separated was dried over anhydrous $MgSO_4$ and evaporated in vacuo to provide title compound (0.73 g, 94%) as yellow solid.
MH+ 344.

Step 3: N-(3-(4-(2,3-dichlorophenyl)piperazin-1-yl)propyl)-8,9-diphenyl-9H-purin-6-amine (compound 14)

To the solution of 3-(8,9-diphenyl-9H-purin-6-ylamino) propanal obtained in step 2 (0.73 g, 2.13 mmol) and 1-(2,3-dichlorophenyl)piperazine hydrochloride (0.6 g, 2.13 mmol) in 1,2-dichloroethane was added $Na(OAc)_3BH$ (0.72 g, 3.40 mmol) and acetic acid (0.24 mL, 4.25 mmol) at room temperature and stirred for 18 hours at 45° C. The resulting reaction mixture was concentrated under reduced pressure. The residue was diluted with $CH_2Cl_2$, and washed with water. The organic layer thus separated was dried over anhydrous $MgSO_4$, filtered, and concentrated in vacuo. The crude product thus obtained was purified by preparative HPLC (purification system, Gilson) to provide the title compound (460 mg) as a white solid.
$^1$H NMR (400 MHz, $CDCl_3$) δ 8.40 (s, 1H), 7.89 (br.s, 1H), 7.50-7.42 (m, 5H), 7.33-7.29 (m, 3H), 7.18-7.13 (m, 3H), 6.98 (t, J=8.0 Hz, 1H), 6.87-6.85 (m, 1H), 3.82 (br.s, 2H), 3.27 (br.s, 4H), 2.86-2.70 (m, 6H), 1.98-1.92 (m, 2H).
MH+ 558.

Example 2

N-(3-(4-(2,3-dimethylphenyl)piperazin-1-yl)propyl)-8,9-diphenyl-9H-purine-6-amine (compound (8))

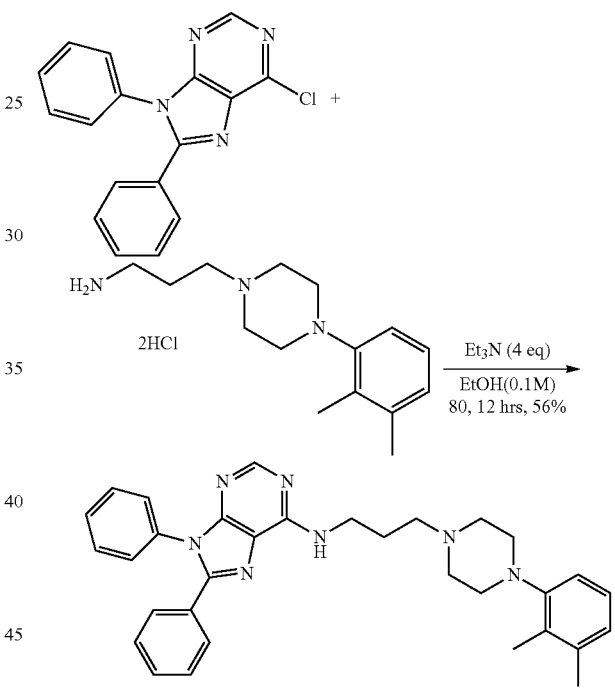

To a mixture of 6-chloro-8,9-diphenyl-9H-purine (150 mg, 0.49 mmol) and 3-(4-(2,3-dimethylphenyl)piperazin-1-yl) propan-1-amine dihydrochloride (313 mg, 0.98 mmol) in ethanol (4.9 mL) was added triethyl amine (0.27 mL, 1.96 mmol) and stirred at 80° C. for 15 hrs. The resulting reaction mixture was concentrated under reduced pressure. The residue was diluted with $CH_2Cl_2$, and washed with water. The organic layer thus separated was dried over anhydrous $MgSO_4$, filtered, and concentrated in vacuo. The crude product thus obtained was purified by preparative HPLC (purification system, Gilson) to provide the title compound (117 mg) as a white solid.
$^1$H NMR (400 MHz, $CDCl_3$) δ 8.40 (s, 1H), 7.51-7.44 (m, 5H), 7.35-7.31 (m, 3H), 7.21 (t, J=7.6 Hz, 2H), 6.98-6.95 (m, 1H), 6.89 (d, J=7.6 Hz, 2H), 3.83 (br.s, 2H), 3.08 (br.s, 4H), 2.79-2.58 (m, 6H), 2.27 (s, 3H), 2.23 (s, 3H), 1.98-1.92 (m, 2H).
MH+ 518.

Example 3

N-(3-(4-(2,3-dichlorophenyl)piperazin-1-yl)propyl)-9-phenyl-8-propyl-9H-purine-6-amine $^1$H NMR (400 MHz, CDCl$_3$) δ 8.33 (s, 1H), 7.58-7.48 (m, 3H), 7.38-7.35 (m, 2H), 7.17-7.12 (m, 2H), 7.04-7.01 (m, 1H), 3.79 (br.s, 2H), 3.24 (br.s, 4H), 2.77 (br.s, 4H), 2.74-2.65 (m, 4H), 1.96-1.89 (m, 2H), 1.70 (q, J=7.2 Hz, 2H), 0.83 (t, J=7.6 Hz, 3H).
MH+ 524.

Example 4

N-(3-(4-(2,3-dichlorophenyl)piperazin-1-yl)propyl)-8-methyl-9-phenyl-9H-purine-6-amine $^1$H NMR (400 MHz, CDCl$_3$) δ 8.33 (s, 1H), 7.59-7.50 (m, 3H), 7.38-7.36 (m, 2H), 7.16-7.15 (m, 2H), 7.06-7.05 (m, 1H), 3.78 (br.s, 2H), 3.21 (br.s, 4H), 2.73 (br.s, 2H), 2.66 (t, J=6.4 Hz, 4H), 2.44 (s, 3H), 1.93 (t, J=6.4 Hz, 2H).
MH+ 496.

Example 5

N-(3-(4-(2,3-dimethylphenyl)piperazin-1-yl)propyl)-8-methyl-9-phenyl-9H-purine-6-amine $^1$H NMR (400 MHz, CDCl$_3$) δ 8.34 (s, 1H), 7.59-7.48 (m, 3H), 7.39-7.36 (m, 2H), 7.10-7.04 (m, 2H), 6.91 (d, J=6.8 Hz, 1H), 3.78 (br.s, 2H), 3.05 (br.s, 4H), 2.66 (t, J=6.4 Hz, 4H), 2.47 (s, 3H), 2.27 (s, 3H), 2.23 (s, 3H), 1.96-1.90 (m, 2H).
MH+ 456.

Example 6

N-(3-(4-(2,3-dichlorophenyl)piperazin-1-yl)propyl)-8-ethyl-9-phenyl-9H-purine-6-amine $^1$H NMR (400 MHz, CDCl$_3$) δ 8.33 (s, 1H), 7.58-7.48 (m, 3H), 7.36-7.34 (m, 2H), 7.17-7.12 (m, 2H), 7.04-7.02 (m, 1H), 3.80 (br.s, 2H), 3.25 (m, 4H), 2.82-2.70 (m, 8H), 1.94 (br.s, 2H), 1.23 (t, J=7.6 Hz, 3H).
MH+ 510.

Example 7

N-(3-(4-(2,3-dimethylphenyl)piperazin-1-yl)propyl)-8-ethyl-9-phenyl-9H-purine-6-amine $^1$H NMR (400 MHz, CDCl$_3$) δ 8.39 (s, 1H), 7.58-7.49 (m, 3H), 7.37-7.32 (m, 2H), 7.07-6.99 (m, 2H), 6.90 (d, J=7.2 Hz, 1H), 3.79 (br.s, 2H), 3.07 (br.s, 4H), 2.75 (q, J=7.6 Hz, 2H), 2.69 (br.s, 4H), 2.27 (s, 3H), 2.23 (s, 3H), 1.95 (br.s, 2H), 1.27 (t, J=7.2 Hz, 3H).
MH+ 470.

Example 8

N-(2-(4-(2,3-dichlorophenyl)piperazin-1-yl)ethyl)-8-methyl-9-phenyl-9H-purine-6-amine $^1$H NMR (400 MHz, CDCl$_3$) δ 8.35 (s, 1H), 7.60-7.49 (m, 3H), 7.39-7.37 (m, 2H), 7.17-7.13 (m, 2H), 7.00-6.95 (m, 1H), 6.14 (br.s, 1H), 3.83 (br.s, 2H), 3.49 (s, 2H), 3.11 (br.s, 4H), 2.77 (t, J=6.0 Hz, 2H), 2.73 (br.s, 4H), 2.50 (s, 3H).
MH+ 482.

Example 9

N-(2-(4-(2,3-dichlorophenyl)piperazin-1-yl)ethyl)-8-ethyl-9-phenyl-9H-purine-6-amine $^1$H NMR (400 MHz, CDCl$_3$) δ 8.34 (s, 1H), 7.59-7.50 (m, 3H), 7.39-7.36 (m, 2H), 7.18-7.13 (m, 2H), 7.00-6.96 (m, 1H), 6.14 (br.s, 1H), 3.84 (br.s, 2H), 3.12 (br.s, 4H), 2.83-2.77 (m, 4H), 2.75 (br.s, 4H), 1.29 (t, J=7.6 Hz, 3H).
MH+ 496.

Example 10

N-(2-(4-(2,3-dimethylphenyl)piperazin-1-yl)ethyl)-8-ethyl-9-phenyl-9H-purine-6-amine $^1$H NMR (400 MHz, CDCl$_3$) δ 8.35 (s, 1H), 7.59-7.49 (m, 3H), 7.39-7.37 (m, 2H), 7.09 (t, J=7.6 Hz, 1H), 6.92 (dd, J=8.0, 7.6 Hz, 2H), 6.17 (br.s, 1H), 3.83 (br.s, 2H), 2.96 (t, J=4.4 Hz, 4H), 2.83-2.76 (m, 4H), 2.72 (br.s, 4H), 2.27 (s, 3H), 2.23 (s, 3H), 1.29 (t, J=7.6 Hz, 3H).
MH+ 456.

Example 11

N-(2-(4-(2,3-dichlorophenyl)piperazin-1-yl)ethyl)-9-phenyl-8-propyl-9H-purine-6-amine $^1$H NMR (400 MHz, CDCl$_3$) δ 8.34 (s, 1H), 7.60-7.52 (m, 3H), 7.38-7.31 (m, 2H), 7.17-7.13 (m, 2H), 6.99-6.96 (m, 1H), 6.15 (br.s, 1H), 3.84 (br.s, 2H), 3.12 (br.s, 4H), 2.79-2.73 (m, 6H), 1.77-1.68 (m, 4H), 0.93 (t, J=7.2 Hz, 3H).
MH+ 510.

Example 12

N-(2-(4-(2,3-dimethylphenyl)piperazin-1-yl)ethyl)-9-phenyl-8-propyl-9H-purine-6-amine $^1$H NMR (400 MHz, CDCl$_3$) δ 8.32 (s, 1H), 7.58-748 (m, 3H), 7.36-7.34 (m, 2H), 7.06 (dd, J=7.6, 8.0 Hz, 1H), 6.90 (dd, J=8.0, 7.6 Hz, 2H), 6.14 (br.s, 1H), 3.81 (br.s, 2H), 2.94-2.89 (m, 4H), 2.76-2.71 (m, 4H), 2.69 (br.s, 4H), 2.25 (s, 3H), 2.21 (s, 3H), 1.76-1.66 (m, 2H), 0.91 (t, J=7.6 Hz, 3H).
MH+ 470.

Example 13

N-(3-(4-(2,3-dimethylphenyl)piperazin-1-yl)propyl)-9-phenyl-9H-purine-6-amine $^1$H NMR (400 MHz, CDCl$_3$) δ 8.45 (s, 1H), 7.98 (s, 1H), 7.70-7.68 (m, 2H), 7.55 (dd, J=7.6, 8.0 Hz, 2H), 7.43 (dd, J=7.2, 7.6 Hz, 1H), 7.13-7.03 (m, 2H), 6.91 (d, J=7.2 Hz, 1H), 3.80 (br.s, 2H), 3.05 (br.s, 4H), 2.68-2.65 (m, 6H), 2.27 (s, 3H), 2.23 (s, 3H), 1.95-1.92 (m, 2H).
MH+ 442.

Example 14

N-(2-(4-(2,3-dimethylphenyl)piperazin-1-yl)ethyl)-9-phenyl-9H-purine-6-amine $^1$H NMR (400 MHz, CDCl$_3$) δ 8.46 (s, 1H), 8.05 (s, 1H), 7.71-7.69 (m, 2H), 7.56 (t, J=7.6 Hz, 2H), 7.44 (dd, J=7.2, 7.6

Hz, 1H), 7.08 (dd, J=7.6, 8.0 Hz, 1H), 6.92 (dd, J=8.0, 7.6 Hz, 2H), 6.39 (br.s, 1H), 3.80 (br.s, 2H), 2.97-2.95 (m, 4H), 2.78 (t, J=6.0 Hz, 2H), 2.72 (br.s, 4H), 2.27 (s, 3H), 2.23 (s, 3H).
MH+ 428.

Example 15

N-(3-(4-(2,3-dichlorophenyl)piperazin-1-yl)propyl)-9-phenyl-9H-purine-6-amine $^1$H NMR (400 MHz, CDCl$_3$) δ 8.44 (s, 1H), 7.97 (s, 1H), 7.70-7.67 (m, 2H), 7.57-7.53 (m, 2H), 7.45-7.41 (m, 1H), 7.17-7.14 (m, 2H), 7.07-7.04 (m, 1H), 3.81 (br.s, 2H), 3.21 (br.s, 4H), 2.72 (br.s, 4H), 2.67 (dd, J=6.4, 6.0 Hz, 2H), 1.97-1.90 (m, 2H).
MH+ 482.

Example 16

1-(4-(2,3-dichlorophenyl)piperazin-1-yl)-3-(9-phenyl-9H-purin-6-ylamino)propan-2-ol $^1$H NMR (400 MHz, CDCl$_3$) δ 8.44 (s, 1H), 8.04 (s, 1H), 7.69 (d, J=8.0 Hz, 2H), 7.57 (t, J=7.6 Hz, 2H), 7.49-7.43 (m, 1H), 7.17-7.12 (m, 2H), 6.95 (dd, J=6.8, 6.8 Hz, 1H), 6.28 (br.s, 1H), 4.08-4.06 (m, 2H), 3.94 (br.s, 1H), 3.75 (br.s, 2H), 3.08 (br.s, 4H), 2.84-2.83 (m, 2H), 2.66-2.65 (m, 2H).
MH+ 498.

Example 17

N-(2-(4-(2,3-dichlorophenyl)piperazin-1-yl)ethyl)-8,9-diphenyl-9H-purine-6-amine $^1$H NMR (400 MHz, CDCl$_3$) δ 8.42 (s, 1H), 7.52-7.45 (m, 5H), 7.39-7.30 (m, 5H), 7.16-7.15 (m, 2H), 6.99-6.97 (m, 1H), 6.34 (br.s, 1H), 3.86 (br.s, 2H), 3.12 (br.s, 4H), 2.80 (t, J=6.0 Hz, 2H), 2.75 (br.s, 4H).
MH+ 544.

Example 18

N-(2-(4-(2,3-dimethylphenyl)piperazin-1-yl)ethyl)-8,9-diphenyl-9H-purine-6-amine $^1$H NMR (400 MHz, CDCl$_3$) δ 8.41 (s, 1H), 7.53-7.42 (m, 5H), 7.39-7.29 (m, 5H), 7.08 (t, J=7.6 Hz, 1H), 6.92 (dd, J=8.0, 7.2 Hz, 2H), 6.37 (br.s, 1H), 3.86 (br.s, 2H), 2.95 (t, J=4.4 Hz, 4H), 2.78 (t, J=6.0 Hz, 2H), 2.72 (br.s, 4H), 2.27 (s, 3H), 2.23 (s, 3H).
MH+ 504.

Example 19

1-(4-(2,3-dichlorophenyl)piperazin-1-yl)-3-(8,9-diphenyl-9H-purin-6-ylamino)propan-2-ol $^1$H NMR (400 MHz, CDCl$_3$) δ 8.34 (s, 1H), 7.51-7.44 (m, 5H), 7.39-7.29 (m, 5H), 7.21-7.08 (m, 2H), 6.96-6.94 (m, 1H), 6.39 (br.s, 1H), 4.14-4.12 (m, 1H), 3.98-3.94 (m, 1H), 3.79-3.77 (m, 1H), 3.11 (br.s, 4H), 2.89-2.87 (m, 2H), 2.72 (br.s, 2H), 2.63 (d, J=6.8 Hz, 2H).
MH+ 574.

Example 20

1-(4-(2,3-dichlorophenyl)piperazin-1-yl)-3-(8-methyl-9-phenyl-9H-purin-6-ylamino)propan-2-ol $^1$H NMR (400 MHz, CDCl$_3$) δ 8.33 (s, 1H), 7.60-7.49 (m, 3H), 7.39-7.30 (m, 2H), 7.20-7.12 (m, 2H), 6.96 (dd, J=2.8, 2.8 Hz, 1H), 6.14 (br.s, 1H), 4.25-4.23 (m, 1H), 4.08-4.06 (1H), 3.92-3.90 (m, 1H), 3.75-3.73 (m, 1H), 3.08 (br.s, 4H), 2.84-2.82 (m, 2H), 2.66-2.65 (m, 2H), 2.58-2.57 (m, 1H), 2.56 (s, 3H).
MH+ 512.

Example 21

1-(4-(2,3-dichlorophenyl)piperazin-1-yl)-3-(8-ethyl-9-phenyl-9H-purin-6-ylamino)propan-2-ol $^1$H NMR (400 MHz, CDCl$_3$) δ 8.32 (s, 1H), 7.59-7.49 (m, 3H), 7.36 (d, J=8.0 Hz, 2H), 7.17-7.12 (m, 2H), 6.96 (dd, J=3.2, 2.8 Hz, 1H), 6.17 (br.s, 1H), 4.32 (br.s, 1H), 4.09-4.07 (m, 1H), 3.94-3.90 (m, 1H), 3.75-3.71 (m, 1H), 3.08 (br.s, 4H), 2.83-2.75 (m, 4H), 2.67-2.50 (m, 3H), 1.29 (t, J=7.2 Hz, 3H).
MH+ 526.

Example 22

1-(4-(2,3-dichlorophenyl)piperazin-1-yl)-3-(9-phenyl-8-propyl-9H-purin-6-ylamino)propan-2-ol $^1$H NMR (400 MHz, CDCl$_3$) δ 8.32 (s, 1H), 7.59-7.50 (m, 3H), 7.37-7.35 (m, 2H), 7.17-7.12 (m, 2H), 6.96 (dd, J=2.8, 3.2 Hz, 1H), 6.17 (br.s, 1H), 4.31 (br.s, 1H), 4.09-4.08 (m, 1H), 3.93-3.91 (m, 1H), 3.75-3.73 (m, 1H), 3.08 (br.s, 4H), 2.85-2.82 (m, 2H), 2.75-2.71 (m, 2H), 2.68-2.62 (m, 2H), 2.58-2.56 (m, 2H), 1.78-1.69 (m, 2H), 0.93 (t, J=7.2 Hz, 3H).
MH+ 540.

Example 23

N-(3-(4-(2,3-dimethylphenyl)piperazin-1-yl)propyl)-9-methyl-8-phenyl-9H-purine-6-amine $^1$H NMR (400 MHz, CDCl$_3$) δ 8.41 (s, 1H), 7.76 (dd, J=8.0, 1.6 Hz, 2H), 7.50-7.44 (m, 3H), 6.96-6.84 (m, 3H), 3.87 (s, 3H), 3.79 (br.s, 2H), 3.02 (br.s, 4H), 2.67-2.64 (m, 6H), 2.26 (s, 3H), 2.21 (s, 3H), 1.94-1.91 (m, 2H).
MH+ 456.

Example 24

1-(4-(2,3-dimethylphenyl)piperazin-1-yl)-3-(9-methyl-8-phenyl-9H-purin-6-ylamino)propan-2-ol $^1$H NMR (400 MHz, CDCl$_3$) δ 8.40 (s, 1H), 7.76-7.74 (m, 2H), 7.56-7.52 (m, 3H), 7.06 (t, J=7.6 Hz, 1H), 6.91-6.89 (m, 2H), 6.29 (br.s, 1H), 4.32 (br.s, 1H), 4.09-4.03 (m, 1H), 3.95-3.91 (m, 1H), 3.88 (s, 3H), 3.73-3.70 (m, 1H), 2.90-2.86 (m, 4H), 2.78 (br.s, 2H), 2.60-2.56 (m, 2H), 2.55-2.52 (m, 2H), 2.26 (s, 3H), 2.20 (s, 3H).
MH+ 472.

Example 25

1-(4-(2,3-dimethylphenyl)piperazin-1-yl)-3-(9-phenyl-9H-purin-6-ylamino)propan-2-ol $^1$H NMR (400 MHz, CDCl$_3$) δ 8.44 (s, 1H), 8.04 (s, 1H), 7.70-7.68 (m, 2H), 7.56 (t, J=8.0 Hz, 2H), 7.44 (dd, J=7.6, 7.2 Hz, 1H), 7.07 (t, J=7.6 Hz, 1H), 6.91 (dd, J=7.2, 6.4 Hz, 2H), 6.31 (br.s, 1H), 4.10-4.05 (m, 1H), 3.94 (br.s, 1H), 3.73 (br.s, 1H), 2.95-2.91 (m, 4H), 2.88-2.81 (m, 2H), 2.62 (br.s, 2H), 2.56 (d, J=6.8 Hz, 2H), 2.26 (s, 3H), 2.21 (s, 3H).
MH+ 458.

Example 26

1-(4-(2,3-dimethylphenyl)piperazin-1-yl)-3-(8-ethyl-9-phenyl-9H-purin-6-ylamino)propan-2-ol $^1$H NMR (400 MHz, CDCl$_3$) δ 8.32 (s, 1H), 7.59-7.49 (m, 3H), 7.38-7.30 (m, 2H), 7.07 (dd, J=7.6, 8.0 Hz, 1H), 6.91 (dd, J=8.0, 7.2 Hz, 2H), 6.18 (br.s, 1H), 4.08-4.04 (m, 1H), 3.95-3.93 (m, 1H), 3.73 (br.s, 1H), 2.92-2.88 (m, 4H), 2.81-2.75 (m, 4H), 2.60 (br.s, 2H), 2.57-2.55 (m, 2H), 2.26 (s, 3H), 2.21 (s, 3H), 1.30 (t, J=7.6 Hz, 3H).
MH+ 486.

Example 27

1-(4-(2,3-dimethylphenyl)piperazin-1-yl)-3-(8,9-diphenyl-9H-purin-6-ylamino)propan-2-ol $^1$H NMR (400 MHz, CDCl$_3$) δ 8.39 (s, 1H), 7.52-7.43 (m, 5H), 7.37-7.31 (m, 5H), 7.06 (dd, J=7.6, 8.0 Hz, 1H), 6.92-6.89 (m, 2H), 6.36 (br.s, 1H), 4.21 (br.s, 1H), 4.11-4.09 (m, 1H), 3.95 (br.s, 1H), 3.79-3.75 (m, 1H), 2.92-2.82 (m, 4H), 2.68 (br.s, 2H), 2.63-2.57 (m, 4H), 2.26 (s, 3H), 2.21 (s, 3H).
MH+ 534.

Example 28

N-(3-(4-(2,3-dimethylphenyl)piperazin-1-yl)propyl)-8,9-dimethyl-9H-purine-6-amine $^1$H NMR (400 MHz, CDCl$_3$) δ 8.34 (s, 1H), 7.08 (dd, J=8.0, 7.2 Hz, 1H), 7.01 (d, J=7.6 Hz, 1H), 6.89 (d, J=6.8 Hz, 1H), 6.84 (br.s, 1H), 3.75 (q, J=5.6 Hz, 2H), 3.70 (s, 3H), 3.01 (dd, J=4.4, 4.8 Hz, 4H), 2.65 (br.s, 2H), 2.61 (t, J=6.8 Hz, 4H), 2.53 (s, 3H), 2.27 (s, 3H), 2.22 (s, 3H), 1.93-1.87 (m, 2H).
MH+ 394.

Example 29

N-(3-(4-(2,3-dimethylphenyl)piperazin-1-yl)propyl)-9-methyl-9H-purine-6-amine $^1$H NMR (400 MHz, DMSO-d$_6$) δ 10.27 (br.s, 1H), 8.21 (s, 1H), 8.09 (s, 1H), 7.83 (br.s, 1H), 7.05-7.01 (m, 1H) 6.87 (t, J=8.8 Hz, 2H), 3.70 (s, 3H), 3.55 (br.s, 2H), 3.28-3.19 (m, 6H), 3.15-3.13 (m, 2H), 3.03 (br.s, 2H), 2.18 (s, 3H), 2.12 (s, 3H), 2.04 (t, J=7.6 Hz, 2H).
MH+ 380.

Example 30

1-(4-(2,3-dimethylphenyl)piperazin-1-yl)-3-(9-methyl-9H-purin-6-ylamino)propan-2-ol $^1$H NMR (400 MHz, DMSO-d$_6$) δ 8.19 (br.s, 1H), 8.06 (s, 1H), 7.53 (br.s, 1H), 6.99 (dd, J=8.0, 7.6 Hz, 1H), 6.83 (dd, J=8.0, 7.2 Hz, 2H), 4.89 (br.s, 1H), 3.92-3.89 (m, 1H), 3.68 (s, 3H), 3.55-3.51 (m, 2H), 3.28 (br.s, 4H), 2.76 (br.s, 4H), 2.58-2.53 (m, 2H), 2.15 (s, 3H), 2.10 (s, 3H). MH+ 396.

Example 31

9-tert-butyl-N-(3-(4-(2,3-dimethylphenyl)piperazin-1-yl)propyl)-9H-purine-6-amine $^1$H NMR (400 MHz, CDCl$_3$) δ 8.37 (s, 1H), 7.78 (s, 1H), 7.09 (dd, J=8.0, 7.6 Hz, 1H), 7.00 (d, J=8.4 Hz, 1H), 6.89 (d, J=7.2 Hz, 1H), 3.75 (br.s, 2H), 3.00 (t, J=4.4 Hz, 4H), 2.67 (br.s, 2H), 2.62 (t, J=6.4 Hz, 4H), 2.27 (s, 3H), 2.22 (s, 3H), 1.91 (t, J=6.4 Hz, 2H), 1.78 (s, 9H).
MH+ 422.

Example 32

1-(9-tert-butyl-9H-purin-6-ylamino)-3-(4-(2,3-dimethylphenyl)piperazin-1-yl)propan-2-ol $^1$H NMR (400 MHz, CDCl$_3$) δ 8.36 (s, 1H), 7.83 (s, 1H), 7.07 (t, J=7.6 Hz, 1H), 6.90 (dd, J=6.4, 6.0 Hz, 2H), 6.18 (br.s, 1H), 4.36 (br.s, 1H), 4.07-4.03 (m, 1H), 2.90 (br.s, 6H), 2.78 (br.s, 2H), 2.61 (br.s, 2H), 2.55-2.52 (m, 2H), 2.26 (s, 3H), 2.20 (s, 3H), 1.79 (s, 9H).
MH+ 438.

Example 33

1-(9-(benzo[d][1,3]dioxol-5-yl)-9H-purin-6-ylamino)-3-(4-(2,3-dimethylphenyl)piperazin-1-yl)propan-2-ol $^1$H NMR (400 MHz, DMSO-d$_6$) δ 10.58 (br.s, 1H), 9.56 (br.s, 1H), 8.74 (s, 1H), 8.42 (s, 1H), 7.38 (s, 1H), 7.24 (d, J=8.4 Hz, 1H), 7.12 (d, J=8.0 Hz, 1H), 7.04 (dd, J=7.6, 8.0 Hz, 1H), 6.90-6.86 (m, 2H), 6.14 (s, 2H), 4.43 (br.s, 1H), 3.75-3.73 (m, 1H), 3.64-3.43 (m, 4H), 3.30-3.20 (m, 4H), 3.17-3.08 (m, 4H), 2.18 (s, 3H), 2.13 (m, 3H).
MH+ 502.

Example 34

9-(benzo[d][1,3]dioxol-5-yl)-N-(3-(4-(2,3-dimethylphenyl)piperazin-1-yl)propyl)-9H-purine-6-amine $^1$H NMR (400 MHz, DMSO-d$_6$) δ 11.03 (br.s, 1H), 9.44 (br.s, 1H), 8.70 (s, 1H), 8.42 (s, 1H), 7.38 (s, 1H), 7.24 (d, J=8.0 Hz, 1H), 7.11 (d, J=8.0 Hz, 1H), 7.04 (dd, J=7.6, 8.0 Hz, 1H), 6.91-6.86 (m, 2H), 6.13 (s, 2H), 3.71 (br.s, 2H), 3.51 (br.s, 2H), 3.25 (br.s, 2H), 3.18-3.09 (m, 8H), 2.18 (s, 3H), 2.13 (s, 3H).
MH+ 486.

Example 35

1-(9-(benzo[d][1,3]dioxol-5-yl)-8-methyl-9H-purin-6-ylamino)-3-(4-(2,3-dimethylphenyl)piperazin-1-yl)propan-2-ol $^1$H NMR (400 MHz, DMSO-$d_6$) δ 10.30 (br.s, 1H), 8.31 (br.s, 1H), 7.16 (d, J=2.0 Hz, 1H), 7.13 (d, J=8.0 Hz, 1H), 7.06-7.00 (m, 2H), 6.98-6.86 (m, 2H), 6.15 (s, 2H), 4.38 (br.s, 1H), 3.70-3.40 (m, 4H), 3.30-3.22 (m, 4H), 3.09 (br.s, 4H), 2.44 (s, 3H), 2.19 (s, 3H), 2.14 (s, 3H).
MH+ 516.

Example 36

9-(benzo[d][1,3]dioxol-5-yl)-N-(3-(4-(2,3-dimethylphenyl)piperazin-1-yl)propyl)-8-methyl-9H-purine-6-amine $^1$H NMR (400 MHz, DMSO-$d_6$) δ 8.28 (s, 1H), 7.14-7.10 (m, 2H), 7.04 (t, J=7.6 Hz, 1H), 6.96 (dd, J=8.4, 2.0 Hz, 1H), 6.89 (t, J=8.8 Hz, 2H), 6.15 (s, 2H), 3.83-3.55 (m, 6H), 3.25 (br.s, 4H), 3.08 (br.s, 4H), 2.42 (s, 3H), 2.19 (s, 3H), 2.14 (s, 3H).
MH+ 500.

Example 37

8-tert-butyl-N-(3-(4-(2,3-dimethylphenyl)piperazin-1-yl)propyl)-9-methyl-9H-purine-6-amine $^1$H NMR (400 MHz, DMSO-$d_6$) δ 11.00 (br.s, 1H), 9.43 (br.s, 1H), 8.43 (s, 1H), 7.04 (t, J=7.6 Hz, 1H), 6.91-6.86 (m, 2H), 3.93 (s, 3H), 3.69 (br.s, 2H), 3.49 (br.s, 2H), 3.25-3.15 (m, 6H), 3.13-3.08 (m, 4H), 2.18 (s, 3H), 2.13 (s, 3H), 1.49 (s, 9H).
MH+ 436.

Example 38

1-(8-tert-butyl-9-methyl-9H-purin-6-ylamino)-3-(4-(2,3-dimethylphenyl)piperazin-1-yl)propan-2-ol $^1$H NMR (400 MHz, DMSO-$d_6$) δ 10.52 (br.s, 1H), 9.40 (br.s, 1H), 8.43 (s, 1H), 7.06-7.02 (m, 1H), 6.91-6.86 (m, 2H), 4.37 (br.s, 1H), 3.94 (s, 3H), 3.70-3.43 (m, 6H), 3.28-3.20 (m, 3H), 3.16-3.08 (m, 4H), 2.18 (s, 3H), 2.13 (s, 3H), 1.50 (s, 9H).
MH+ 452.

Example 39

9-(benzo[d][1,3]dioxol-5-yl)-N-(3-(4-(2,3-dimethylphenyl)piperazin-1-yl)propyl)-8-ethyl-9H-purine-6-amine $^1$H NMR (400 MHz, DMSO-$d_6$) δ 11.22 (br.s, 1H), 9.70 (br.s, 1H), 8.34 (s, 1H), 7.16 (d, J=1.6 Hz, 1H), 7.11 (d, J=8.4 Hz, 1H), 7.06-6.98 (m, 2H), 6.89 (d, J=7.6 Hz, 1H), 6.86 (d, J=7.6 Hz, 1H), 6.15 (s, 2H), 3.74-3.68 (m, 2H), 3.53-3.50 (m, 2H), 3.26 (br.s, 2H), 3.15-3.12 (m, 6H), 2.75 (q, J=7.2 Hz, 2H), 2.18 (s, 3H), 2.13 (s, 3H), 1.23 (t, J=7.2 Hz, 3H).
MH+ 514.

Example 40

1-(9-(benzo[d][1,3]dioxol-5-yl)-8-ethyl-9H-purin-6-ylamino)-3-(4-(2,3-dimethylphenyl)piperazin-1-yl)propan-2-ol $^1$H NMR (400 MHz, DMSO-$d_6$) δ 10.39 (br.s, 1H), 9.20 (br.s, 1H), 8.30 (s, 1H), 7.15 (d, J=2.4 Hz, 1H), 7.10 (d, J=8.4 Hz, 1H), 7.03 (dd, J=8.0, 7.6 Hz, 1H), 6.98 (dd, J=8.0, 2.0 Hz, 1H), 6.89 (d, J=7.6 Hz, 1H), 6.86 (d, J=8.0 Hz, 1H), 6.15 (s, 2H), 4.38 (br.s, 1H), 3.70-3.64 (m, 2H), 3.48-3.41 (m, 2H), 3.36-3.21 (m, 4H), 3.19-3.09 (m, 4H), 2.75 (q, J=7.6 Hz, 2H), 2.18 (s, 3H), 2.13 (s, 3H), 1.22 (t, J=7.2 Hz, 3H).
MH+ 530.

Example 41

9-(2,3-dihydrobenzo[b][1,4]dioxin-6-yl)-N-(3-(4-(2,3-dimethylphenyl)piperazin-1-yl)propyl)-9H-purine-6-amine $^1$H NMR (400 MHz, DMSO-$d_6$) δ 11.15 (br.s, 1H), 8.73 (s, 1H), 8.42 (s, 1H), 7.32 (s, 1H), 7.23 (d, J=6.4 Hz, 1H), 7.07-7.02 (m, 2H), 6.90-6.85 (m, 2H), 4.29 (s, 4H), 3.74-3.69 (m, 2H), 3.61-3.53 (m, 4H), 3.25 (br.s, 2H), 3.14-3.08 (m, 6H), 2.18 (s, 3H), 2.13 (s, 3H).
MH+ 500.

Example 42

1-(9-(2,3-dihydrobenzo[b][1,4]dioxin-6-yl)-9H-purin-6-ylamino)-3-(4-(2,3-dimethylphenyl)piperazin-1-yl)propan-2-ol $^1$H NMR (400 MHz, DMSO-$d_6$) δ 10.58 (br.s, 1H), 8.76 (s, 1H), 8.43 (s, 1H), 7.33 (s, 1H), 7.23 (d, J=6.8 Hz, 1H), 7.22-7.01 (m, 2H), 6.90-6.85 (m, 2H), 4.42 (br.s, 1H), 4.29 (s, 4H), 3.76-3.70 (m, 2H), 3.56-3.52 (m, 2H), 3.35-3.27 (m, 4H), 3.20-3.04 (m, 4H), 2.17 (s, 3H), 2.12 (s, 3H).
MH+ 516.

Example 43

9-(2,3-dihydrobenzo[b][1,4]dioxin-6-yl)-N-(3-(4-(2,3-dimethylphenyl)piperazin-1-yl)propyl)-8-methyl-9H-purine-6-amine $^1$H NMR (400 MHz, DMSO-$d_6$) δ 11.06 (br.s, 1H), 9.70 (br.s, 1H), 8.34 (s, 1H), 7.09-7.02 (m, 3H), 6.99-6.96 (m, 1H), 6.90-6.86 (m, 2H), 4.30 (s, 4H), 3.73-3.70 (m, 4H), 3.53-3.48 (m, 4H), 3.25 (br.s, 2H), 3.15-3.09 (m, 4H), 2.43 (s, 3H), 2.18 (s, 3H), 2.13 (s, 3H).
MH+ 514.

Example 44

1-(9-(2,3-dihydrobenzo[b][1,4]dioxin-6-yl)-8-methyl-9H-purin-6-ylamino)-3-(4-(2,3-dimethylphenyl)piperazin-1-yl)propan-2-ol $^1$H NMR (400 MHz, DMSO-$d_6$) δ 10.39 (br.s, 1H), 9.17 (br.s, 1H), 8.30 (s, 1H), 7.08-7.02 (m, 3H), 6.98-6.95 (m, 1H), 6.90-6.86 (m, 2H), 4.37 (br.s, 2H), 4.30 (s, 4H), 3.70-3.61 (m, 3H), 3.39-3.29 (m, 4H), 3.09 (br.s, 4H), 2.45 (s, 3H), 2.18 (s, 3H), 2.13 (s, 3H).
MH+ 530.

Example 45

9-(2,3-dihydrobenzo[b][1,4]dioxin-6-yl)-N-(3-(4-(2,3-dimethylphenyl)piperazin-1-yl)propyl)-8-ethyl-9H-purine-6-amine $^1$H NMR (400 MHz, DMSO-d$_6$) δ 11.25 (br.s, 1H), 9.72 (br.s, 1H), 8.34 (s, 1H), 7.09-7.02 (m, 3H), 6.98-6.96 (m, 1H), 6.90-6.88 (m, 2H), 4.30 (s, 4H), 3.75 (br.s, 2H), 3.51 (br.s, 2H), 3.26 (br.s, 4H), 3.15-3.08 (m, 6H), 2.74 (q, J=7.2 Hz, 2H), 2.18 (s, 3H), 2.13 (s, 3H), 1.23 (t, J=7.2 Hz, 3H).
MH+ 528.

Example 46

1-(9-(2,3-dihydrobenzo[b][1,4]dioxin-6-yl)-8-ethyl-9H-purin-6-ylamino)-3-(4-(2,3-dimethylphenyl)piperazin-1-yl)propan-2-ol $^1$H NMR (400 MHz, DMSO-d$_6$) δ 10.70 (br.s, 1H), 9.67 (br.s, 1H), 8.34 (s, 1H), 7.10-7.01 (m, 4H), 6.99-6.85 (m, 2H), 4.42 (br.s, 1H), 4.30 (s, 4H), 3.79-3.72 (m, 2H), 3.48-3.43 (m, 2H), 3.23-3.19 (m, 4H), 3.12-3.09 (m, 4H), 2.75 (q, J=7.6 Hz, 2H), 2.18 (s, 3H), 2.13 (s, 3H), 1.24 (t, J=7.2 Hz, 3H).
MH+ 544.

Example 47

N-(3-(4-(2,3-dimethylphenyl)piperazin-1-yl)propyl)-9-(4-fluorophenyl)-9H-purine-6-amine $^1$H NMR (400 MHz, DMSO-d$_6$) δ 11.13 (s, 1H), 9.48 (br.s, 1H), 8.79 (s, 1H), 8.43 (s, 1H), 7.86-7.73 (m, 2H), 7.47 (t, J=8.8 Hz, 3H), 7.06-7.02 (m, 1H), 6.90-6.86 (m, 2H), 3.73 (br.s, 2H), 3.51 (br.s, 2H), 3.25 (br.s, 4H), 3.16-3.08 (m, 6H), 2.18 (s, 3H), 2.13 (s, 3H).
MH+ 460.

Example 48

1-(4-(2,3-dimethylphenyl)piperazin-1-yl)-3-(9-(4-fluorophenyl)-9H-purin-6-ylamino)propan-2-ol $^1$H NMR (400 MHz, DMSO-d$_6$) δ 10.66 (br.s, 1H), 9.76 (br.s, 1H), 8.84 (s, 1H), 8.44 (s, 1H), 7.86-7.83 (m, 2H), 7.47 (t, J=8.8 Hz, 3H), 7.05-7.01 (m, 1H), 6.90-6.85 (m, 2H), 4.44 (br.s, 1H), 3.79-3.71 (m, 2H), 3.67-3.52 (m, 2H), 3.28-3.20 (m, 4H), 3.17-3.09 (m, 4H), 2.18 (s, 3H), 2.13 (s, 3H).
MH+ 476.

Example 49

N-(3-(4-(2,3-dimethylphenyl)piperazin-1-yl)propyl)-9-(4-fluorophenyl)-8-methyl-9H-purine-6-amine $^1$H NMR (400 MHz, DMSO-d$_6$) δ 11.26 (br.s, 1H), 9.79 (br.s, 1H), 8.35 (s, 1H), 7.64-7.60 (m, 2H), 7.50-7.45 (m, 2H), 7.06-7.02 (m, 1H), 6.90-6.86 (m, 2H), 3.75 (br.s, 2H), 3.50 (br.s, 2H), 3.26 (br.s, 4H), 3.16-3.09 (m, 6H), 2.45 (s, 3H), 2.18 (s, 3H), 2.13 (s, 3H).
MH+ 474.

Example 50

1-(4-(2,3-dimethylphenyl)piperazin-1-yl)-3-(9-(4-fluorophenyl)-8-methyl-9H-purin-6-ylamino)propan-2-ol $^1$H NMR (400 MHz, DMSO-d$_6$) δ 10.75 (br.s, 1H), 9.78 (br.s, 1H), 8.35 (s, 1H), 7.65-7.62 (m, 2H), 7.51-7.45 (m, 2H), 7.05-7.01 (m, 1H), 6.90-6.85 (m, 2H), 4.43 (br.s, 1H), 3.80-3.67 (m, 2H), 3.61-3.52 (m, 2H), 3.35-3.29 (m, 4H), 3.18-3.10 (m, 4H), 2.45 (s, 3H), 2.18 (s, 3H), 2.13 (s, 3H).
MH+ 490.

Example 51

N-(3-(4-(2,3-dimethylphenyl)piperazin-1-yl)propyl)-8-ethyl-9-(4-fluorophenyl)-9H-purine-6-amine $^1$H NMR (400 MHz, DMSO-d$_6$) δ 11.20 (br.s, 1H), 9.67 (br.s, 1H), 8.42 (s, 1H), 7.63-7.60 (m, 2H), 7.50-7.45 (m, 2H), 7.06-7.02 (m, 1H), 6.91-6.86 (m, 2H), 3.73 (br.s, 2H), 3.50 (br.s, 2H), 3.26 (br.s, 4H), 3.15-3.09 (m, 6H), 2.74 (q, J=7.6 Hz, 2H), 2.18 (s, 3H), 2.13 (s, 3H), 1.22 (t, J=7.6 Hz, 3H).
MH+ 488.

Example 52

1-(4-(2,3-dimethylphenyl)piperazin-1-yl)-3-(8-ethyl-9-(4-fluorophenyl)-9H-purin-6-ylamino)propan-2-ol $^1$H NMR (400 MHz, DMSO-d$_6$) δ 10.72 (br.s, 1H), 9.69 (br.s, 1H), 8.34 (s, 1H), 7.65-7.61 (m, 2H), 7.50-7.45 (m, 2H), 7.05-7.01 (m, 1H), 6.90-6.85 (m, 2H), 4.43 (br.s, 1H), 3.64-3.61 (m, 2H), 3.57-3.52 (m, 2H), 3.48-3.43 (m, 4H), 3.29-3.12 (m, 4H), 2.75 (q, J=7.6 Hz, 2H), 2.18 (s, 3H), 2.13 (s, 3H), 1.23 (t, J=7.6 Hz, 3H).
MH+ 504.

Example 53

8-tert-butyl-N-(3-(4-(2,3-dimethylphenyl)piperazin-1-yl)propyl)-9-phenyl-9H-purine-6-amine $^1$H NMR (400 MHz, DMSO-d$_6$) δ 11.26 (br.s, 1H), 9.67 (br.s, 1H), 8.28 (s, 1H), 7.64-7.60 (m, 3H), 7.58-7.53 (m, 2H), 7.03 (dd, J=7.6, 8.0 Hz, 1H), 6.91-6.86 (m, 2H), 3.76-3.74 (m, 2H), 3.53-3.50 (m, 4H), 3.27-3.17 (m, 2H), 3.14-3.09 (m, 6H), 2.18 (s, 3H), 2.13 (s, 3H), 1.26 (s, 9H). MH+ 498.

Example 54

1-(8-tert-butyl-9-phenyl-9H-purin-6-ylamino)-3-(4-(2,3-dimethylphenyl)piperazin-1-yl)propan-2-ol $^1$H NMR (400 MHz, DMSO-d$_6$) δ 10.50 (br.s, 1H), 9.30 (br.s, 1H), 8.26 (s, 1H), 7.61-7.58 (m, 3H), 7.57-7.50 (m, 2H), 7.03 (dd, J=7.6, 8.0 Hz, 1H), 6.91-6.84 (m, 2H), 4.40 (br.s, 1H), 3.72-3.70 (m, 2H), 3.56-3.50 (m, 4H), 3.36-3.29 (m, 4H), 3.08-3.05 (m, 4H), 2.18 (s, 3H), 2.13 (s, 3H), 1.26 (s, 9H).
MH+ 514.

Example 55

N-(2-(4-(2,3-dimethylphenyl)piperazin-1-yl)ethyl)-9-(4-fluorophenyl)-8-methyl-9H-purine-6-amine $^1$H NMR (400 MHz, DMSO-d$_6$) δ 9.20 (br.s, 1H), 8.35 (br.s, 1H), 7.62-7.58 (m, 2H), 7.49-7.39 (m, 2H), 7.03 (t, J=7.6 Hz, 1H), 6.91-6.87 (m, 2H), 4.08 (br.s, 2H), 3.63 (br.s, 2H), 3.52-3.45 (m, 4H), 3.12-3.10 (m, 4H), 2.18 (s, 3H), 2.14 (s, 3H).
MH+ 460.

Example 56

N-(2-(4-(2,3-dimethylphenyl)piperazin-1-yl)ethyl)-8-ethyl-9-(4-fluorophenyl)-9H-purine-6-amine $^1$H NMR (400 MHz, DMSO-d$_6$) δ 10.72 (br.s, 1H), 8.36 (br.s, 1H), 8.31 (s, 1H), 7.60-7.56 (m, 2H), 7.48-7.43 (m, 2H), 7.04 (t, J=7.6 Hz, 1H), 6.91-6.87 (m, 2H), 4.02 (br.s, 2H), 3.67-3.62 (m, 2H), 3.48-3.41 (m, 4H), 3.12-3.09 (m, 4H), 2.73 (q, J=7.6 Hz, 2H), 2.18 (s, 3H), 2.14 (s, 3H), 1.21 (t, J=7.6 Hz, 3H).
MH+ 474.

Example 57

9-(benzo[d][1,3]dioxol-5-yl)-N-(2-(4-(2,3-dimethylphenyl)piperazin-1-yl)ethyl)-8-methyl-9H-purine-6-amine $^1$H NMR (400 MHz, DMSO-d$_6$) δ 8.30 (s, 1H), 7.13-7.09 (m, 1H), 7.06-7.02 (m, 2H), 6.97-6.95 (m, 1H), 6.91-6.87 (m, 2H), 6.14 (s, 2H), 4.02 (br.s, 2H), 3.62 (br.s, 2H), 3.47-3.43 (m, 4H), 3.12-3.10 (m, 4H), 2.42 (s, 3H), 2.18 (s, 3H), 2.14 (s, 3H).
MH+ 486.

Example 58

9-(benzo[d][1,3]dioxol-5-yl)-N-(2-(4-(2,3-dimethylphenyl)piperazin-1-yl)ethyl)-8-ethyl-9H-purine-6-amine $^1$H NMR (400 MHz, DMSO-d$_6$) δ 10.67 (br.s, 1H), 8.87 (br.s, 1H), 8.31 (s, 1H), 7.13-7.09 (m, 1H), 7.06-7.02 (m, 2H), 6.96-6.91 (m, 1H), 6.91-6.87 (m, 2H), 6.14 (s, 2H), 4.01 (br.s, 2H), 3.70-3.61 (m, 2H), 3.47-3.42 (m, 4H), 3.12-3.09 (m, 4H), 2.74 (q, J=7.6 Hz, 2H), 2.18 (s, 3H), 2.14 (s, 3H), 1.21 (t, J=7.6 Hz, 3H).
MH+ 500.

Example 59

9-(2,3-dihydrobenzo[b][1,4]dioxin-6-yl)-N-(2-(4-(2,3-dimethylphenyl)piperazin-1-yl)ethyl)-8-methyl-9H-purine-6-amine $^1$H NMR (400 MHz, DMSO-d$_6$) δ 9.17 (br.s, 1H), 8.34 (s, 1H), 7.07-7.02 (m, 3H), 6.97-6.94 (m, 1H), 6.91-6.87 (m, 2H), 4.30 (br.s, 6H), 4.06 (br.s, 2H), 3.52-3.45 (m, 4H), 3.12-3.10 (m, 4H), 2.43 (s, 3H), 2.18 (s, 3H), 2.14 (s, 3H).
MH+ 500.

Example 60

9-(2,3-dihydrobenzo[b][1,4]dioxin-6-yl)-N-(2-(4-(2,3-dimethylphenyl)piperazin-1-yl)ethyl)-8-ethyl-9H-purine-6-amine $^1$H NMR (400 MHz, DMSO-d$_6$) δ 8.33 (s, 1H), 7.06-7.02 (m, 3H), 6.95-6.93 (m, 1H), 6.91-6.87 (m, 2H), 4.30 (s, 4H), 4.04 (br.s, 2H), 3.70-3.61 (m, 2H), 3.48-3.45 (m, 4H), 3.12-3.09 (m, 4H), 2.74 (q, J=7.2 Hz, 2H), 2.18 (s, 3H), 2.14 (s, 3H), 1.21 (t, J=7.6 Hz, 3H).
MH+ 514.

Example 61

N-(2-(4-(2,3-dimethylphenyl)piperazin-1-yl)ethyl)-9-(4-methoxyphenyl)-8-methyl-9H-purine-6-amine $^1$H NMR (400 MHz, DMSO-d$_6$) δ 11.13 (br.s, 1H), 9.35 (br.s, 1H), 8.37 (s, 1H), 7.44 (d, J=8.8 Hz, 2H), 7.13 (d, J=8.8 Hz, 2H), 7.03 (t, J=7.6 Hz, 1H), 6.88 (dd, J=8.4, 7.6 Hz, 2H), 4.10 (br.s, 6H), 3.82 (s, 3H), 3.50 (br.s, 4H), 3.33 (br.s, 2H), 3.12-3.10 (m, 4H), 2.44 (s, 3H), 2.18 (s, 3H), 2.14 (s, 3H).
MH+ 472.

Example 62

N-(3-(4-(2,3-dimethylphenyl)piperazin-1-yl)propyl)-9-(4-methoxyphenyl)-8-methyl-9H-purine-6-amine $^1$H NMR (400 MHz, DMSO-d$_6$) δ 11.26 (br.s, 1H), 9.76 (br.s, 1H), 8.33 (s, 1H), 7.45 (d, J=9.2 Hz, 2H), 7.15 (d, J=2.8 Hz, 2H), 7.03 (t, J=7.6 Hz, 1H), 6.88 (dd, J=7.6, 8.0 Hz, 2H), 4.23 (br.s, 2H), 3.82 (s, 3H), 3.74 (br.s, 4H), 3.50 (br.s, 4H), 3.26 (br.s, 4H), 3.15-3.08 (m, 6H), 2.43 (s, 3H), 2.18 (s, 3H), 2.13 (s, 3H).
MH+ 486.

Example 63

1-(4-(2,3-dimethylphenyl)piperazin-1-yl)-3-(9-(4-methoxyphenyl)-8-methyl-9H-purin-6-ylamino)propan-2-ol $^1$H NMR (400 MHz, DMSO-d$_6$) δ 10.62 (br.s, 1H), 9.66 (br.s, 1H), 8.33 (s, 1H), 7.45 (d, J=8.8 Hz, 2H), 7.14 (d, J=6.8 Hz, 2H), 7.03 (t, J=7.6 Hz, 1H), 6.88 (dd, J=7.6, 8.0 Hz, 2H), 4.41 (br.s, 2H), 3.82 (s, 3H), 3.75-3.72 (m, 2H), 3.67-3.60 (m, 2H), 3.28-3.23 (m, 4H), 3.17-3.08 (m, 4H), 2.44 (s, 3H), 2.18 (s, 3H), 2.13 (s, 3H).
MH+ 502.

Example 64

N-(2-(4-(2,3-dimethylphenyl)piperazin-1-yl)ethyl)-8-ethyl-9-(4-methoxyphenyl)-9H-purine-6-amine $^1$H NMR (400 MHz, DMSO-d$_6$) δ 9.07 (br.s, 1H), 8.33 (s, 1H), 7.42 (d, J=8.4 Hz, 2H), 7.12 (d, J=9.2 Hz, 2H), 7.04 (t, J=7.6 Hz, 1H), 6.89 (dd, J=6.4, 7.6 Hz, 2H), 4.06 (br.s, 2H), 3.82 (s, 3H), 3.49 (br.s, 4H), 3.41-3.37 (m, 2H), 3.10 (br.s, 4H), 2.73 (q, J=7.6 Hz, 2H), 2.18 (s, 3H), 2.14 (s, 3H), 1.21 (t, J=7.6 Hz, 3H).
MH+ 486.

Example 65

N-(3-(4-(2,3-dimethylphenyl)piperazin-1-yl)propyl)-8-ethyl-9-(4-methoxyphenyl)-9H-purine-6-amine $^1$H NMR (400 MHz, DMSO-$d_6$) δ 11.26 (br.s, 1H), 9.71 (br.s, 1H), 8.33 (s, 1H), 7.44 (d, J=9.2 Hz, 2H), 7.13 (d, J=6.8 Hz, 2H), 7.03 (t, J=7.6 Hz, 1H), 6.89 (dd, J=7.6, 8.0 Hz, 2H), 3.82 (s, 3H), 3.75 (br.s, 2H), 3.50 (br.s, 2H), 3.27 (br.s, 4H), 3.16-3.08 (m, 6H), 2.74 (q, J=7.2 Hz, 2H), 2.18 (s, 3H), 2.13 (s, 3H), 1.21 (t, J=7.2 Hz, 3H).
MH+ 500.

Example 66

1-(4-(2,3-dimethylphenyl)piperazin-1-yl)-3-(8-ethyl-9-(4-methoxyphenyl)-9H-purin-6-ylamino)propan-2-ol $^1$H NMR (400 MHz, DMSO-$d_6$) δ 10.57 (br.s, 1H), 9.48 (br.s, 1H), 8.32 (s, 1H), 7.44 (d, J=8.8 Hz, 2H), 7.13 (d, J=6.4 Hz, 2H), 7.03 (t, J=7.6 Hz, 1H), 6.89 (dd, J=7.6, 8.4 Hz, 2H), 4.41 (br.s, 1H), 3.82 (s, 3H), 3.74 (br.s, 2H), 3.64-3.54 (m, 2H), 3.26-3.20 (m, 4H), 3.17-3.08 (m, 4H), 2.74 (q, J=7.2 Hz, 2H), 2.18 (s, 3H), 2.13 (s, 3H), 1.21 (t, J=7.2 Hz, 3H).
MH+ 516.

Example 67

N-(3-(4-(3-chloro-2-methylphenyl)piperazin-1-yl)propyl)-8,9-diphenyl-9H-purine-6-amine $^1$H NMR (400 MHz, DMSO-$d_6$) δ 11.13 (br.s, 1H), 8.35 (s, 1H), 7.53-7.52 (m, 3H), 7.48-7.46 (m, 2H), 7.44-7.34 (m, 5H), 7.20-7.14 (m, 1H), 7.02-7.01 (m, 2H), 3.75 (br.s, 2H), 3.52 (br.s, 2H), 3.27 (br.s, 2H), 3.15 (br.s, 6H), 2.26 (s, 3H), 2.17 (br.s, 2H).
MH+ 538.

Example 68

N-(4-(4-(2,3-dimethylphenyl)piperazin-1-yl)butyl)-8,9-diphenyl-9H-purine-6-amine $^1$H NMR (400 MHz, DMSO-$d_6$) δ 10.86 (br.s, 1H), 9.38 (br.s, 3H), 8.33 (s, 1H), 7.52-7.51 (m, 3H), 7.47-7.46 (m, 2H), 7.43-7.34 (m, 5H), 7.05-7.02 (m, 1H), 6.90-6.85 (m, 2H), 3.67 (br.s, 2H), 3.51-3.48 (m, 2H), 3.17-3.13 (m, 4H), 3.08 (br.s, 4H), 2.18 (s, 3H), 2.13 (s, 3H), 1.86 (br.s, 2H), 1.71 (br.s, 3H).
MH+ 532.

Example 69

9-(4-chlorophenyl)-N-(2-(4-(2,3-dimethylphenyl)piperazin-1-yl)ethyl)-8-methyl-9H-purine-6-amine $^1$H NMR (400 MHz, DMSO-$d_6$) δ 8.34 (s, 1H), 7.69 (d, J=6.8 Hz, 2H), 7.59 (d, J=2.4 Hz, 2H), 7.03 (t, J=7.6 Hz, 1H), 6.88 (dd, J=7.2, 8.0 Hz, 2H), 4.08 (br.s, 2H), 3.48 (s, 2H), 3.33 (br.s, 4H), 3.10 (br.s, 4H), 2.46 (s, 3H), 2.18 (s, 3H), 2.14 (s, 3H).
MH+ 476.

Example 70

9-(4-chlorophenyl)-N-(3-(4-(2,3-dimethylphenyl)piperazin-1-yl)propyl)-8-methyl-9H-purine-6-amine $^1$H NMR (400 MHz, DMSO-$d_6$) δ 10.91 (br.s, 1H), 8.30 (s, 1H), 7.69 (d, J=6.4 Hz, 2H), 7.57 (d, J=9.6 Hz, 2H), 7.03 (t, J=8.0 Hz, 1H), 6.88 (d, J=8.0 Hz, 2H), 3.64 (s, 2H), 3.52 (br.s, 2H), 3.24 (br.s, 4H), 3.08 (br.s, 4H), 2.44 (s, 3H), 2.18 (s, 3H), 2.13 (s, 3H).
MH+ 490.

Example 71

1-(9-(4-chlorophenyl)-8-methyl-9H-purin-6-ylamino)-3-(4-(2,3-dimethylphenyl)piperazin-1-yl)propan-2-ol $^1$H NMR (400 MHz, DMSO-$d_6$) δ 10.53 (br.s, 1H), 8.32 (s, 1H), 7.71-7.68 (m, 2H), 7.61-7.59 (m, 2H), 7.03 (dd, J=8.0, 7.6 Hz, 1H), 6.88 (dd, J=7.2, 8.0 Hz, 2H), 4.42 (br.s, 1H), 3.76 (br.s, 2H), 3.62-3.54 (m, 2H), 3.28 (br.s, 4H), 3.12-3.08 (m, 4H), 2.46 (s, 3H), 2.18 (s, 3H), 2.13 (s, 3H).
MH+ 506.

Example 72

9-(4-chlorophenyl)-N-(2-(4-(2,3-dimethylphenyl)piperazin-1-yl)ethyl)-8-ethyl-9H-purine-6-amine 1H NMR (400 MHz, DMSO-$d_6$) δ 8.31 (s, 1H), 7.70-7.67 (m, 2H), 7.58-7.55 (m, 2H), 7.03 (t, J=7.6 Hz, 1H), 6.88 (dd, J=6.8, 7.6 Hz, 2H), 4.08 (br.s, 2H), 3.47 (s, 2H), 3.33 (br.s, 4H), 3.12 (br.s, 4H), 2.75 (q, J=7.2 Hz, 2H), 2.18 (s, 3H), 2.14 (s, 3H), 1.21 (t, J=7.6 Hz, 3H).
MH+ 490.

Example 73

9-(4-chlorophenyl)-N-(3-(4-(2,3-dimethylphenyl)piperazin-1-yl)propyl)-8-ethyl-9H-purine-6-amine $^1$H NMR (400 MHz, DMSO-$d_6$) δ 11.10 (br.s, 1H), 8.33 (s, 1H), 7.72-7.68 (m, 2H), 7.60-7.56 (m, 2H), 7.03 (dd, J=8.0, 7.6 Hz, 1H), 6.88 (dd, J=7.6, 8.0 Hz, 2H), 4.08 (br.s, 2H), 3.72 (s, 2H), 3.50 (br.s, 2H), 3.25-3.08 (m, 8H), 2.74 (q, J=7.6 Hz, 2H), 2.18 (s, 3H), 2.13 (s, 3H), 1.22 (t, J=7.6 Hz, 3H).
MH+ 504.

Example 74

1-(9-(4-chlorophenyl)-8-ethyl-9H-purin-6-ylamino)-3-(4-(2,3-dimethylphenyl)piperazin-1-yl)propan-2-ol $^1$H NMR (400 MHz, DMSO-$d_6$) δ 10.60 (br.s, 1H), 9.50 (br.s, 1H), 8.33 (s, 1H), 7.72-7.67 (m, 2H), 7.60-7.56 (m, 2H), 7.03 (dd, J=8.0, 7.6 Hz, 1H), 6.88 (dd, J=7.6, 8.0 Hz, 2H), 4.41 (br.s, 1H), 3.74-3.54 (m, 2H), 3.45-3.38 (m, 2H), 3.28-3.17 (m, 4H), 3.13-3.02 (m, 4H), 2.76 (q, J=7.6 Hz, 2H), 2.18 (s, 3H), 2.13 (s, 3H), 1.22 (t, J=7.6 Hz, 3H).
MH+ 520.

Example 75

N-(2-(4-(2,3-dimethylphenyl)piperazin-1-yl)ethyl)-8-methyl-9-(4-(trifluoromethyl)phenyl)-9H-purine-6-amine $^1$H NMR (400 MHz, DMSO-$d_6$) δ 11.26 (br.s, 1H), 9.35 (br.s, 1H), 8.37 (s, 1H), 8.01 (d, J=8.4 Hz, 2H), 7.81 (d, J=8.4

Hz, 2H), 7.03 (dd, J=7.6, 8.0 Hz, 1H), 6.88 (dd, J=7.6, 7.2 Hz, 2H), 4.12 (br.s, 2H), 3.64 (s, 2H), 3.50 (br.s, 2H), 3.33 (br.s, 2H), 3.17 (br.s, 4H), 2.50 (s, 3H), 2.18 (s, 3H), 2.14 (s, 3H).
MH+ 510.

Example 76

N-(3-(4-(2,3-dimethylphenyl)piperazin-1-yl)propyl)-8-methyl-9-(4-(trifluoromethyl)phenyl)-9H-purine-6-amine $^1$H NMR (400 MHz, DMSO-d$_6$) δ 11.34 (br.s, 1H), 9.90 (br.s, 1H), 8.36 (s, 1H), 8.02 (d, J=8.4 Hz, 2H), 7.81 (d, J=8.4 Hz, 2H), 7.04 (dd, J=7.6, 8.0 Hz, 1H), 6.88 (dd, J=7.6, 8.4 Hz, 2H), 4.12 (br.s, 2H), 3.77 (s, 2H), 3.49 (br.s, 2H), 3.29-3.26 (m, 2H), 3.17 (br.s, 4H), 2.49 (s, 3H), 2.18 (s, 3H), 2.14 (s, 3H).
MH+ 524.

Example 77

N-(2-(4-(2,3-dimethylphenyl)piperazin-1-yl)ethyl)-8-ethyl-9-(4-(trifluoromethyl)phenyl)-9H-purine-6-amine $^1$H NMR (400 MHz, DMSO-d$_6$) δ 11.15 (br.s, 1H), 9.30 (br.s, 1H), 8.44 (s, 1H), 8.05 (d, J=8.8 Hz, 2H), 7.80 (d, J=8.4 Hz, 2H), 7.03 (dd, J=7.6, 8.0 Hz, 1H), 6.88 (t, J=7.2 Hz, 2H), 4.11 (br.s, 2H), 3.65 (s, 2H), 3.50 (br.s, 2H), 3.33 (br.s, 2H), 3.17 (br.s, 4H), 2.80 (q, J=7.6 Hz, 2H), 2.18 (s, 3H), 2.14 (s, 3H), 1.23 (t, J=7.2 Hz, 3H).
MH+ 524.

Example 78

N-(3-(4-(2,3-dimethylphenyl)piperazin-1-yl)propyl)-8-ethyl-9-(4-(trifluoromethyl)phenyl)-9H-purine-6-amine $^1$H NMR (400 MHz, DMSO-d$_6$) δ 11.27 (br.s, 1H), 9.67 (br.s, 1H), 8.34 (s, 1H), 8.23 (d, J=8.8 Hz, 2H), 7.80 (d, J=8.4 Hz, 2H), 7.03 (t, J=7.6 Hz, 1H), 6.87 (dd, J=7.6, 8.0 Hz, 2H), 4.21 (br.s, 2H), 3.76 (s, 2H), 3.50 (br.s, 2H), 3.26 (br.s, 2H), 3.16-3.08 (m, 6H), 2.79 (q, J=7.2 Hz, 2H), 2.18 (s, 3H), 2.14 (s, 3H), 1.23 (t, J=7.6 Hz, 3H).
MH+ 538.

Example 79

N-(3-(4-(2,3-dimethylphenyl)piperazin-1-yl)propyl)-9-(4-fluorophenyl)-8-phenyl-9H-purine-6-amine $^1$H NMR (400 MHz, DMSO-d$_6$) δ 11.06 (br.s, 1H), 8.36 (s, 1H), 7.50-7.45 (m, 3H), 7.44-7.36 (m, 4H), 7.03 (t, J=7.6 Hz, 2H), 6.87 (dd, J=7.2, 11.2 Hz, 3H), 3.74 (br.s, 2H), 3.53-3.51 (m, 2H), 3.26 (br.s, 4H), 3.17-3.08 (m, 6H), 2.18 (s, 3H), 2.13 (s, 3H).
MH+ 536.

Example 80

9-(4-chlorophenyl)-N-(3-(4-(2,3-dimethylphenyl)piperazin-1-yl)propyl)-8-phenyl-9H-purine-6-amine $^1$H NMR (400 MHz, DMSO-d$_6$) δ 10.61 (br.s, 1H), 8.30 (s, 1H), 7.59 (d, J=8.8 Hz, 2H), 7.48-7.36 (m, 5H), 7.03 (t, J=7.6 Hz, 2H), 6.87 (dd, J=7.6, 11.2 Hz, 3H), 3.82 (br.s, 2H), 3.53-3.51 (m, 2H), 3.24 (br.s, 4H), 3.19-3.07 (m, 6H), 2.18 (s, 3H), 2.13 (s, 3H).
MH+ 552.

Example 81

N-(3-(4-(2,3-dimethylphenyl)piperazin-1-yl)propyl)-9-(4-methoxyphenyl)-8-phenyl-9H-purine-6-amine $^1$H NMR (400 MHz, DMSO-d$_6$) δ 10.64 (br.s, 1H), 8.30 (s, 1H), 7.49 (d, J=6.8 Hz, 2H), 7.43-7.35 (m, 3H), 7.29 (d, J=8.8 Hz, 2H), 7.03 (dd, J=9.2, 7.6 Hz, 3H), 6.88 (dd, J=8.0, 10.4 Hz, 2H), 3.79 (s, 3H), 3.69 (br.s, 2H), 3.60-3.51 (m, 2H), 3.25-3.20 (m, 4H), 3.13-3.07 (m, 6H), 2.18 (s, 3H), 2.13 (s, 3H).
MH+ 548.

Example 82

N-(3-(4-(2,3-dimethylphenyl)piperazin-1-yl)propyl)-8-phenyl-9-(4-(trifluoromethyl)phenyl)-9H-purine-6-amine $^1$H NMR (400 MHz, DMSO-d$_6$) δ 10.89 (br.s, 1H), 8.32 (s, 1H), 7.91 (d, J=8.4 Hz, 2H), 7.62 (d, J=8.4 Hz, 2H), 7.47-7.37 (m, 5H), 7.03 (t, J=7.6 Hz, 1H), 6.87 (dd, J=7.2, 11.2 Hz, 2H), 3.70 (br.s, 2H), 3.53-3.51 (m, 2H), 3.25 (br.s, 4H), 3.18-3.08 (m, 6H), 2.18 (s, 3H), 2.13 (s, 3H).
MH+ 586.

Example 83

9-(benzo[d][1,3]dioxol-5-yl)-N-(3-(4-(2,3-dimethylphenyl)piperazin-1-yl)propyl)-8-phenyl-9H-purine-6-amine $^1$H NMR (400 MHz, DMSO-d$_6$) δ 11.07 (br.s, 1H), 8.37 (s, 1H), 7.54 (d, J=6.8 Hz, 2H), 7.46-7.38 (m, 3H), 7.08-7.02 (m, 3H), 6.90-6.84 (m, 3H), 6.13 (s, 2H), 3.75 (br.s, 2H), 3.51 (br.s, 2H), 3.26 (br.s, 4H), 3.17-3.08 (m, 6H), 2.18 (s, 3H), 2.13 (s, 3H).
MH+ 562.

Example 84

9-(2,3-dihydrobenzo[b][1,4]dioxin-6-yl)-N-(3-(4-(2,3-dimethylphenyl)piperazin-1-yl)propyl)-8-phenyl-9H-purine-6-amine $^1$H NMR (400 MHz, DMSO-d$_6$) δ 10.96 (br.s, 1H), 8.35 (s, 1H), 7.53 (d, J=6.8 Hz, 2H), 7.46-7.37 (m, 3H), 7.05-6.95 (m, 3H), 6.90-6.79 (m, 3H), 4.27 (q, J=4.8 Hz, 4H), 3.73 (br.s, 2H), 3.51 (br.s, 2H), 3.26 (br.s, 4H), 3.18-3.08 (m, 6H), 2.18 (s, 3H), 2.13 (s, 3H).
MH+ 576.

Example 85

N-(2-(4-(2,3-dimethylphenyl)piperazin-1-yl)ethyl)-8-methyl-9-(4-(methylthio)phenyl)-9H-purine-6-amine hydrochloride $^1$H NMR (400 MHz, DMSO-d$_6$) δ 11.10 (s, 1H), 9.36 (s, 1H), 8.37 (s, 1H), 7.51-7.46 (m, 4H), 7.04 (dd, J=7.2, 7.6 Hz, 1H), 6.88 (dd, J=7.2, 8.0 Hz, 2H), 4.12-4.10 (m, 2H), 3.69-

3.64 (m, 2H), 3.58-3.48 (m, 4H), 3.36-3.32 (m, 2H), 3.12 (s, 3H), 3.11-3.08 (m, 2H), 2.53 (s, 3H), 2.18 (s, 3H), 2.14 (s, 3H).
MH+ 488 (—HCl).

Example 86

N-(3-(4-(2,3-dimethylphenyl)piperazin-1-yl)propyl)-8-methyl-9-(4-(methylthio)phenyl)-9H-purine-6-amine hydrochloride $^1$H NMR (400 MHz, DMSO-$d_6$) δ 11.29 (s, 1H), 9.78 (s, 1H), 8.34 (s, 1H), 7.51-7.46 (m, 4H), 7.03 (dd, J=7.2, 7.6 Hz, 1H), 6.88 (dd, J=7.6, 8.0 Hz, 2H), 4.14-4.12 (m, 2H), 3.14-3.12 (m, 2H), 3.58-3.50 (m, 2H), 3.29-3.24 (m, 2H), 3.16-3.08 (m, 6H), 2.53 (s, 3H), 2.45 (s, 3H), 2.18 (s, 3H), 2.13 (s, 3H).
MH+ 502 (—HCl).

Example 87

N-(2-(4-(2,3-dimethylphenyl)piperazin-1-yl)ethyl)-8-ethyl-9-(4-(methylthio)phenyl)-9H-purine-6-amine hydrochloride $^1$H NMR (400 MHz, DMSO-$d_6$) δ 11.08 (s, 1H), 9.34 (s, 1H), 8.36 (s, 1H), 7.50-7.47 (m, 4H), 7.03 (dd, J=7.6, 7.6 Hz, 1H), 6.88 (dd, J=7.2, 8.0 Hz, 2H), 4.11-4.08 (m, 2H), 3.69-3.64 (m, 2H), 3.52-3.46 (m, 2H), 3.34-3.30 (m, 2H), 2.76 (q, J=7.6 Hz, 2H), 2.52 (s, 3H), 2.18 (s, 3H), 2.14 (s, 3H) 1.22 (t, J=7.6 Hz, 3H).
MH+ 502 (—HCl).

Example 88

N-(3-(4-(2,3-dimethylphenyl)piperazin-1-yl)propyl)-8-ethyl-9-(4-(methylthio)phenyl)-9H-purine-6-amine hydrochloride $^1$H NMR (400 MHz, DMSO-$d_6$) δ 11.26 (s, 1H), 9.80 (s, 1H), 8.44 (s, 1H), 7.48-7.46 (m, 4H), 7.03 (dd, J=7.2, 7.6 Hz, 1H), 6.87 (dd, J=7.2, 8.0 Hz, 2H), 3.76-3.73 (m, 2H), 3.52-3.49 (m, 2H), 3.27-3.23 (m, 2H), 3.19-3.15 (m, 4H), 3.12-3.06 (m, 4H), 2.75 (q, J=7.2 Hz, 2H), 2.52 (s, 3H), 2.17 (s, 3H), 2.13 (s, 3H) 1.22 (t, J=7.2 Hz, 3H).
MH+ 516 (—HCl).

Example 89

N-(2-(4-(2,3-dimethylphenyl)piperazin-1-yl)ethyl)-9-(4-(methylthio)phenyl)-8-phenyl-9H-purine-6-amine hydrochloride $^1$H NMR (400 MHz, DMSO-$d_6$) δ 10.69 (s, 1H), 8.84 (s, 1H), 8.33 (s, 1H), 7.51-7.50 (m, 2H), 7.43-7.36 (m, 5H), 7.32-7.29 (m, 2H), 7.04 (dd, J=7.6, 7.6 Hz, 1H), 6.89 (dd, J=7.2, 8.0 Hz, 2H), 4.05-4.02 (m, 2H), 3.67-3.60 (m, 2H), 3.52-3.49 (m, 2H), 3.36-3.31 (m, 2H), 3.11-3.08 (m, 4H), 2.50 (s, 3H), 2.18 (s, 3H), 2.14 (s, 3H).
MH+ 550 (—HCl).

Example 90

N-(3-(4-(2,3-dimethylphenyl)piperazin-1-yl)propyl)-9-(4-(methylthio)phenyl)-8-phenyl-9H-purine-6-amine hydrochloride $^1$H NMR (400 MHz, DMSO-$d_6$) δ 11.01 (s, 1H), 8.35 (s, 1H), 7.51-7.50 (m, 2H), 7.46-7.37 (m, 5H), 7.33-7.31 (m, 2H), 7.04 (dd, J=7.6, 7.6 Hz, 1H), 6.88 (dd, J=7.6, 11.2 Hz, 2H), 3.76-3.73 (m, 2H), 3.52-3.49 (m, 2H), 3.29-3.26 (m, 2H), 3.17-3.13 (m, 4H), 3.09-3.05 (m, 4H), 2.50 (s, 3H), 2.18 (s, 3H), 2.13 (s, 3H).
MH+ 564 (—HCl).

Example 91

N-(2-(4-(2,3-dimethylphenyl)piperazin-1-yl)ethyl)-9-phenyl-8-(thiophen-2-yl)-9H-purine-6-amine hydrochloride $^1$H NMR (400 MHz, DMSO-$d_6$) δ 10.60 (s, 1H), 8.71 (s, 1H), 8.28 (s, 1H), 7.70 (d, J=4.4 Hz, 1H), 7.65-7.63 (m, 2H), 7.52-7.50 (m, 2H), 7.06-6.99 (m, 2H), 6.89 (dd, J=6.0, 6.4 Hz, 2H), 6.73 (d, J=2.0 Hz, 1H), 4.04-4.01 (m, 2H), 3.72-3.70 (m, 2H), 3.53-3.49 (m, 2H), 3.38-3.35 (m, 2H), 3.15-3.08 (m, 4H), 2.18 (s, 3H), 2.14 (s, 3H).
MH+ 510 (—HCl).

Example 92

N-(3-(4-(2,3-dimethylphenyl)piperazin-1-yl)propyl)-9-phenyl-8-(thiophen-2-yl)-9H-purine-6-amine hydrochloride $^1$H NMR (400 MHz, DMSO-$d_6$) δ 11.28 (s, 1H), 8.34 (s, 1H), 7.74 (d, J=4.8 Hz, 1H), 7.69-7.62 (m, 2H), 7.56-7.54 (m, 2H), 7.06-7.01 (m, 2H), 6.87 (dd, J=7.6, 8.0 Hz, 2H), 6.78 (d, J=2.4 Hz, 1H), 3.80-3.76 (m, 2H), 3.53-3.49 (m, 2H), 3.32-3.28 (m, 2H), 3.20-3.16 (m, 4H), 3.13-3.08 (m, 4H), 2.18 (s, 3H), 2.13 (s, 3H).
MH+ 524 (—HCl).

Example 93

8-cyclopentyl-N-(2-(4-(2,3-dimethylphenyl)piperazin-1-yl)ethyl)-9-phenyl-9H-purine-6-amine hydrochloride $^1$H NMR (400 MHz, DMSO-$d_6$) δ 10.70 (s, 1H), 8.29 (s, 1H), 7.64-7.56 (m, 3H), 7.50-7.47 (m, 2H), 7.04 (dd, J=7.6, 7.6 Hz, 1H), 6.89 (dd, J=6.8, 7.6 Hz, 2H), 4.05-4.01 (m, 2H), 3.80-3.76 (m, 2H), 3.69-3.65 (m, 2H), 3.50-3.46 (m, 2H), 3.18-3.12 (m, 5H), 2.18 (s, 3H), 2.14 (s, 3H), 1.91-1.81 (m, 4H), 1.74-1.65 (m, 2H), 1.56-1.50 (m, 2H).
MH+ 495 (—HCl).

Example 94

N-(2-(4-(2,3-dimethylphenyl)piperazin-1-yl)ethyl)-8-phenyl-9-propyl-9H-purine-6-amine hydrochloride $^1$H NMR (400 MHz, DMSO-$d_6$) δ 9.49 (s, 1H), 8.53 (s, 1H), 7.94-7.80 (m, 2H), 7.64-7.62 (m, 3H), 7.06 (dd, J=8.0, 7.6 Hz, 1H), 6.94-6.92 (m, 2H), 4.51-4.16 (m, 4H), 3.76-3.55 (m, 4H), 3.45-3.36 (m, 2H), 3.26-3.10 (m, 4H), 2.22 (s, 3H), 2.17 (s, 3H), 1.69 (q, J=7.2 Hz, 2H), 0.74 (t, J=7.2 Hz, 3H).
MH+ 469 (—HCl).

Example 95

N-(4-(4-(2,3-dimethylphenyl)piperazin-1-yl)butyl)-9-(4-methoxyphenyl)-8-phenyl-9H-purine-6-amine hydrochloride $^1$H NMR (400 MHz, DMSO-$d_6$) δ 11.13 (s, 1H), 8.39 (s, 1H), 7.54 (d, J=7.2 Hz, 2H), 7.49-7.36 (m, 5H), 7.11-7.05 (m, 3H), 6.94-6.89 (m, 2H), 3.83 (s, 3H), 3.76-3.73 (m, 2H), 3.57-3.43 (m, 2H), 3.20-3.17 (m, 4H), 3.16-3.05 (m, 4H), 2.22 (s, 3H), 2.16 (s, 3H), 2.01-1.92 (m, 2H), 1.84-1.68 (m, 2H).
MH+ 561 (—HCl).

Example 96

N-(4-(4-(2,3-dimethylphenyl)piperazin-1-yl)butyl)-9-(4-(methylthio)phenyl)-8-phenyl-9H-purine-6-amine hydrochloride $^1$H NMR (400 MHz, DMSO-d$_6$) δ 11.15 (s, 1H), 9.84 (s, 1H), 8.39 (s, 1H), 7.54 (d, J=6.8 Hz, 2H), 7.49-7.36 (m, 5H), 7.12-7.09 (m, 2H), 6.94-6.89 (m, 3H), 3.75-3.74 (m, 2H), 3.55-3.51 (m, 2H), 3.20-3.18 (m, 4H), 3.16-3.11 (m, 4H), 2.53 (s, 3H), 2.22 (s, 3H), 2.16 (s, 3H), 1.94-1.91 (m, 2H), 1.83-1.76 (m, 2H).
MH+ 577 (—HCl).

Example 97

N-(4-(4-(2,3-dimethylphenyl)piperazin-1-yl)butyl)-9-(4-fluorophenyl)-8-phenyl-9H-purine-6-amine hydrochloride $^1$H NMR (400 MHz, DMSO-d$_6$) δ 11.36 (s, 1H), 10.15 (s, 1H), 8.43 (s, 1H), 7.57-7.41 (m, 7H), 7.09-7.05 (m, 2H), 6.94-6.89 (m, 3H), 3.80-3.79 (m, 2H), 3.55-3.51 (m, 2H), 3.20-3.15 (m, 4H), 3.11-3.02 (m, 4H), 2.22 (s, 3H), 2.17 (s, 3H), 1.94-1.91 (m, 2H), 1.79-1.77 (m, 2H).
MH+ 549 (—HCl).

Example 98

9-(2,3-dihydrobenzo[b][1,4]dioxin-6-yl)-N-(4-(4-(2,3-dimethylphenyl)piperazin-1-yl)butyl)-8-phenyl-9H-purine-6-amine hydrochloride $^1$H NMR (400 MHz, DMSO-d$_6$) δ 11.30 (s, 1H), 10.11 (s, 1H), 8.41 (s, 1H), 7.58-7.42 (m, 6H), 7.09-7.00 (m, 2H), 6.94-6.86 (m, 3H), 4.33-4.29 (m, 4H), 3.79-3.77 (m, 2H), 3.54-3.51 (m, 2H), 3.21-3.14 (m, 4H), 3.11-3.06 (m, 4H), 2.22 (s, 3H), 2.17 (s, 3H), 1.93-1.84 (m, 2H), 1.78-1.77 (m, 2H).
MH+ 589 (—HCl).

Example 99

N-(4-(4-(2,3-dimethylphenyl)piperazin-1-yl)butyl)-8-phenyl-9-(4-(trifluoromethyl)phenyl)-9H-purine-6-amine hydrochloride $^1$H NMR (400 MHz, DMSO-d$_6$) δ 11.28 (s, 1H), 9.95 (s, 1H), 8.42 (s, 1H), 7.97 (d, J=8.4 Hz, 2H), 7.73 (d, J=13.6 Hz, 2H), 7.65-7.42 (m, 3H), 7.09-7.05 (m, 2H), 6.94-6.89 (m, 3H), 3.78-3.77 (m, 2H), 3.53-3.51 (m, 2H), 3.21-3.14 (m, 4H), 3.11-3.06 (m, 4H), 2.22 (s, 3H), 2.17 (s, 3H), 1.93-1.85 (m, 2H), 1.78-1.77 (m, 2H).
MH+ 599 (—HCl).

Example 100

N-(3-(4-(2,3-dimethylphenyl)piperazin-1-yl)propyl)-N-methyl-8,9-diphenyl-9H-purine-6-amine hydrochloride $^1$H NMR (400 MHz, DMSO-d$_6$) δ 11.06 (s, 1H), 8.31 (s, 1H), 7.58-7.51 (m, 5H), 7.44-7.35 (m, 5H), 7.06 (dd, J=7.6, 8.0 Hz, 1H), 6.93 (d, J=7.2 Hz, 1H), 6.86 (d, J=7.2 Hz, 1H), 3.59-3.56 (m, 4H), 3.39-3.37 (m, 2H), 3.28-3.20 (m, 4H), 3.18-3.06 (m, 4H), 2.28 (br.s, 3H), 2.22 (s, 3H), 2.17 (s, 3H).
MH+ 531 (—HCl).

Example 101

N-(3-(4-(3-chloro-2-methylphenyl)piperazin-1-yl)propyl)-N-methyl-8,9-diphenyl-9H-purine-6-amine hydrochloride $^1$H NMR (400 MHz, DMSO-d$_6$) δ 11.52 (s, 1H), 8.36 (s, 1H), 7.60-7.52 (m, 5H), 7.45-7.36 (m, 5H), 7.23-7.17 (m, 2H), 7.01 (d, J=6.4 Hz, 1H), 3.59-3.56 (m, 2H), 3.39-3.37 (m, 2H), 3.29-3.20 (m, 4H), 3.17-3.06 (m, 6H), 2.32 (br.s, 3H), 2.28 (s, 3H).
MH+ 552 (—HCl).

Example 102

N-(3-(4-(2,3-dichlorophenyl)piperazin-1-yl)propyl)-N-methyl-8,9-diphenyl-9H-purine-6-amine hydrochloride $^1$H NMR (400 MHz, DMSO-d$_6$) δ 11.58 (s, 1H), 8.34 (s, 1H), 7.59-7.52 (m, 5H), 7.45-7.33 (m, 6H), 7.17-7.16 (m, 2H), 3.63-3.60 (m, 4H), 3.46-3.43 (m, 2H), 3.33-3.28 (m, 4H), 3.25-3.06 (m, 4H), 2.31 (br.s, 3H).
MH+ 572 (—HCl).

Example 103

(S)-1-(4-(2,3-dimethylphenyl)piperazin-1-yl)-3-(8,9-diphenyl-9H-purin-6-ylamino)propan-2-ol hydrochloride $^1$H NMR (400 MHz, DMSO-d$_6$) δ 10.73 (s, 1H), 9.83 (br.s, 1H), 8.41 (s, 1H), 7.52-7.43 (m, 5H), 7.37-7.31 (m, 5H), 7.06 (dd, J=7.6, 8.0 Hz, 1H), 6.92-6.89 (m, 2H), 6.36 (br.s, 1H), 4.21 (br.s, 1H), 4.11-4.09 (m, 1H), 3.95 (br.s, 1H), 3.79-3.75 (m, 1H), 2.92-2.82 (m, 4H), 2.68 (br.s, 2H), 2.63-2.57 (m, 4H), 2.26 (s, 3H), 2.21 (s, 3H).
MH+ 533 (—HCl).

Example 104

(S)-1-(4-(3-chloro-2-methylphenyl)piperazin-1-yl)-3-(8,9-diphenyl-9H-purin-6-ylamino)propan-2-ol hydrochloride $^1$H NMR (400 MHz, DMSO-d$_6$) δ 10.84 (s, 1H), 9.91 (br.s, 1H), 8.42 (s, 1H), 7.59-7.49 (m, 5H), 7.47-7.39 (m, 5H), 7.23-7.17 (m, 2H), 7.06-7.04 (m, 1H), 4.58-4.52 (m, 1H), 3.87-3.81 (m, 2H), 3.70-3.50 (m, 4H), 3.35-2.26 (m, 4H), 3.20-3.16 (m, 2H), 2.30 (s, 3H).
MH+ 554 (—HCl).

Example 105

(S)-1-(4-(2,3-dichlorophenyl)piperazin-1-yl)-3-(8,9-diphenyl-9H-purin-6-ylamino)propan-2-ol hydrochloride $^1$H NMR (400 MHz, DMSO-d$_6$) δ 10.75 (br.s, 1H), 9.32 (br.s, 1H), 8.34 (s, 1H), 7.51-7.44 (m, 5H), 7.39-7.29 (m, 5H), 7.21-7.08 (m, 2H), 6.96-6.94 (m, 1H), 6.39 (br.s, 1H), 4.14-

4.12 (m, 1H), 3.98-3.94 (m, 1H), 3.79-3.77 (m, 1H), 3.11 (br.s, 4H), 2.89-2.87 (m, 2H), 2.72 (br.s, 2H), 2.63 (d, J=6.8 Hz, 2H).
MH+ 574 (—HCl).

Example 106

(R)-1-(4-(2,3-dimethylphenyl)piperazin-1-yl)-3-(8,9-diphenyl-9H-purin-6-ylamino)propan-2-ol hydrochloride $^1$H NMR (400 MHz, DMSO-d$_6$) δ 10.73 (s, 1H), 9.83 (br.s, 1H), 8.41 (s, 1H), 7.52-7.43 (m, 5H), 7.37-7.31 (m, 5H), 7.06 (dd, J=7.6, 8.0 Hz, 1H), 6.92-6.89 (m, 2H), 6.36 (br.s, 1H), 4.21 (br.s, 1H), 4.11-4.09 (m, 1H), 3.95 (br.s, 1H), 3.79-3.75 (m, 1H), 2.92-2.82 (m, 4H), 2.68 (br.s, 2H), 2.63-2.57 (m, 4H), 2.26 (s, 3H), 2.21 (s, 3H).
MH+ 533 (—HCl).

Example 107

(R)-1-(4-(3-chloro-2-methylphenyl)piperazin-1-yl)-3-(8,9-diphenyl-9H-purin-6-ylamino)propan-2-ol hydrochloride $^1$H NMR (400 MHz, DMSO-d$_6$) δ 10.84 (s, 1H), 9.91 (br.s, 1H), 8.42 (s, 1H), 7.59-7.49 (m, 5H), 7.47-7.39 (m, 5H), 7.23-7.17 (m, 2H), 7.06-7.04 (m, 1H), 4.58-4.52 (m, 1H), 3.87-3.81 (m, 2H), 3.70-3.50 (m, 4H), 3.35-2.26 (m, 4H), 3.20-3.16 (m, 2H), 2.30 (s, 3H).
MH+ 554 (—HCl).

Example 108

(R)-1-(4-(2,3-dichlorophenyl)piperazin-1-yl)-3-(8,9-diphenyl-9H-purin-6-ylamino)propan-2-ol hydrochloride $^1$H NMR (400 MHz, DMSO-d$_6$) δ 10.75 (br.s, 1H), 9.32 (br.s, 1H), 8.34 (s, 1H), 7.51-7.44 (m, 5H), 7.39-7.29 (m, 5H), 7.21-7.08 (m, 2H), 6.96-6.94 (m, 1H), 6.39 (br.s, 1H), 4.14-4.12 (m, 1H), 3.98-3.94 (m, 1H), 3.79-3.77 (m, 1H), 3.11 (br.s, 4H), 2.89-2.87 (m, 2H), 2.72 (br.s, 2H), 2.63 (d, J=6.8 Hz, 2H).
MH+ 574 (—HCl).

Example 109

N-(4-(4-(2,3-dimethylphenyl)piperazin-1-yl)butyl)-9-phenyl-8-(thiophen-2-yl)-9H-purine-6-amine hydrochloride $^1$H NMR (400 MHz, DMSO-d$_6$) δ 11.08 (br.s, 1H), 9.44 (br.s, 1H), 8.32 (s, 1H), 7.74 (d, J=4.4 Hz, 1H), 7.71-7.64 (m, 3H), 7.58-7.57 (m, 2H), 7.09-7.03 (m, 2H), 6.94-6.89 (m, 2H), 6.82 (br.s, 1H), 3.78-3.70 (m, 2H), 3.54-3.52 (m, 2H), 3.20-3.11 (m, 8H), 2.22 (s, 3H), 2.17 (s, 3H), 1.98-1.87 (m, 2H), 1.80-1.72 (m, 2H).
MH+ 537 (—HCl).

Example 110

1-(4-(2,3-dimethylphenyl)piperazin-1-yl)-3-((8,9-diphenyl-9H-purin-6-yl)(methyl)amino)propan-2-ol hydrochloride $^1$H NMR (400 MHz, DMSO-d$_6$) δ 10.95 (br.s, 1H), 8.40 (s, 1H), 7.90-7.53 (m, 5H), 7.46-7.34 (m, 5H), 7.13-7.04 (m, 1H), 6.96-6.73 (m, 2H), 4.52-4.64 (m, 1H), 4.03-4.00 (m, 2H), 3.68-3.40 (m, 4H), 3.37-3.29 (m, 4H), 3.18-3.07 (m, 5H), 2.22 (s, 3H), 2.13 (br. s, 3H).
MH+ 547 (—HCl).

Example 111

1-(4-(3-chloro-2-methylphenyl)piperazin-1-yl)-3-((8,9-diphenyl-9H-purin-6-yl)(methyl)amino)propan-2-ol hydrochloride $^1$H NMR (400 MHz, DMSO-d$_6$) δ 10.94 (br. s, 1H), 8.36 (s, 1H), 7.60-7.52 (m, 5H), 7.46-7.34 (m, 5H), 7.23-7.01 (m, 2H), 6.89-6.87 (m, 1H), 4.68-4.64 (m, 1H), 4.01-3.97 (m, 2H), 3.69-3.59 (m, 4H), 3.47-3.40 (m, 4H), 3.37-3.14 (m, 5H), 2.26 (s, 3H).
MH+ 568 (—HCl).

Example 112

1-(4-(2,3-dichlorophenyl)piperazin-1-yl)-3-((8,9-diphenyl-9H-purin-6-yl)(methyl)amino)propan-2-ol hydrochloride $^1$H NMR (400 MHz, DMSO-d$_6$) δ 10.98 (br. s, 1H), 8.35 (s, 1H), 7.59-7.52 (m, 5H), 7.45-7.32 (m, 7H), 7.22-7.16 (m, 1H), 4.68-4.64 (m, 1H), 4.38-4.33 (m, 2H), 3.98-3.93 (m, 2H), 3.69-3.57 (m, 2H), 3.48-3.45 (m, 2H), 3.37-3.30 (m, 4H), 3.17 (br. s, 3H).
MH+ 588 (—HCl).

Example 113

N-(4-(4-(2,3-dimethylphenyl)piperazin-1-yl)butyl)-N-methyl-8,9-diphenyl-9H-purine-6-amine hydrochloride $^1$H NMR (400 MHz, DMSO-d$_6$) δ 11.50 (br. s, 1H), 8.39 (s, 1H), 7.59-7.52 (m, 5H), 7.47-7.43 (m, 5H), 7.06 (dd, J=7.6, 8.0 Hz, 1H), 6.90 (dd, J=7.2, 7.6 Hz, 2H), 3.46-3.41 (m, 4H), 3.20-3.17 (m, 6H), 3.14-3.04 (m, 6H), 2.21 (s, 3H), 2.15 (s, 3H), 1.93-1.89 (m, 5H).
MH+ 545 (—HCl).

Example 114

4-(4-(2,3-dimethylphenyl)piperazin-1-yl)-1-((8,9-diphenyl-9H-purin-6-yl)(methyl)amino)butan-2-ol hydrochloride $^1$H NMR (400 MHz, DMSO-d$_6$) δ 11.28 (br. s, 1H), 8.40 (s, 1H), 7.59-7.52 (m, 5H), 7.47-7.43 (m, 5H), 7.06 (dd, J=7.6, 8.0 Hz, 1H), 6.94-6.88 (m, 2H), 4.18-4.12 (m, 1H), 3.62-3.52 (m, 4H), 3.41-3.33 (m, 4H), 3.16-3.06 (m, 7H), 2.22 (s, 3H), 2.15 (s, 3H), 1.98-1.91 (m, 2H).
MH+ 561 (—HCl).

Example 115

N-(4-(4-(2,3-dimethylphenyl)piperazin-1-yl)butyl)-N,2-dimethyl-8,9-diphenyl-9H-purine-6-amine hydrochloride $^1$H NMR (400 MHz, DMSO-d$_6$) δ 11.43 (br. s, 1H), 7.58-7.56 (m, 3H), 7.50-7.48 (m, 2H), 7.45-7.37 (m, 5H), 7.06 (dd, J=7.6, 8.0 Hz, 1H), 6.89 (dd, J=7.6, 7.6 Hz, 2H), 4.46-4.41

(m, 2H), 3.44-3.42 (m, 2H), 3.21-3.19 (m, 4H), 3.16-3.10 (m, 4H), 3.07-3.01 (m, 4H), 2.58 (br. s, 3H), 2.22 (s, 3H), 2.14 (s, 3H), 1.90-1.88 (m, 3H).
MH+ 559 (—HCl).

Example 116

N-(4-(4-(2,3-dimethylphenyl)-1,4-diazepan-1-yl)butyl)-8,9-diphenyl-9H-purine-6-amine hydrochloride $^1$H NMR (400 MHz, DMSO-d$_6$) δ 11.41 (br. s, 1H), 10.13 (s, 1H), 8.41 (s, 1H), 7.58-7.42 (m, 5H), 7.41-7.35 (m, 5H), 7.07-7.06 (m, 2H), 6.95-6.50 (m, 1H), 3.80-3.78 (m, 2H), 3.62-3.55 (m, 4H), 3.38-3.32 (m, 2H), 3.28-3.22 (m, 2H), 3.16-3.13 (m, 2H), 2.30-2.14 (m, 8H), 1.96-1.91 (m, 2H), 1.84-1.76 (m, 2H).
MH+ 545 (—HCl).

Example 117

N-(4-(4-(2,3-dimethylphenyl)-1,4-diazepan-1-yl)butyl)-2-methyl-8,9-diphenyl-9H-purine-6-amine hydrochloride $^1$H NMR (400 MHz, DMSO-d$_6$) δ 11.30 (br. s, 1H), 9.31 (s, 1H), 7.57-7.44 (m, 5H), 7.41-7.37 (m, 5H), 7.04 (dd, J=8.0, 7.6 Hz, 2H), 6.93 (d, J=7.6 Hz, 1H), 3.92-3.88 (m, 2H), 3.60-3.54 (m, 4H), 3.38-3.35 (m, 2H), 3.26-3.22 (m, 4H), 3.08-3.02 (m, 2H), 2.78 (br. s, 3H), 2.22 (s, 3H), 2.18 (s, 3H), 1.95-1.91 (m, 2H), 1.83-1.76 (m, 2H).
MH+ 559 (—HCl).

Example 118

N-(4-(4-(2,3-dimethylphenyl)-2-methylpiperazin-1-yl)butyl)-8,9-diphenyl-9H-purine-6-amine hydrochloride $^1$H NMR (400 MHz, DMSO-d$_6$) δ 11.24 (br. s, 1H), 9.83 (s, 1H), 8.39 (s, 1H), 7.56-7.48 (m, 5H), 7.46-7.42 (m, 5H), 7.06 (dd, J=8.0, 7.6 Hz, 1H), 6.93 (dd, J=7.2, 8.0 Hz, 2H), 3.78-3.74 (m, 2H), 3.54-3.36 (m, 4H), 3.22-3.11 (m, 6H), 3.03-2.97 (m, 1H), 2.22 (s, 3H), 2.17 (s, 3H), 1.93-1.89 (m, 2H), 1.79-1.76 (m, 2H), 1.48-1.41 (m, 3H).
MH+ 545 (—HCl).

Example 119

N-(4-(4-(2,3-dimethylphenyl)-2-methylpiperazin-1-yl)butyl)-2-methyl-8,9-diphenyl-9H-purine-6-amine hydrochloride $^1$H NMR (400 MHz, DMSO-d$_6$) δ 11.27 (br. s, 1H), 7.57-7.47 (m, 5H), 7.45-7.37 (m, 5H), 7.06 (dd, J=7.6, 8.0 Hz, 1H), 6.92 (dd, J=7.2, 8.0 Hz, 2H), 4.20-4.18 (m, 2H), 3.92-3.88 (m, 2H), 3.41-3.34 (m, 2H), 3.20-3.11 (m, 4H), 3.04-3.01 (m, 1H), 2.69 (br. s, 3H), 2.21 (s, 3H), 2.17 (s, 3H), 1.92-1.91 (m, 2H), 1.84-1.81 (m, 2H), 1.47-1.33 (m, 3H).
MH+ 559 (—HCl).

Example 120

4-(4-(2,3-dimethylphenyl)piperazin-1-yl)-1-(methyl (2-methyl-8,9-diphenyl-9H-purin-6-yl)amino)butan-2-ol hydrochloride $^1$H NMR (400 MHz, DMSO-d$_6$) δ 10.09 (br.s, 1H), 8.25 (s, 1H), 7.53-7.48 (m, 6H), 7.40-7.35 (m, 6H), 7.05 (t, J=8.0 Hz, 1H), 6.90 (d, J=8.0 Hz, 1H), 6.86 (d, J=8.0 Hz, 1H), 4.37 (s, 1H), 4.19 (m, 3H), 4.08 (m, 1H), 3.58-3.50 (m, 5H), 3.20-3.15 (m, 3H), 3.04 (s, 3H), 2.19 (s, 3H), 2.13 (s, 3H), 1.92-1.85 (m, 3H), 1.23 (s, 1H).
MH+ 576 (—HCl).

Example 121

4-(4-(2,3-dimethylphenyl)-1,4-diazepan-1-yl)-1-((8,9-diphenyl-9H-purin-6-yl)(methyl)amino)butan-2-ol hydrochloride $^1$H NMR (400 MHz, DMSO-d$_6$) δ 10.25 (br.s, 1H), 8.32 (d, J=8.0 Hz, 2H), 7.57-7.55 (m, 6H), 7.49-7.36 (m, 6H), 7.04 (t, J=8.0 Hz, 1H), 6.95 (d, J=8.0 Hz, 1H), 6.90 (d, J=8.0 Hz, 1H), 4.87 (m, 1H), 4.74 (m, 1H), 4.14 (m, 3H), 3.56 (m, 2H), 3.18 (m, 2H), 3.00 (m, 3H), 2.21 (s, 3H), 2.16 (s, 3H), 2.07 (m, 4H), 1.23 (m, 1H).
MH+ 576 (—HCl).

Example 122

4-((R)-4-(2,3-dimethylphenyl)-2-methylpiperazin-1-yl)-1-((8,9-diphenyl-9H-purin-6-yl)(methyl)amino)butan-2-ol hydrochloride $^1$H NMR (400 MHz, DMSO-d$_6$) δ 10.62 (br.s, 1H), 8.28 (s, 1H), 7.55-7.49 (m, 6H), 7.41-7.36 (m, 6H), 7.07 (t, J=8.0 Hz, 1H), 6.93 (d, J=8.0 Hz, 1H), 6.88 (d, J=8.0 Hz, 1H), 4.54 (s, 1H), 4.11 (m, 3H), 3.71 (m, 1H), 3.46 (m, 2H), 3.23-3.16 (m, 3H), 3.08 (m, 3H), 2.22 (s, 3H), 2.17 (s, 3H), 2.08 (m, 2H), 1.89 (m, 2H).
MH+ 576 (—HCl).

Example 123

4-((S)-4-(2,3-dimethylphenyl)-2-methylpiperazin-1-yl)-1-((8,9-diphenyl-9H-purin-6-yl)(methyl)amino)butan-2-ol hydrochloride $^1$H NMR (400 MHz, DMSO-d$_6$) δ 10.91 (br.s, 1H), 8.31 (s, 1H), 7.54-7.49 (m, 6H), 7.41-7.36 (m, 6H), 7.07 (t, J=8.0 Hz, 1H), 6.91 (d, J=8.0 Hz, 1H), 6.86 (d, J=8.0 Hz, 1H), 4.63 (s, 1H), 4.12 (m, 3H), 3.70 (m, 1H), 3.44 (m, 2H), 3.24-3.17 (m, 3H), 3.14-3.06 (m, 3H), 2.19 (s, 3H), 2.14 (s, 3H), 2.06 (m, 2H), 1.89 (m, 2H).
MH+ 576 (—HCl).

Example 124

4-(4-(2,3-dimethylphenyl)-2-methylpiperazin-1-yl)-1-((8,9-diphenyl-9H-purin-6-yl)(methyl)amino)butan-2-ol hydrochloride $^1$H NMR (400 MHz, DMSO-d$_6$) δ 10.61 (br.s, 1H), 8.27 (s, 1H), 7.55-7.48 (m, 6H), 7.41-7.36 (m, 6H), 7.06 (t, J=8.0 Hz, 1H), 6.92 (d, J=8.0 Hz, 1H), 6.87 (d, J=8.0 Hz, 1H), 4.61 (s, 1H), 4.07 (m, 3H), 3.70 (m, 1H), 3.52 (m, 2H), 3.20-3.16 (m, 3H), 3.07 (m, 3H), 2.21 (s, 3H), 2.16 (s, 3H), 2.08 (m, 2H), 1.89 (m, 2H).
MH+ 576 (—HCl).

Example 125

4-(4-(2,3-dimethylphenyl)piperazin-1-yl)-1-(8,9-diphenyl-9H-purin-6-ylamino)butan-2-ol hydrochloride $^1$H NMR (400 MHz, DMSO-d$_6$) δ 8.33 (s, 1H), 8.24 (s, 1H), 7.54-7.46 (m, 2H), 7.42-7.36 (m, 2H), 7.07 (t, J=8.0 Hz, 1H), 6.94-6.89 (m, 2H), 4.03-3.93 (m, 5H), 3.66 (m, 3H), 3.54 (m, 3H), 3.26-3.16 (m, 4H), 3.08 (m, 4H), 2.21 (s, 3H), 2.16 (s, 3H), 2.06 (m, 2H), 1.88 (m, 2H).
MH+ 548 (—HCl).

Example 126

1-(4-(2,3-dimethylphenyl)piperazin-1-yl)-4-(8,9-diphenyl-9H-purin-6-ylamino)butan-2-ol hydrochloride $^1$H NMR (400 MHz, DMSO-d$_6$) δ 8.28 (s, 1H), 7.53-7.47 (m, 6H), 7.37-7.36 (m, 6H), 7.06 (t, J=8.0 Hz, 1H), 6.98 (d, J=8.0 Hz, 1H), 6.90 (d, J=8.0 Hz, 1H), 4.26 (t, J=4.0 Hz, 1H), 4.09 (s, 1H) 3.80 (m, 2H), 3.66 (m, 2H), 3.41 (m, 1H), 3.31 (m, 3H), 2.66 (m, 1H), 2.21 (s, 3H), 2.16 (s, 3H), 1.79 (m, 2H), 1.18 (t, J=4.0 Hz, 2H).
MH+ 548 (—HCl).

Example 127

N-(4-(4-(2,3-dimethylphenyl)-2-methylpiperazin-1-yl)butyl)-N-methyl-8,9-diphenyl-9H-purine-6-amine hydrochloride $^1$H NMR (400 MHz, DMSO-d$_6$) δ 11.50 (br. s, 1H), 8.38 (s, 1H), 7.62-7.52 (m, 5H), 7.46-7.38 (m, 5H), 7.06 (dd, J=7.6, 8.0 Hz, 1H), 6.92 (d, J=7.6 Hz, 1H), 6.88 (d, J=7.6 Hz, 1H), 4.59-4.45 (m, 2H), 3.98-3.92 (m, 2H), 3.57-3.52 (m, 2H), 3.45-3.34 (m, 2H), 3.21-3.11 (m, 6H), 3.03-2.98 (m, 1H), 2.21 (s, 3H), 2.16 (s, 3H), 1.92 (br. s, 3H), 1.33-1.23 (m, 3H).
MH+ 559 (—HCl).

Example 128

N-(4-(4-(2,3-dimethylphenyl)-2-methylpiperazin-1-yl)butyl)-N,2-dimethyl-8,9-diphenyl-9H-purine-6-amine hydrochloride $^1$H NMR (400 MHz, DMSO-d$_6$) δ 11.49 (br. s, 1H), 7.55-7.45 (m, 5H), 7.43-7.35 (m, 5H), 7.03 (dd, J=7.6, 7.6 Hz, 1H), 6.90 (d, J=7.6 Hz, 1H), 6.85 (d, J=7.6 Hz, 1H), 4.46-4.41 (m, 2H), 3.56-3.50 (m, 2H), 3.38-3.34 (m, 2H), 3.18-3.11 (m, 8H), 3.02-2.98 (m, 1H), 2.60 (br. s, 3H), 2.19 (s, 3H), 2.13 (s, 3H), 1.88 (br. s, 3H), 1.32-1.28 (m, 3H).
MH+ 573 (—HCl).

Example 129

N-(4-(4-(2,3-dimethylphenyl)-1,4-diazepan-1-yl)butyl)-N-methyl-8,9-diphenyl-9H-purine-6-amine hydrochloride $^1$H NMR (400 MHz, DMSO-d$_6$) δ 11.40 (br. s, 1H), 8.36 (s, 1H), 7.58-7.51 (m, 5H), 7.46-7.37 (m, 5H), 7.07-6.92 (m, 3H), 4.48-4.44 (m, 2H), 3.48-3.42 (m, 4H), 3.32-3.22 (m, 6H), 3.12-3.04 (m, 4H), 2.21 (s, 3H), 2.18 (s, 3H), 2.08-2.04 (m, 2H), 1.91-1.87 (m, 3H).
MH+ 559 (—HCl).

Example 130

N-(4-(4-(2,3-dimethylphenyl)-1,4-diazepan-1-yl)butyl)-N,2-dimethyl-8,9-diphenyl-9H-purine-6-amine hydrochloride $^1$H NMR (400 MHz, DMSO-d$_6$) δ 11.45 (br. s, 1H), 7.59-7.57 (m, 3H), 7.49-7.41 (m, 4H), 7.39-7.35 (m, 3H), 7.07-6.92 (m, 3H), 3.57-3.41 (m, 6H), 3.32-3.16 (m, 6H), 2.61 (s, 3H), 2.21 (s, 3H), 2.18 (s, 3H), 2.06-2.03 (m, 2H), 1.90-1.86 (m, 3H).
MH+ 573 (—HCl).

Example 131

N-(4-(4-(2,3-dimethylphenyl)-2-methylpiperazin-1-yl)butyl)-N-ethyl-8,9-diphenyl-9H-purine-6-amine hydrochloride $^1$H NMR (400 MHz, DMSO-d$_6$) δ 11.40 (br. s, 1H), 8.35 (s, 1H), 7.58-7.50 (m, 5H), 7.45-7.39 (m, 5H), 7.07 (dd, J=7.6, 7.6 Hz, 1H), 6.93 (d, J=7.6 Hz, 1H), 6.88 (d, J=7.6 Hz, 1H), 4.46-4.40 (m, 2H), 4.04-4.01 (m, 2H), 3.57-3.55 (m, 2H), 3.45-3.32 (m, 2H), 3.22-3.10 (m, 4H), 3.06-2.97 (m, 1H), 2.22 (s, 3H), 2.17 (s, 3H), 2.06-1.92 (m, 4H), 1.39-1.31 (m, 3H), 1.23-1.17 (m, 3H).
MH+ 573 (—HCl).

Example 132

N-(4-(4-(2,3-dimethylphenyl)-2-methylpiperazin-1-yl)butyl)-N-ethyl-2-methyl-8,9-diphenyl-9H-purine-6-amine hydrochloride $^1$H NMR (400 MHz, DMSO-d$_6$) δ 11.40 (br. s, 1H), 7.59-7.55 (m, 3H), 7.48-7.35 (m, 7H), 7.07 (dd, J=7.6, 7.6 Hz, 1H), 6.93 (d, J=7.2 Hz, 1H), 6.88 (d, J=7.2 Hz, 1H), 4.40-4.36 (m, 2H), 4.06-4.01 (m, 2H), 3.57-3.53 (m, 1H), 3.39-3.37 (m, 2H), 3.20-2.98 (m, 6H), 2.59 (s, 3H), 2.22 (s, 3H), 2.17 (s, 3H), 1.96-1.88 (m, 4H), 1.39-1.32 (m, 3H), 1.23-1.17 (m, 3H).
MH+ 587 (—HCl).

Example 133

N-(4-(4-(2,3-dimethylphenyl)-1,4-diazepan-1-yl)butyl)-N-ethyl-8,9-diphenyl-9H-purine-6-amine hydrochloride $^1$H NMR (400 MHz, DMSO-d$_6$) δ 11.47 (br. s, 1H), 8.37 (s, 1H), 7.58-7.50 (m, 5H), 7.47-7.37 (m, 5H), 7.09-6.94 (m, 3H), 4.46-4.42 (m, 2H), 4.04-4.00 (m, 2H), 3.51-3.43 (m, 6H), 3.24-3.06 (m, 6H), 2.22 (s, 3H), 2.20 (s, 3H), 1.96-1.88 (m, 5H), 1.36-1.30 (m, 3H).
MH+ 573 (—HCl).

Example 134

N-(4-(4-(2,3-dimethylphenyl)-1,4-diazepan-1-yl)butyl)-N-ethyl-2-methyl-8,9-diphenyl-9H-purine-6-amine hydrochloride $^1$H NMR (400 MHz, DMSO-d$_6$) δ 11.50 (br. s, 1H), 7.60-7.55 (m, 3H), 7.47-7.44 (m, 2H), 7.41-7.35 (m, 5H), 7.09-6.93 (m, 3H), 4.42-4.38 (m, 2H), 4.05-4.00 (m, 2H), 3.57-3.53 (m, 4H), 3.36-3.16 (m, 6H), 3.10-3.06 (m, 2H), 2.67 (s, 3H), 2.22 (s, 3H), 2.20 (s, 3H), 1.96-1.86 (m, 4H), 1.33-1.23 (m, 3H).
MH+ 587 (—HCl).

Example 135

(S)—N-(4-(4-(2,3-dimethylphenyl)-2-methylpiperazin-1-yl)butyl)-8,9-diphenyl-9H-purine-6-amine hydrochloride $^1$H NMR (400 MHz, DMSO-d$_6$) δ 11.24 (br. s, 1H), 9.83 (s, 1H), 8.39 (s, 1H), 7.56-7.48 (m, 5H), 7.46-7.42 (m, 5H), 7.06

(dd, J=8.0, 7.6 Hz, 1H), 6.93 (dd, J=7.2, 8.0 Hz, 2H), 3.78-3.74 (m, 2H), 3.54-3.36 (m, 4H), 3.22-3.11 (m, 6H), 3.03-2.97 (m, 1H), 2.22 (s, 3H), 2.17 (s, 3H), 1.93-1.89 (m, 2H), 1.79-1.76 (m, 2H), 1.48-1.41 (m, 3H).
MH+ 545 (—HCl).

Example 136

(S)—N-(4-(4-(2,3-dimethylphenyl)-2-methylpiperazin-1-yl)butyl)-2-methyl-8,9-diphenyl-9H-purine-6-amine hydrochloride $^1$H NMR (400 MHz, DMSO-$d_6$) δ 11.27 (br. s, 1H), 7.57-7.47 (m, 5H), 7.45-7.37 (m, 5H), 7.06 (dd, J=7.6, 8.0 Hz, 1H), 6.92 (dd, J=7.2, 8.0 Hz, 2H), 4.20-4.18 (m, 2H), 3.92-3.88 (m, 2H), 3.41-3.34 (m, 2H), 3.20-3.11 (m, 4H), 3.04-3.01 (m, 1H), 2.69 (br. s, 3H), 2.21 (s, 3H), 2.17 (s, 3H), 1.92-1.91 (m, 2H), 1.84-1.81 (m, 2H), 1.47-1.33 (m, 3H).
MH+ 559 (—HCl)

Example 137

(R)—N-(4-(4-(2,3-dimethylphenyl)-2-methylpiperazin-1-yl)butyl)-8,9-diphenyl-9H-purine-6-amine hydrochloride $^1$H NMR (400 MHz, DMSO-$d_6$) δ 11.24 (br. s, 1H), 9.83 (s, 1H), 8.39 (s, 1H), 7.56-7.48 (m, 5H), 7.46-7.42 (m, 5H), 7.06 (dd, J=8.0, 7.6 Hz, 1H), 6.93 (dd, J=7.2, 8.0 Hz, 2H), 3.78-3.74 (m, 2H), 3.54-3.36 (m, 4H), 3.22-3.11 (m, 6H), 3.03-2.97 (m, 1H), 2.22 (s, 3H), 2.17 (s, 3H), 1.93-1.89 (m, 2H), 1.79-1.76 (m, 2H), 1.48-1.41 (m, 3H).
MH+ 545 (—HCl)

Example 138

(R)—N-(4-(4-(2,3-dimethylphenyl)-2-methylpiperazin-1-yl)butyl)-2-methyl-8,9-diphenyl-9H-purine-6-amine hydrochloride $^1$H NMR (400 MHz, DMSO-$d_6$) δ 11.27 (br. s, 1H), 7.57-7.47 (m, 5H), 7.45-7.37 (m, 5H), 7.06 (dd, J=7.6, 8.0 Hz, 1H), 6.92 (dd, J=7.2, 8.0 Hz, 2H), 4.20-4.18 (m, 2H), 3.92-3.88 (m, 2H), 3.41-3.34 (m, 2H), 3.20-3.11 (m, 4H), 3.04-3.01 (m, 1H), 2.69 (br. s, 3H), 2.21 (s, 3H), 2.17 (s, 3H), 1.92-1.91 (m, 2H), 1.84-1.81 (m, 2H), 1.47-1.33 (m, 3H).
MH+ 559 (—HCl)

Example 139

(S)—N-(4-(4-(2,3-dimethylphenyl)-2-methylpiperazin-1-yl)butyl)-N-methyl-8,9-diphenyl-9H-purine-6-amine hydrochloride $^1$H NMR (400 MHz, DMSO-$d_6$) δ 11.50 (br. s, 1H), 8.38 (s, 1H), 7.62-7.52 (m, 5H), 7.46-7.38 (m, 5H), 7.06 (dd, J=7.6, 8.0 Hz, 1H), 6.92 (d, J=7.6 Hz, 1H), 6.88 (d, J=7.6 Hz, 1H), 4.59-4.45 (m, 2H), 3.98-3.92 (m, 2H), 3.57-3.52 (m, 2H), 3.45-3.34 (m, 2H), 3.21-3.11 (m, 6H), 3.03-2.98 (m, 1H), 2.21 (s, 3H), 2.16 (s, 3H), 1.92 (br. s, 3H), 1.33-1.23 (m, 3H).
MH+ 559 (—HCl).

Example 140

(S)—N-(4-(4-(2,3-dimethylphenyl)-2-methylpiperazin-1-yl)butyl)-N,2-dimethyl-8,9-diphenyl-9H-purine-6-amine hydrochloride $^1$H NMR (400 MHz, DMSO-$d_6$) δ 11.49 (br. s, 1H), 7.55-7.45 (m, 5H), 7.43-7.35 (m, 5H), 7.03 (dd, J=7.6, 7.6 Hz, 1H), 6.90 (d, J=7.6 Hz, 1H), 6.85 (d, J=7.6 Hz, 1H), 4.46-4.41 (m, 2H), 3.56-3.50 (m, 2H), 3.38-3.34 (m, 2H), 3.18-3.11 (m, 8H), 3.02-2.98 (m, 1H), 2.60 (br. s, 3H), 2.19 (s, 3H), 2.13 (s, 3H), 1.88 (br. s, 3H), 1.32-1.28 (m, 3H).
MH+ 573 (—HCl).

Example 141

(R)—N-(4-(4-(2,3-dimethylphenyl)-2-methylpiperazin-1-yl)butyl)-N-methyl-8,9-diphenyl-9H-purine-6-amine hydrochloride $^1$H NMR (400 MHz, DMSO-$d_6$) δ 11.50 (br. s, 1H), 8.38 (s, 1H), 7.62-7.52 (m, 5H), 7.46-7.38 (m, 5H), 7.06 (dd, J=7.6, 8.0 Hz, 1H), 6.92 (d, J=7.6 Hz, 1H), 6.88 (d, J=7.6 Hz, 1H), 4.59-4.45 (m, 2H), 3.98-3.92 (m, 2H), 3.57-3.52 (m, 2H), 3.45-3.34 (m, 2H), 3.21-3.11 (m, 6H), 3.03-2.98 (m, 1H), 2.21 (s, 3H), 2.16 (s, 3H), 1.92 (br. s, 3H), 1.33-1.23 (m, 3H).
MH+ 559 (—HCl).

Example 142

(R)—N-(4-(4-(2,3-dimethylphenyl)-2-methylpiperazin-1-yl)butyl)-N,2-dimethyl-8,9-diphenyl-9H-purine-6-amine hydrochloride $^1$H NMR (400 MHz, DMSO-$d_6$) δ 11.49 (br. s, 1H), 7.55-7.45 (m, 5H), 7.43-7.35 (m, 5H), 7.03 (dd, J=7.6, 7.6 Hz, 1H), 6.90 (d, J=7.6 Hz, 1H), 6.85 (d, J=7.6 Hz, 1H), 4.46-4.41 (m, 2H), 3.56-3.50 (m, 2H), 3.38-3.34 (m, 2H), 3.18-3.11 (m, 8H), 3.02-2.98 (m, 1H), 2.60 (br. s, 3H), 2.19 (s, 3H), 2.13 (s, 3H), 1.88 (br. s, 3H), 1.32-1.28 (m, 3H).
MH+ 573 (—HCl).

Example 143

N-(4-(4-(2,3-dimethylphenyl)piperazin-1-yl)butyl)-2-methyl-8,9-diphenyl-9H-purine-6-amine hydrochloride $^1$H NMR (400 MHz, DMSO-$d_6$) δ 11.46 (br. s, 1H), 9.34 (s, 1H), 7.58-7.50 (m, 3H), 7.47-7.38 (m, 7H), 7.07 (dd, J=7.6, 7.6 Hz, 1H), 6.92 (d, J=7.6 Hz, 1H), 6.88 (d, J=6.8 Hz, 1H), 4.24-4.20 (m, 2H), 3.94-3.92 (m, 1H), 3.54-3.53 (m, 1H), 3.22-3.15 (m, 4H), 3.11-3.03 (m, 4H), 2.72 (br. s, 3H), 2.21 (s, 3H), 2.15 (s, 3H), 1.97-1.94 (m, 2H), 1.85-1.78 (m, 2H).
MH+ 545 (—HCl).

Experimental Example 1

Measurement of Binding Affinity for Serotonin 5-HT$_{2A}$ and 5-HT$_{2C}$ Receptors Receptor binding affinities of the compounds for serotonin receptors were measured by the method described in the literature (see [Park W K et al., *Pharmacol Biochem Behav.*, 82(2), 361-372 (2005)].

For serotonin 5-HT$_{2A}$ binding, an aliquot of human recombinant serotonin 5-HT$_{2A}$ receptor (PerkinElmer Life and Analytical Sciences, USA) expressed in CHO-K1 cells (5 μg/well) and 1 nM [$^3$H]Ketanserin (PerkinElmer) were used in the presence of mianserin (20 μM) as a nonspecific. The reaction mixture was incubated for 60 min at using 50 mM Tris-HCl (pH 7.4) buffer containing 4 mM CaCl$_2$ and 0.1% ascorbic acid, and harvested through filtermate A glass fiber filter (Wallac, Finland) presoaked in 0.5% polyethyleneimine (PEI) by microbeta filtermate-96 harvester (PerkinElmer) to terminate the reaction, and then washed with ice cold 50 mM Tris-HCl buffer solution (pH 7.4). The filter was then covered with MeltiLex, sealed in a sample bag, dried in an oven. The radioactivity retained in the filter was finally counted using MicroBeta Plus (Wallac).

The binding affinity ($IC_{50}$) of a compound for the receptor was calculated by computerized nonlinear regression analysis (GraphPad Prism Program, San Diego, USA) using 7-8 varied concentrations of the compound run in duplicate tubes.

For serotonin 5-$HT_{2C}$ binding, frozen membranes from stable CHO-K1 cell line expressing the human recombinant 5-$HT_{2C}$ receptor (PerkinElmer, 4 μg/well), [$^3$H]Mesulergine (Amersham, 1.3 nM) and test compounds were added into 50 mM Tris-HCl (pH 7.4) buffer containing 0.1% ascorbic acid and 4 mM $CaCl_2$. Nonspecific binding was determined using 100 μM mianserin. The incubations were performed for 60 min at 27, and these were terminated by rapid filtration through filtermate A glass fiber filter presoaked in 0.5% PEI. The measurement results of binding affinity to serotonin receptor 5-$HT_{2A}$ and 5-$HT_{2C}$ are shown in the following Table 1 (unit: nM).

TABLE 1

| Compound | 5-$HT_{2A}$ | 5-$HT_{2C}$ |
|---|---|---|
| Example 1 | 14 | 86 |
| Example 2 | 32 | 163 |
| Example 10 | 11 | 106 |
| Example 12 | 13 | 147 |
| Example 13 | 56 | 294 |
| Example 18 | 28 | 216 |
| Example 23 | 36 | 76 |
| Example 28 | 65 | 430 |
| Example 34 | 54 | 230 |
| Example 35 | 106 | 789 |
| Example 36 | 29 | 285 |
| Example 38 | 404 | 1587 |
| Example 39 | 33 | 328 |
| Example 40 | 125 | 713 |
| Example 41 | 16 | 224 |
| Example 42 | 40 | 560 |
| Example 43 | 14 | 118 |
| Example 44 | 54 | 510 |
| Example 45 | 14 | 151 |
| Example 49 | 47 | 364 |
| Example 51 | 66 | 423 |
| Example 55 | 31.1 | 129 |
| Example 56 | 7.5 | 76.5 |
| Example 67 | 42 | 247 |
| Example 68 | 2.4 | 4.7 |
| Example 70 | 54.3 | 316 |
| Example 76 | 43.1 | 453 |
| Example 79 | 43 | 303 |
| Example 83 | 30 | 198 |
| Example 85 | 9.6 | 70 |
| Example 86 | 25 | 376 |
| Example 87 | 9.3 | 100 |
| Example 91 | 28 | 141 |
| Example 92 | 17 | 301 |
| Nefazodone[a] | 710 | 160 |

[a]Nefazodone; Owens, M. J., et al. *J. Pharm. & Exp. Thera.*, 1997 (283) 1305.

Experimental Example 2

Measurement of Binding Affinity for Serotonin Transporter

For serotonin transporter binding assays, a reaction mixture with a final volume of 0.25 ml was prepared by mixing a test compound, human serotonin transporter membrane expressed in HEK-293 cells (PerkinElmer, 5 μg/well), [$^3$H] Imipramine (PerkinElmer, 2 nM) and 50 mM Tris-HCl (pH 7.4) buffer containing 120 mM NaCl and 5 mM KCl. The reaction mixture was incubated for 30 min at 27, and harvested through filtermate A glass fiber filter presoaked in 0.5% PEI with ice cold 50 mM Tris-HCl buffer (pH 7.4) containing 0.9% NaCl. The measurement results of binding affinity to serotonin transporter (SERT) are shown in the following Table 2 (unit: nM).

TABLE 2

| Compound | Serotonin Transporter |
|---|---|
| Example 1 | 64 |
| Example 2 | 75 |
| Example 10 | 161 |
| Example 12 | 93 |
| Example 13 | 35 |
| Example 18 | 575 |
| Example 23 | 106 |
| Example 28 | 85 |
| Example 34 | 6 |
| Example 35 | 27 |
| Example 36 | 4 |
| Example 38 | 19 |
| Example 39 | 21 |
| Example 40 | 18 |
| Example 41 | 7 |
| Example 42 | 8 |
| Example 43 | 16 |
| Example 44 | 65 |
| Example 45 | 49 |
| Example 49 | 62 |
| Example 51 | 19 |
| Example 55 | 518 |
| Example 56 | 146 |
| Example 67 | 96 |
| Example 68 | 146 |
| Example 70 | 43.8 |
| Example 76 | 128 |
| Example 79 | 67 |
| Example 83 | 42 |
| Example 85 | 362 |
| Example 86 | 64 |
| Example 87 | 136 |
| Example 91 | 316 |
| Example 92 | 38.9 |
| Nefazodone[a] | 4 |

[a]Nefazodone; Owens, M. J., et al. *J. Pharm. & Exp. Thera.*, 1997 (283) 1305.

Experimental Example 3

Measurement of Anti-Depressants Activity in Forced Swimming Test

To evaluate the anti-depressants activity of the compounds, the inhibitory effects on immobility in forced swimming test in mice were measured according to the methods described in the literature (see [Porsolt R D, et al., *Eur J Pharmacol.*, 51, 291-294 (1978)]).

Each mouse was placed in a 25 cm glass cylinder (10 cm diameter) containing 15 cm of water maintained at 22±1, and was forced to swim for 10 min. 24 hours later, the mouse was replaced into the cylinder and the total duration of immobility was recorded during the last 5 min of the 6-min testing period. Mice are judged immobile when they float in an upright position and make only small movements to keep their head above water. Test drugs were suspended in 3% Tween 80 solution, and administered orally (po) 60 min before the testing. The measurement results of antidepressants activity Immobility in forced swimming test on mice are shown in the following Table 3 (unit: %).

TABLE 3

| Compound | 100 mg/kg | 50 mg/kg | 25 mg/kg |
| --- | --- | --- | --- |
| Example 1 | — | 41.79 | — |
| Example 2 | — | 47.13 ± 10.41 | 58.34 ± 11.05 |
| Example 10 | — | 80.58 ± 11.21 | 74.56 ± 14.08 |
| Example 12 | — | — | 94.69 ± 12.46 |
| Example 13 | — | — | 89.81 ± 7.14 |
| Example 18 | — | — | 89.98 ± 11.45 |
| Example 23 | — | — | 99.59 ± 6.34 |
| Example 28 | — | — | 87.65 ± 7.08 |
| Example 34 | — | 96.83 ± 11.02 | 76.92 ± 10.04 |
| Example 35 | — | — | 87.36 ± 6.89 |
| Example 36 | — | 86.77 ± 11.28 | 79.93 ± 13.23 |
| Example 38 | — | 64.14 ± 10.74 | 74.86 ± 9.75 |
| Example 39 | — | — | 88.94 ± 5.41 |
| Example 40 | — | — | 98.20 ± 10.00 |
| Example 41 | — | — | 105.95 ± 4.92 |
| Example 42 | — | — | 86.65 ± 6.40 |
| Example 43 | — | — | 81.26 ± 11.85 |
| Example 44 | — | — | 80.41 ± 7.04 |
| Example 45 | — | — | 97.64 ± 7.25 |
| Example 49 | — | — | 81.07 ± 7.11 |
| Example 51 | — | — | 99.44 ± 10.28 |
| Example 55 | — | 78.41 ± 8.11 | 70.53 ± 11.73 |
| Example 56 | — | 77.46 ± 12.27 | 71.41 ± 10.84 |
| Example 67 | — | — | — |
| Example 68 | — | 72.11 ± 7.63 | 78.66 ± 11.33 |
| Example 70 | — | 53.34 ± 10.82 | 80.67 ± 12.19 |
| Example 76 | — | 90.13 ± 4.29 | 79.98 ± 7.42 |
| Example 79 | — | — | — |
| Example 83 | — | — | 70.43 ± 6.15 |
| Example 85 | — | — | — |
| Example 86 | — | — | 66.53 ± 8.35 |
| Example 87 | — | — | 88.26 ± 6.05 |
| Example 91 | — | — | 89.19 ± 9.17 |
| Example 92 | — | — | 85.86 ± 8.90 |
| Fluoxetine[a] | 59.5[b] | 70.4[b] | — |

[a]Antidepressants activity Immobility in forced swimming test on mice of fluoxetine was measured via in-house assay.
[b]These data were obtained in multiple measurements.

Experimental Example 4

Measurement of Synergy Effect Depending on Using a Combination of the Inventive Compound and the Conventional Anti-Depressants To evaluate the interaction or augmentation between the inventive compound (Example 68) and anti-depressants with different mechanisms of action, we measured an immobility in forced swimming test on mice according to the method described in the literature (see [Porsolt R D, et al., *Eur J. Pharmacol.*, 51, 291-294 (1978)]. Several antidepressants were chosen including Prozac, the selective serotonin reuptake inhibitor (SSRI) and Effexor, serotonin-norepinephrine reuptake inhibitors (SNRI). We examined the effect of those drugs under the suboptimal dose of 25 mg/kg in combination with the inventive compound (Example 68) at the doses of 12.5 mg/kg or 25 mg/kg (These doses do not demonstrate efficacy on animal model when the inventive compound of Example 68 alone is administered). Each drug or vehicle was suspended in 3% Tween 80 solution and administered orally (p.o.) 60 min before forced swimming test. The measurement results of synergy effect depending on combination of the inventive compound and the conventional antidepressants in forced swimming test on mice are shown in FIGS. 1 and 2 respectively (unit: %).

Figure 2:
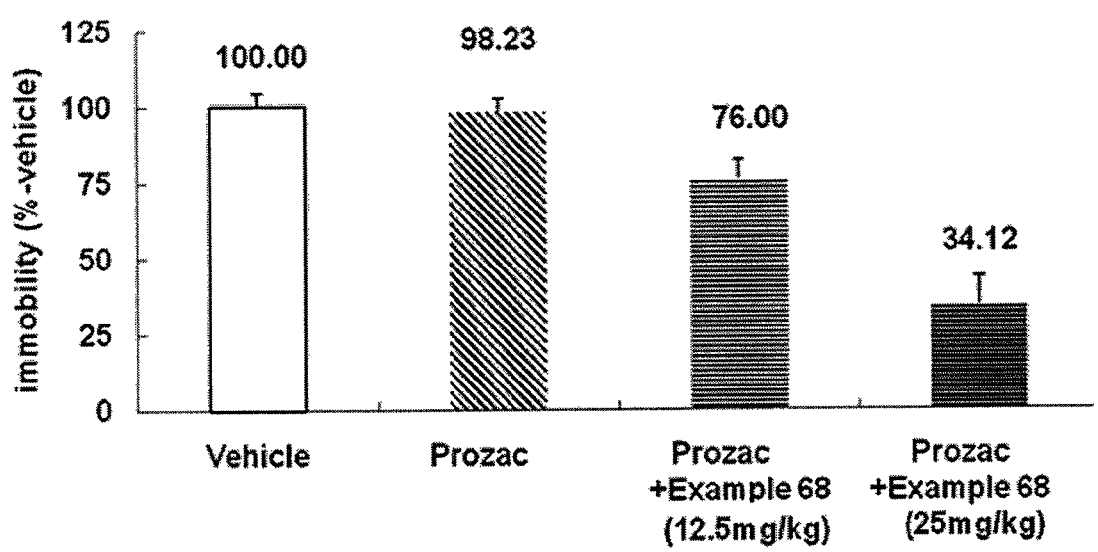
FIG. 2: a graph showing the measurement result for synergy effect depending on combination of the inventive compound (Example 68, 12.5 mg/kg or 25 mg/kg) and Prozac (25 mg/kg).

As can be seen from FIGS. 1 and 2, Prozac or Effexor (25 mg/kg) alone did not improve the anti-immobility effect in FST, while combination group (Example 68 plus Effexor or Example 68 plus Prozac) caused a marked improvement than monotherapy. These results suggest that the combination blockade of both 5-HT$_{2A/2C}$ receptor and transporters may result in greater efficacy than blocking 5-HT$_{2A/2C}$ or the serotonin transporter alone.

While the invention has been described with respect to the above specific embodiments, it should be recognized that various modifications and changes may be made to the invention by those skilled in the art which also fall within the scope of the invention as defined by the appended claims.

What is claimed is:
1. A compound of formula (I), or a pharmaceutically acceptable salt thereof.

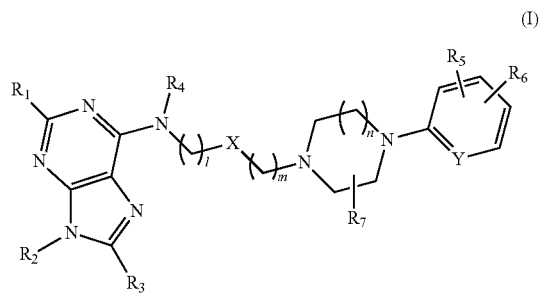

wherein,
$R_1$ represents hydrogen or —CH$_3$;
$R_2$ represents carbocycle, substituted carbocycle, aryl, substituted aryl, acyloxy, C$_{1-6}$ alkoxy, substituted C$_{1-6}$ alkoxy, C$_{3-5}$ alkenyloxy, substituted C$_{3-5}$ alkenyloxy, C$_{3-5}$ alkynyloxy, substituted C$_{3-5}$ alkynyloxy, aryloxy, substituted aryloxy, heteroaryloxy, heteroaryloxy substituted with alkoxy or halogen, heteroaryl, substituted heteroaryl, heterocycloalkyl, substituted heterocycloalkyl, C$_{2-6}$ alkenyl, C$_{2-6}$ alkenyl substituted with alkoxy or halogen, C$_{2-6}$ alkynyl, C$_{2-6}$ alkynyl substituted with alkoxy or halogen, —(CH$_2$)$_p$—C$_{3-6}$ carbocycle, —(CH$_2$)$_p$—C$_{3-6}$ carbocycle substituted with alkoxy or halogen, or —(CH$_2$)$_q$—R', and R' being phenyl, furanyl, benzofuranyl, thienyl, benzothienyl, pyridinyl, pyridiminyl, pyrazinyl, pyridizinyl, tetrahydrofuranyl, tetrahydropyranyl, dioxanyl, 1,4-benzodioxanyl, or benzo[1,3]dioxolyl, each of which being optionally substituted with one or more substituents selected from the group consisting of halogen, C$_{1-3}$ alkyl, C$_{1-3}$ alkyl having one to three fluorine substituents, C$_{1-3}$ alkoxy and C$_{1-3}$ alkoxy having one to three fluorine substituents, C$_{1-3}$ alkoxy or C$_{1-3}$ alkoxy having one to three fluorine substituents, and p and q being independently 1 or 2;
$R_3$ represents hydrogen, C$_{1-4}$ alkyl, substituted C$_{1-4}$ alkyl, C$_{3-7}$ carbocycle, substituted C$_{3-7}$ carbocycle, aryl, substituted aryl, heteroaryl, substituted heteroaryl, heterocycloalkyl, or substituted heterocycloalkyl;
$R_4$ represents hydrogen or C$_{1-3}$ alkyl;
$R_5$ and $R_6$ are each independently halogen, C$_{1-3}$ alkyl, C$_{1-3}$ alkoxy, cyano, monofluoromethyl, difluoromethyl, or trifluoromethyl, or $R_5$ and $R_6$, together with the aryl ring to which they are bonded, form a 5- to 7-membered saturated or unsaturated heterocyclic ring, aryl ring, or aryl ring substituted with one or more C$_{1-3}$ alkyl, C$_{1-3}$ alkoxy, halogen, trifluoromethyl, or cyano;
$R_7$ represents hydrogen or C$_{1-3}$ alkyl;
when l=1, m=0 or l=0, m=1, X is —CH$_2$—;
when l=1 or 2, m=1 or 2 and both of l and m are not 2, X is —CH$_2$— or —CHOH—;

Y is —N= or

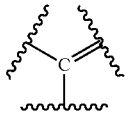

with the proviso that when Y is —N=, $R_5$ or $R_6$ cannot be connected to Y; and n is 1 or 2.

2. The compound according to claim 1, wherein
$R_1$ represents hydrogen or —CH$_3$;
$R_2$ represents $C_{3-7}$ carbocycle, allyl, propargyl, heterocycloalkyl, aryl, aryl substituted with halogen or $C_{1-3}$ alkyl, heteroaryl, or heteroaryl substituted with halogen or $C_{1-3}$ alkyl;
$R_3$ represents hydrogen, $C_{3-7}$ carbocycle, allyl, propargyl, heterocycloalkyl, aryl, aryl substituted with halogen or $C_{1-3}$ alkyl, heteroaryl, or heteroaryl substituted with halogen or $C_{1-3}$ alkyl;
$R_4$ represents hydrogen or $C_{1-3}$ alkyl;
$R_5$ and $R_6$, are independently halogen, $C_{1-3}$ alkyl or $C_{1-2}$ alkoxy;
$R_7$ represents $C_{1-3}$ alkyl;
when l=1, m=0 or l=0, m=1, X is —CH$_2$—;
when l=1 or 2, m=1 or 2 and both of l and m are not 2, X is —CH$_2$— or —CHOH—;
Y is

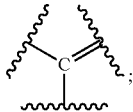 [SMILES: *C(*)=*]

and
n is 1 or 2.

3. The compound according to claim 1, which is selected from the group consisting of:
N-(3-(4-(2,3-dichlorophenyl)piperazin-1-yl)propyl)-8,9-diphenyl-9H-purine-6-amine;
N-(3-(4-(2,3-dichlorophenyl)piperazin-1-yl)propyl)-9-phenyl-8-propyl-9H-purine-6-amine;
N-(3-(4-(2,3-dichlorophenyl)piperazin-1-yl)propyl)-8-methyl-9-phenyl-9H-purine-6-amine;
N-(3-(4-(2,3-dimethylphenyl)piperazin-1-yl)propyl)-8-methyl-9-phenyl-9H-purine-6-amine;
N-(3-(4-(2,3-dichlorophenyl)piperazin-1-yl)propyl)-8-ethyl-9-phenyl-9H-purine-6-amine;
N-(3-(4-(2,3-dimethylphenyl)piperazin-1-yl)propyl)-8-ethyl-9-phenyl-9H-purine-6-amine;
N-(2-(4-(2,3-dichlorophenyl)piperazin-1-yl)ethyl)-8-methyl-9-phenyl-9H-purine-6-amine;
N-(2-(4-(2,3-dichlorophenyl)piperazin-1-yl)ethyl)-8-ethyl-9-phenyl-9H-purine-6-amine;
N-(2-(4-(2,3-dimethylphenyl)piperazin-1-yl)ethyl)-8-ethyl-9-phenyl-9H-purine-6-amine;
N-(2-(4-(2,3-dichlorophenyl)piperazin-1-yl)ethyl)-9-phenyl-8-propyl-9H-purine-6-amine;
N-(2-(4-(2,3-dimethylphenyl)piperazin-1-yl)ethyl)-9-phenyl-8-propyl-9H-purine-6-amine;
N-(3-(4-(2,3-dimethylphenyl)piperazin-1-yl)propyl)-9-phenyl-9H-purine-6-amine;
N-(2-(4-(2,3-dimethylphenyl)piperazin-1-yl)ethyl)-9-phenyl-9H-purine-6-amine;
N-(3-(4-(2,3-dichlorophenyl)piperazin-1-yl)propyl)-9-phenyl-9H-purine-6-amine;
1-(4-(2,3-dichlorophenyl)piperazin-1-yl)-3-(9-phenyl-9H-purin-6-ylamino)propan-2-ol;
N-(2-(4-(2,3-dichlorophenyl)piperazin-1-yl)ethyl)-8,9-diphenyl-9H-purine-6-amine;
N-(2-(4-(2,3-dimethylphenyl)piperazin-1-yl)ethyl)-8,9-diphenyl-9H-purine-6-amine;
N-(3-(4-(2,3-dimethylphenyl)piperazin-1-yl)propyl)-8,9-diphenyl-9H-purine-6-amine;
1-(4-(2,3-dichlorophenyl)piperazin-1-yl)-3-(8,9-diphenyl-9H-purin-6-ylamino)propan-2-ol;
1-(4-(2,3-dichlorophenyl)piperazin-1-yl)-3-(8-methyl-9-phenyl-9H-purin-6-ylamino)propan-2-ol;
1-(4-(2,3-dichlorophenyl)piperazin-1-yl)-3-(8-ethyl-9-phenyl-9H-purin-6-ylamino)propan-2-ol;
1-(4-(2,3-dichlorophenyl)piperazin-1-yl)-3-(9-phenyl-8-propyl-9H-purin-6-ylamino)propan-2-ol;
1-(4-(2,3-dimethylphenyl)piperazin-1-yl)-3-(9-phenyl-9H-purin-6-ylamino)propan-2-ol;
1-(4-(2,3-dimethylphenyl)piperazin-1-yl)-3-(8-ethyl-9-phenyl-9H-purin-6-ylamino)propan-2-ol;
1-(4-(2,3-dimethylphenyl)piperazin-1-yl)-3-(8,9-diphenyl-9H-purin-6-ylamino)propan-2-ol;
1-(9-(benzo[d][1,3]dioxol-5-yl)-9H-purin-6-ylamino)-3-(4-(2,3-dimethylphenyl)piperazin-1-yl)propan-2-ol;
9-(benzo[d][1,3]dioxol-5-yl)-N-(3-(4-(2,3-dimethylphenyl)piperazin-1-yl)propyl)-9H-purine-6-amine;
1-(9-(benzo[d][1,3]dioxol-5-yl)-8-methyl-9H-purin-6-ylamino)-3-(4-(2,3-dimethylphenyl)piperazin-1-yl)propan-2-ol;
9-(benzo[d][1,3]dioxol-5-yl)-N-(3-(4-(2,3-dimethylphenyl)piperazin-1-yl)propyl)-8-methyl-9H-purine-6-amine;
9-(benzo[d][1,3]dioxol-5-yl)-N-(3-(4-(2,3-dimethylphenyl)piperazin-1-yl)propyl)-8-ethyl-9H-purine-6-amine;
1-(9-(benzo[d][1,3]dioxol-5-yl)-8-ethyl-9H-purin-6-ylamino)-3-(4-(2,3-dimethylphenyl)piperazin-1-yl)propan-2-ol;
9-(2,3-dihydrobenzo[b][1,4]dioxin-6-yl)-N-(3-(4-(2,3-dimethylphenyl)piperazin-1-yl)propyl)-9H-purine-6-amine;
1-(9-(2,3-dihydrobenzo[b][1,4]dioxin-6-yl)-9H-purin-6-ylamino)-3-(4-(2,3-dimethylphenyl)piperazin-1-yl)propan-2-ol;
9-(2,3-dihydrobenzo[b][1,4]dioxin-6-yl)-N-(3-(4-(2,3-dimethylphenyl)piperazin-1-yl)propyl)-8-methyl-9H-purine-6-amine;
1-(9-(2,3-dihydrobenzo[b][1,4]dioxin-6-yl)-8-methyl-9H-purin-6-ylamino)-3-(4-(2,3-dimethylphenyl)piperazin-1-yl)propan-2-ol;
9-(2,3-dihydrobenzo[b][1,4]dioxin-6-yl)-N-(3-(4-(2,3-dimethylphenyl)piperazin-1-yl)propyl)-8-ethyl-9H-purine-6-amine;
1-(9-(2,3-dihydrobenzo[b][1,4]dioxin-6-yl)-8-ethyl-9H-purin-6-ylamino)-3-(4-(2,3-dimethylphenyl)piperazin-1-yl)propan-2-ol;
N-(3-(4-(2,3-dimethylphenyl)piperazin-1-yl)propyl)-9-(4-fluorophenyl)-9H-purine-6-amine;
1-(4-(2,3-dimethylphenyl)piperazin-1-yl)-3-(9-(4-fluorophenyl)-9H-purin-6-ylamino)propan-2-ol;
N-(3-(4-(2,3-dimethylphenyl)piperazin-1-yl)propyl)-9-(4-fluorophenyl)-8-methyl-9H-purine-6-amine;

1-(4-(2,3-dimethylphenyl)piperazin-1-yl)-3-(9-(4-fluorophenyl)-8-methyl-9H-purin-6-ylamino)propan-2-ol;
N-(3-(4-(2,3-dimethylphenyl)piperazin-1-yl)propyl)-8-ethyl-9-(4-fluorophenyl)-9H-purine-6-amine;
1-(4-(2,3-dimethylphenyl)piperazin-1-yl)-3-(8-ethyl-9-(4-fluorophenyl)-9H-purin-6-ylamino)propan-2-ol;
8-tert-butyl-N-(3-(4-(2,3-dimethylphenyl)piperazin-1-yl)propyl)-9-phenyl-9H-purine-6-amine;
1-(8-tert-butyl-9-phenyl-9H-purin-6-ylamino)-3-(4-(2,3-dimethylphenyl)piperazin-1-yl)propan-2-ol;
N-(2-(4-(2,3-dimethylphenyl)piperazin-1-yl)ethyl)-9-(4-fluorophenyl)-8-methyl-9H-purine-6-amine;
N-(2-(4-(2,3-dimethylphenyl)piperazin-1-yl)ethyl)-8-ethyl-9-(4-fluorophenyl)-9H-purine-6-amine;
9-(benzo[d][1,3]dioxol-5-yl)-N-(2-(4-(2,3-dimethylphenyl)piperazin-1-yl)ethyl)-8-methyl-9H-purine-6-amine;
9-(benzo[d][1,3]dioxol-5-yl)-N-(2-(4-(2,3-dimethylphenyl)piperazin-1-yl)ethyl)-8-ethyl-9H-purine-6-amine;
9-(2,3-dihydrobenzo[b][1,4]dioxin-6-yl)-N-(2-(4-(2,3-dimethylphenyl)piperazin-1-yl)ethyl)-8-methyl-9H-purine-6-amine;
9-(2,3-dihydrobenzo[b][1,4]dioxin-6-yl)-N-(2-(4-(2,3-dimethylphenyl)piperazin-1-yl)ethyl)-8-ethyl-9H-purine-6-amine;
N-(2-(4-(2,3-dimethylphenyl)piperazin-1-yl)ethyl)-9-(4-methoxyphenyl)-8-methyl-9H-purine-6-amine;
N-(3-(4-(2,3-dimethylphenyl)piperazin-1-yl)propyl)-9-(4-methoxyphenyl)-8-methyl-9H-purine-6-amine;
1-(4-(2,3-dimethylphenyl)piperazin-1-yl)-3-(9-(4-methoxyphenyl)-8-methyl-9H-purin-6-ylamino)propan-2-ol;
N-(2-(4-(2,3-dimethylphenyl)piperazin-1-yl)ethyl)-8-ethyl-9-(4-methoxyphenyl)-9H-purine-6-amine;
N-(3-(4-(2,3-dimethylphenyl)piperazin-1-yl)propyl)-8-ethyl-9-(4-methoxyphenyl)-9H-purine-6-amine;
1-(4-(2,3-dimethylphenyl)piperazin-1-yl)-3-(8-ethyl-9-(4-methoxyphenyl)-9H-purin-6-ylamino)propan-2-ol;
N-(3-(4-(3-chloro-2-methylphenyl)piperazin-1-yl)propyl)-8,9-diphenyl-9H-purine-6-amine;
N-(4-(4-(2,3-dimethylphenyl)piperazin-1-yl)butyl)-8,9-diphenyl-9H-purine-6-amine;
9-(4-chlorophenyl)-N-(2-(4-(2,3-dimethylphenyl)piperazin-1-yl)ethyl)-8-methyl-9H-purine-6-amine;
9-(4-chlorophenyl)-N-(3-(4-(2,3-dimethylphenyl)piperazin-1-yl)propyl)-8-methyl-9H-purine-6-amine;
1-(9-(4-chlorophenyl)-8-methyl-9H-purin-6-ylamino)-3-(4-(2,3-dimethylphenyl)piperazin-1-yl)propan-2-ol;
9-(4-chlorophenyl)-N-(2-(4-(2,3-dimethylphenyl)piperazin-1-yl)ethyl)-8-ethyl-9H-purine-6-amine;
9-(4-chlorophenyl)-N-(3-(4-(2,3-dimethylphenyl)piperazin-1-yl)propyl)-8-ethyl-9H-purine-6-amine;
1-(9-(4-chlorophenyl)-8-ethyl-9H-purin-6-ylamino)-3-(4-(2,3-dimethylphenyl)piperazin-1-yl)propan-2-ol;
N-(2-(4-(2,3-dimethylphenyl)piperazin-1-yl)ethyl)-8-methyl-9-(4-(trifluoromethyl)phenyl)-9H-purine-6-amine;
N-(3-(4-(2,3-dimethylphenyl)piperazin-1-yl)propyl)-8-methyl-9-(4-(trifluoromethyl)phenyl)-9H-purine-6-amine;
N-(2-(4-(2,3-dimethylphenyl)piperazin-1-yl)ethyl)-8-ethyl-9-(4-(trifluoromethyl)phenyl)-9H-purine-6-amine;
N-(3-(4-(2,3-dimethylphenyl)piperazin-1-yl)propyl)-8-ethyl-9-(4-(trifluoromethyl)phenyl)-9H-purine-6-amine;
N-(3-(4-(2,3-dimethylphenyl)piperazin-1-yl)propyl)-9-(4-fluorophenyl)-8-phenyl-9H-purine-6-amine;
9-(4-chlorophenyl)-N-(3-(4-(2,3-dimethylphenyl)piperazin-1-yl)propyl)-8-phenyl-9H-purine-6-amine;
N-(3-(4-(2,3-dimethylphenyl)piperazin-1-yl)propyl)-9-(4-methoxyphenyl)-8-phenyl-9H-purine-6-amine;
N-(3-(4-(2,3-dimethylphenyl)piperazin-1-yl)propyl)-8-phenyl-9-(4-(trifluoromethyl)phenyl)-9H-purine-6-amine;
9-(benzo[d][1,3]dioxol-5-yl)-N-(3-(4-(2,3-dimethylphenyl)piperazin-1-yl)propyl)-8-phenyl-9H-purine-6-amine;
9-(2,3-dihydrobenzo[b][1,4]dioxin-6-yl)-N-(3-(4-(2,3-dimethylphenyl)piperazin-1-yl)propyl)-8-phenyl-9H-purine-6-amine;
N-(2-(4-(2,3-dimethylphenyl)piperazin-1-yl)ethyl)-8-methyl-9-(4-(methylthio)phenyl)-9H-purine-6-amine hydrochloride;
N-(3-(4-(2,3-dimethylphenyl)piperazin-1-yl)propyl)-8-methyl-9-(4-(methylthio)phenyl)-9H-purine-6-amine hydrochloride;
N-(2-(4-(2,3-dimethylphenyl)piperazin-1-yl)ethyl)-8-ethyl-9-(4-(methylthio)phenyl)-9H-purine-6-amine hydrochloride;
N-(3-(4-(2,3-dimethylphenyl)piperazin-1-yl)propyl)-8-ethyl-9-(4-(methylthio)phenyl)-9H-purine-6-amine hydrochloride;
N-(2-(4-(2,3-dimethylphenyl)piperazin-1-yl)ethyl)-9-(4-(methylthio)phenyl)-8-phenyl-9H-purine-6-amine hydrochloride;
N-(3-(4-(2,3-dimethylphenyl)piperazin-1-yl)propyl)-9-(4-(methylthio)phenyl)-8-phenyl-9H-purine-6-amine hydrochloride;
N-(2-(4-(2,3-dimethylphenyl)piperazin-1-yl)ethyl)-9-phenyl-8-(thiophen-2-yl)-9H-purine-6-amine hydrochloride;
N-(3-(4-(2,3-dimethylphenyl)piperazin-1-yl)propyl)-9-phenyl-8-(thiophen-2-yl)-9H-purine-6-amine hydrochloride;
8-cyclopentyl-N-(2-(4-(2,3-dimethylphenyl)piperazin-1-yl)ethyl)-9-phenyl-9H-purine-6-amine hydrochloride;
N-(4-(4-(2,3-dimethylphenyl)piperazin-1-yl)butyl)-9-(4-methoxyphenyl)-8-phenyl-9H-purine-6-amine hydrochloride;
N-(4-(4-(2,3-dimethylphenyl)piperazin-1-yl)butyl)-9-(4-(methylthio)phenyl)-8-phenyl-9H-purine-6-amine hydrochloride;
N-(4-(4-(2,3-dimethylphenyl)piperazin-1-yl)butyl)-9-(4-fluorophenyl)-8-phenyl-9H-purine-6-amine hydrochloride;
9-(2,3-dihydrobenzo[b][1,4]dioxin-6-yl)-N-(4-(4-(2,3-dimethylphenyl)piperazin-1-yl)butyl)-8-phenyl-9H-purine-6-amine hydrochloride;
N-(4-(4-(2,3-dimethylphenyl)piperazin-1-yl)butyl)-8-phenyl-9-(4-(trifluoromethyl)phenyl)-9H-purine-6-amine hydrochloride;
N-(3-(4-(2,3-dimethylphenyl)piperazin-1-yl)propyl)-N-methyl-8,9-diphenyl-9H-purine-6-amine hydrochloride;
N-(3-(4-(3-chloro-2-methylphenyl)piperazin-1-yl)propyl)-N-methyl-8,9-diphenyl-9H-purine-6-amine hydrochloride;
N-(3-(4-(2,3-dichlorophenyl)piperazin-1-yl)propyl)-N-methyl-8,9-diphenyl-9H-purine-6-amine hydrochloride;
(S)-1-(4-(2,3-dimethylphenyl)piperazin-1-yl)-3-(8,9-diphenyl-9H-purin-6-ylamino)propan-2-ol hydrochloride;

(S)-1-(4-(3-chloro-2-methylphenyl)piperazin-1-yl)-3-(8,9-diphenyl-9H-purin-6-ylamino)propan-2-ol hydrochloride;
(S)-1-(4-(2,3-dichlorophenyl)piperazin-1-yl)-3-(8,9-diphenyl-9H-purin-6-ylamino)propan-2-ol hydrochloride;
(R)-1-(4-(2,3-dimethylphenyl)piperazin-1-yl)-3-(8,9-diphenyl-9H-purin-6-ylamino)propan-2-ol hydrochloride;
(R)-1-(4-(3-chloro-2-methylphenyl)piperazin-1-yl)-3-(8,9-diphenyl-9H-purin-6-ylamino)propan-2-ol hydrochloride;
(R)-1-(4-(2,3-dichlorophenyl)piperazin-1-yl)-3-(8,9-diphenyl-9H-purin-6-ylamino)propan-2-ol hydrochloride;
N-(4-(4-(2,3-dimethylphenyl)piperazin-1-yl)butyl)-9-phenyl-8-(thiophen-2-yl)-9H-purine-6-amine hydrochloride;
1-(4-(2,3-dimethylphenyl)piperazin-1-yl)-3-((8,9-diphenyl-9H-purin-6-yl)(methyl)amino)propan-2-ol hydrochloride;
1-(4-(3-chloro-2-methylphenyl)piperazin-1-yl)-3-((8,9-diphenyl-9H-purin-6-yl)(methyl)amino)propan-2-ol hydrochloride;
1-(4-(2,3-dichlorophenyl)piperazin-1-yl)-3-((8,9-diphenyl-9H-purin-6-yl)(methyl)amino)propan-2-ol hydrochloride;
N-(4-(4-(2,3-dimethylphenyl)piperazin-1-yl)butyl)-N-methyl-8,9-diphenyl-9H-purine-6-amine hydrochloride;
4-(4-(2,3-dimethylphenyl)piperazin-1-yl)-1-((8,9-diphenyl-9H-purin-6-yl)(methyl)amino)butan-2-ol hydrochloride;
N-(4-(4-(2,3-dimethylphenyl)piperazin-1-yl)butyl)-N,2-dimethyl-8,9-diphenyl-9H-purine-6-amine hydrochloride;
N-(4-(4-(2,3-dimethylphenyl)-1,4-diazepan-1-yl)butyl)-8,9-diphenyl-9H-purine-6-amine hydrochloride;
N-(4-(4-(2,3-dimethylphenyl)-1,4-diazepan-1-yl)butyl)-2-methyl-8,9-diphenyl-9H-purine-6-amine hydrochloride;
N-(4-(4-(2,3-dimethylphenyl)-2-methylpiperazin-1-yl)butyl)-8,9-diphenyl-9H-purine-6-amine hydrochloride;
N-(4-(4-(2,3-dimethylphenyl)-2-methylpiperazin-1-yl)butyl)-2-methyl-8,9-diphenyl-9H-purine-6-amine hydrochloride;
4-(4-(2,3-dimethylphenyl)piperazin-1-yl)-1-(methyl(2-methyl-8,9-diphenyl-9H-purin-6-yl)amino)butan-2-ol hydrochloride;
4-(4-(2,3-dimethylphenyl)-1,4-diazepan-1-yl)-1-((8,9-diphenyl-9H-purin-6-yl)(methyl)amino)butan-2-ol hydrochloride;
4-((R)-4-(2,3-dimethylphenyl)-2-methylpiperazin-1-yl)-1-((8,9-diphenyl-9H-purin-6-yl)(methyl)amino)butan-2-ol hydrochloride;
4-((S)-4-(2,3-dimethylphenyl)-2-methylpiperazin-1-yl)-1-((8,9-diphenyl-9H-purin-6-yl)(methyl)amino)butan-2-ol hydrochloride;
4-(4-(2,3-dimethylphenyl)-2-methylpiperazin-1-yl)-1-((8,9-diphenyl-9H-purin-6-yl)(methyl)amino)butan-2-ol hydrochloride;
4-(4-(2,3-dimethylphenyl)piperazin-1-yl)-1-(8,9-diphenyl-9H-purin-6-ylamino)butan-2-ol hydrochloride;
1-(4-(2,3-dimethylphenyl)piperazin-1-yl)-4-(8,9-diphenyl-9H-purin-6-ylamino)butan-2-ol hydrochloride;
N-(4-(4-(2,3-dimethylphenyl)-2-methylpiperazin-1-yl)butyl)-N-methyl-8,9-diphenyl-9H-purine-6-amine hydrochloride;
N-(4-(4-(2,3-dimethylphenyl)-2-methylpiperazin-1-yl)butyl)-N,2-dimethyl-8,9-diphenyl-9H-purine-6-amine hydrochloride;
N-(4-(4-(2,3-dimethylphenyl)-1,4-diazepan-1-yl)butyl)-N-methyl-8,9-diphenyl-9H-purine-6-amine hydrochloride;
N-(4-(4-(2,3-dimethylphenyl)-1,4-diazepan-1-yl)butyl)-N,2-dimethyl-8,9-diphenyl-9H-purine-6-amine hydrochloride;
N-(4-(4-(2,3-dimethylphenyl)-2-methylpiperazin-1-yl)butyl)-N-ethyl-8,9-diphenyl-9H-purine-6-amine hydrochloride;
N-(4-(4-(2,3-dimethylphenyl)-2-methylpiperazin-1-yl)butyl)-N-ethyl-2-methyl-8,9-diphenyl-9H-purine-6-amine hydrochloride;
N-(4-(4-(2,3-dimethylphenyl)-1,4-diazepan-1-yl)butyl)-N-ethyl-8,9-diphenyl-9H-purine-6-amine hydrochloride;
N-(4-(4-(2,3-dimethylphenyl)-1,4-diazepan-1-yl)butyl)-N-ethyl-2-methyl-8,9-diphenyl-9H-purine-6-amine hydrochloride;
(S)—N-(4-(4-(2,3-dimethylphenyl)-2-methylpiperazin-1-yl)butyl)-8,9-diphenyl-9H-purine-6-amine hydrochloride;
(S)—N-(4-(4-(2,3-dimethylphenyl)-2-methylpiperazin-1-yl)butyl)-2-methyl-8,9-diphenyl-9H-purine-6-amine hydrochloride;
(R)—N-(4-(4-(2,3-dimethylphenyl)-2-methylpiperazin-1-yl)butyl)-8,9-diphenyl-9H-purine-6-amine hydrochloride;
(R)—N-(4-(4-(2,3-dimethylphenyl)-2-methylpiperazin-1-yl)butyl)-2-methyl-8,9-diphenyl-9H-purine-6-amine hydrochloride;
(S)—N-(4-(4-(2,3-dimethylphenyl)-2-methylpiperazin-1-yl)butyl)-N-methyl-8,9-diphenyl-9H-purine-6-amine hydrochloride;
(S)—N-(4-(4-(2,3-dimethylphenyl)-2-methylpiperazin-1-yl)butyl)-N,2-dimethyl-8,9-diphenyl-9H-purine-6-amine hydrochloride;
(R)—N-(4-(4-(2,3-dimethylphenyl)-2-methylpiperazin-1-yl)butyl)-N-methyl-8,9-diphenyl-9H-purine-6-amine hydrochloride;
(R)—N-(4-(4-(2,3-dimethylphenyl)-2-methylpiperazin-1-yl)butyl)-N,2-dimethyl-8,9-diphenyl-9H-purine-6-amine hydrochloride; and
N-(4-(4-(2,3-dimethylphenyl)piperazin-1-yl)butyl)-2-methyl-8,9-diphenyl-9H-purine-6-amine hydrochloride.

4. A pharmaceutical composition, which comprises the compound according to claim 1 as an active ingredient, and a pharmaceutically acceptable carrier.

5. The pharmaceutical composition of claim 4 which further comprises a selective serotonine reuptake inhibitor, a serotonin and norepinephrine reuptake inhibitor or a mixture thereof.

6. A method for treating depressive disorders, which comprises administering the compound of claim 1 to a mammal in need thereof.

* * * * *